(12) United States Patent
Ali et al.

(10) Patent No.: US 7,737,295 B2
(45) Date of Patent: Jun. 15, 2010

(54) CETP INHIBITORS

(75) Inventors: Amjad Ali, Freehold, NJ (US); Joann Bohn, Woodbridge, NJ (US); Qiaolin Deng, Edison, NJ (US); Zhijian Lu, Clinton, NJ (US); Peter J. Sinclair, Scotch Plains, NJ (US); Gayle E. Taylor, Jersey City, NJ (US); Christopher F. Thompson, Clark, NJ (US); Nazia Quraishi, Arlington, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 825 days.

(21) Appl. No.: 11/578,694

(22) PCT Filed: Apr. 8, 2005

(86) PCT No.: PCT/US2005/012196

§ 371 (c)(1),
(2), (4) Date: Oct. 12, 2006

(87) PCT Pub. No.: WO2005/100298

PCT Pub. Date: Oct. 27, 2005

(65) Prior Publication Data

US 2007/0225365 A1      Sep. 27, 2007

Related U.S. Application Data

(60) Provisional application No. 60/561,611, filed on Apr. 13, 2004.

(51) Int. Cl.
C07C 261/00 (2006.01)
C07C 211/00 (2006.01)
A01N 47/10 (2006.01)
(52) U.S. Cl. ............... 560/115; 560/132; 564/336; 564/337; 514/476
(58) Field of Classification Search ............ None
See application file for complete search history.

(56) References Cited

U.S. PATENT DOCUMENTS

2002/0035136 A1   3/2002   Liu et al.
2005/0059810 A1   3/2005   Maeda et al.

FOREIGN PATENT DOCUMENTS

WO   WO03/064376     8/2003
WO   WO2004/020393   3/2004
WO   WO2004/092136   10/2004

OTHER PUBLICATIONS

Lin N-H et al. "Siynthesis and biological evaluation of 1-benzyl-5-(3-biphenyl-2-yl-propyl)-1H-imidazole as novel farnesyltransferase inhibitor"; Bioorganic & Medicinal Chemistry Letters, Pergamon, Elsevier Science, GB; vol. 14, No. 20, Oct. 18, 2004 pp. 5057-5062 XP004565431; Compounds 20, 21.

*Primary Examiner*—Karl J Puttlitz
(74) *Attorney, Agent, or Firm*—Mark R. Daniel; James L. McGinnis

(57) ABSTRACT

Compounds of Formula I, including pharmaceutically acceptable salts of the compounds, are CETP inhibitors, and are useful for raising HDL-cholesterol, reducing LDL-cholesterol, and for treating or preventing atherosclerosis. In the compounds of Formula 1, $A^1$ and $A^2$ are each an aromatic ring, a 5-6-membered heterocyclic ring, an aromatic ring fused to a heterocyclic ring, a phenyl ring fused to a heterocyclic ring, or a cycloalkyl ring.

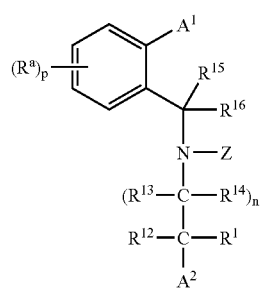

16 Claims, No Drawings

CETP INHIBITORS

CROSS REFERENCE TO RELATED APPLICATIONS

This application is a U.S. National Phase application under 35 U.S.C. §371 of PCT Application No. PCT/US2005/012196, filed Apr. 8, 2005, which claims priority under 35 U.S.C. §119(e) from U.S. Application No. 60/561,611, filed Apr. 13, 2004.

FIELD OF THE INVENTION

This invention relates to a class of chemical compounds that inhibit cholesterol ester transfer protein (CETP) and therefore may have utility in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) Purification and characterization of human plasma cholesteryl ester transfer protein. *J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) Phospholipid and cholesteryl ester transfer activities in plasma from 14 vertebrate species. Relation to atherogenesis susceptibility, *Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) Pros and cons of inhibiting cholesteryl ester transfer protein, *Curr. Opin. Lipidol.* 11(6), 589-596). These studies have clearly demonstrated an inverse correlation between plasma HDL-C concentration and CETP activity (see Inazu, A., et. al. (2000) Cholesteryl ester transfer protein and atherosclerosis, *Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies. No CETP inhibitors are currently being marketed. One CETP inhibitor, torcetrapib, is currently in clinical trials, and is being developed for use in combination with atorvastatin. It is not currently being developed as a drug for monotherapy. New compounds are needed so that additional pharmaceutical compounds can be found that are safe and effective, either alone or in combination with other drugs that are used for treatment of lipid disorders. The compounds described herein are very potent CETP inhibitors and may be suitable for use in monotherapy and/or combination therapy.

SUMMARY OF THE INVENTION

Compounds having Formula I, including pharmaceutically acceptable salts of the compounds, are CETP inhibitors, having the utilities described below:

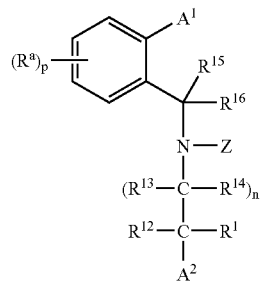

In the compounds of Formula 1:
$A^1$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 14 heteroatoms independently selected from N, S, and O, and optionally also comprising 1-3 double bonds and a carbonyl group or —N(O)— group, wherein the point of attachment of $A^1$ to the attached phenyl ring is a carbon atom; and (d) a benzoheterocyclic ring comprising a phenyl ring fused to a 5-6-membered heterocyclic ring having 1-3 heteroatoms independently selected from O, N, and S, and optionally 1-2 double bonds, wherein the point of attachment of $A^1$ to the attached phenyl ring is a carbon atom;

$A^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 14 heteroatoms independently selected from N, S, and O, and optionally also comprising 1-3 double bonds and a carbonyl group or —N(O)— group;
(d) a benzoheterocyclic ring comprising a phenyl ring fused to a 5-6-membered heterocyclic ring having 1-3 heteroatoms independently selected from O, N, and S, and optionally 1-2 double bonds; and
(e) a —$C_3$-$C_8$ cycloalkyl ring optionally having 1-3 double bonds;

wherein $A^1$ and $A^2$ are each optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$ alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$ alkyl, —C(=O)$C_3$-$C_8$ cycloalkyl, —C(=O)H, —$CO_2$H, —$CO_2C_1$-$C_6$ alkyl, —C(=O)$SC_1$-$C_6$ alkyl, —$NR^{10}R^{11}$, —C(=O)$NR^{10}R^{11}$, —$NR^{10}$C(=O)$OC_1$-$C_6$ alkyl, —$NR^{10}$C(=O)$NR^{10}R^{11}$, —S(O)$_xC_1$-$C_6$ alkyl, —S(O)$_yNR^{10}R^{11}$, —$NR^{10}$S(O)$_yNR^{10}R^{11}$, halogen, —CN, —$NO_2$, and a 5-6-membered heterocyclic ring having 14 heteroatoms independently selected from N, S, and O, said heterocyclic ring optionally also comprising a carbonyl group and optionally also comprising 1-3 double bonds, wherein for compounds in which $R^a$ is selected from the group consisting of a heterocyclic ring, —$C_3$-$C_8$ cycloalkyl, —$OC_3$-$C_8$ cycloalkyl, and —C(=O)$C_3$-$C_8$ cycloalkyl, the heterocyclic ring and —$C_3$-$C_8$ cycloalkyl groups of $R^a$ are optionally substituted with 1-5 substituent groups independently selected from halogen, —$C_1$-$C_3$ alkyl, and —$OC_1$-$C_3$ alkyl, wherein —$C_1$-$C_3$ alkyl, and —$OC_1$-$C_3$ alkyl are optionally substituted with 1-7 halogens, wherein for compounds in which $R^a$ is selected from the group consisting of —$C_1$-$C_6$ alkyl, —$C_2$-$C_6$ alkenyl, —$C_2$-$C_6$ alkynyl, —$OC_1$-$C_6$ alkyl, —$OC_2$-$C_6$ alkenyl, —$OC_2$-$C_6$ alkynyl, —C(=O)$C_1$-$C_6$ alkyl —$CO_2C_1$-$C_6$ alkyl, —C(=O)$SC_1$-$C_6$ alkyl, —$NR^{10}$C(=O)$OC_1$-$C_6$ alkyl, and —S(O)$_xC_1$-$C_6$ alkyl, the alkyl, alkenyl, and alkynyl groups of $R^a$ are optionally substituted with 1-15 halogens and are optionally also substituted with 1-3 substituent groups independently selected from (a) —OH, (b) —CN, (c) —$NR^{10}R^{11}$, (d) —$C_3$-$C_8$ cycloalkyl optionally having 1-3 double bonds and optionally substituted with 1-15 halogens, (e) —$OC_1$-$C_4$ alkyl optionally substituted with 1-9 halogens and optionally also substituted with 1-2 substituent groups independently selected from —$OC_1$-$C_2$ alkyl, (f) —$OC_3$-$C_8$ cycloalkyl optionally having 1-3 double bonds and optionally substituted with 1-15 halogens, (g) —$CO_2$H, (h) —C(=O)$CH_3$, and (i) —$CO_2C_1$-$C_4$ alkyl which is optionally substituted with 1-9 halogens;

n is an integer selected from 0 and 1;
p is an integer from 0-4;
x is an integer selected from 0, 1, and 2;
y is an integer selected from 1 and 2;

Z is selected from the group consisting of —S(O)$_xC_1$-$C_6$ alkyl, —S(O)$_2NR^{17}R^{18}$, —C(=S)$OC_1$-$C_6$ alkyl, and —C(=O)X, wherein X is selected from the group consisting of H, —$C_1$-$C_6$ alkyl, —$OC_1$-$C_6$ alkyl, —$SC_1$-$C_6$ alkyl, and —$NR^{10}R^{11}$; wherein —$C_1$-$C_6$ alkyl in all instances is optionally substituted with 1-13 halogens and 1-2 substituents independently selected from —$OC_1$-$C_3$ alkyl, —CN, and —$NO_2$, wherein —$OC_1$-$C_3$ alkyl is optionally substituted with 1-7 halogens and is optionally also substituted with 1-2 —$OC_1$-$C_2$ alkyl;

$R^1$, $R^{12}$, $R^{13}$, $R^{14}$, $R^{15}$, and $R^{16}$ are each independently selected from the group consisting of H, —OH, halogen, —$C_1$-$C_4$ alkyl, —$C_3$-$C_6$ cycloalkyl, —$OC_1$-$C_4$ alkyl, and —$NR^{10}R^{11}$, wherein —$C_1$-$C_4$ alkyl, —$C_3$-$C_6$ cycloalkyl, and —$OC_1$-$C_4$ alkyl are each optionally substituted with 1-9 halogens and are each optionally also substituted with 1-2 groups independently selected from —OH, —C(=O)$CH_3$, —OC(=O)$CH_3$, —$OC_1$-$C_2$ alkyl, and —$OC_1$-$C_2$ alkylene(OC$_1$-$C_2$ alkyl);

$R^{10}$ and $R^{11}$ are each independently selected from H, —$C_1$-$C_5$ alkyl, —C(=O)$C_1$-$C_5$ alkyl and —S(O)$_yC_1$-$C_5$ alkyl, wherein —$C_1$-$C_5$ alkyl in all instances is optionally substituted with 1-11 halogens; and $R^{17}$ and $R^{18}$ are each independently selected from the group consisting of H, —$C_1$-$C_5$ alkyl, and —$C_3$-$C_7$ cycloalkyl, wherein —$C_1$-$C_5$ alkyl, and —$C_3$-$C_7$ cycloalkyl are optionally substituted with 1-13 halogens.

DETAILED DESCRIPTION OF THE INVENTION

A subgroup of the compounds of this invention has the structure of Formula Ia, written below, or a pharmaceutically acceptable salt thereof:

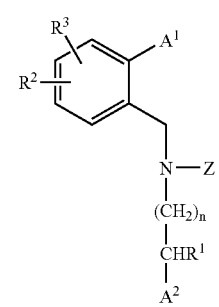

Ia

In the compounds of Formula Ia:
$A^1$ is selected from the group consisting of:
(a) an aromatic ring selected from phenyl and naphthyl;
(b) a 5-6-membered heterocyclic ring having 1-4 heteroatoms independently selected from N, S, and O, and optionally also comprising 1-3 double bonds and a carbonyl group or —N(O)— group, wherein the point of attachment of $A^1$ to the attached phenyl ring is a carbon atom; and
(c) a bicyclic ring comprising a phenyl ring fused to a 5-6-membered heterocyclic ring having 1-3 heteroatoms independently selected from O, N, and S, and optionally 1-2 double bonds, wherein the point of attachment of $A^1$ to the attached phenyl ring is a carbon atom;

wherein $A^1$ is optionally substituted with 1-4 substituent groups independently selected from —$C_1$-$C_5$ alkyl, —$OC_1$-$C_3$ alkyl, —$CO_2C_1$-$C_3$ alkyl, —$CO_2H$, halogen, —$NR^{10}R^{11}$, —$C(=O)C_1$-$C_3$ alkyl, —$C(=O)H$, —$C(=O)NR^{10}R^{11}$, —$SC_1$-$C_3$ alkyl, —$C_2$-$C_3$ alkenyl, —CN, —$NO_2$, —$C_3$-$C_6$ cycloalkyl, and a 5-6-membered heterocyclic ring having 1-3 heteroatoms independently selected from N, S, and O, and optionally also comprising 1-3 double bonds, wherein —$C_1$-$C_3$ alkyl and —$C_1$-$C_5$ alkyl in all occurrences are optionally substituted with 1-6 substituents independently selected from 1-5 halogens and one —OH group; and —$C_3$-$C_6$ cycloalkyl and the 5-6-membered heterocyclic ring are optionally substituted with 1-3 substituents independently selected from halogen and —$C_1$-$C_3$ alkyl; and —$C_2$-$C_3$ alkenyl is optionally substituted with 1-3 halogens;

$A^2$ is selected from the group consisting of phenyl, naphthyl, —$C_3$-$C_6$ cycloalkyl, and a heterocyclic 5-6 membered ring having 1-3 heteroatoms independently selected from O, N, and S, and optionally also comprising 1-3 double bonds and a carbonyl group or —N(O)— group, wherein $A^2$ is optionally substituted with 1-2 substituent groups independently selected from —$C_1$-$C_4$ alkyl, —$OC_1$-$C_3$ alkyl, —$C(=O)C_1$-$C_3$ alkyl, —$C(=O)H$, —$NO_2$, —CN, —$S(O)_xC_1$-$C_3$ alkyl, —$NHS(O)_2C_1$-$C_3$ alkyl, —$NR^{10}R^{11}$, —$NR^{10}C(=O)R^{11}$, —$C_2$-$C_3$ alkenyl, —$C(=O)NR^{10}R^{11}$, halogen, —$C_3$-$C_6$ cycloalkyl, and a 5-6-membered heterocyclic ring having 1-3 heteroatoms independently selected from N, S, and O, and optionally also comprising 1-3 double bonds, wherein $C_1$-$C_3$ alkyl, $C_1$-$C_4$ alkyl, and $C_2$-$C_3$ alkenyl in all instances are optionally substituted with 1-3 halogens, and —$C_3$-$C_6$ cycloalkyl and the 5-6-membered heterocyclic ring are optionally substituted with 1-3 substituents independently selected from halogen and —$C_1$-$C_3$ alkyl;

x is an integer selected from 0, 1, and 2;

n is an integer selected from 0 and 1;

$R^1$ is selected from the group consisting of H, OH, $C_1$-$C_3$ alkyl, and —$OC_1$-$C_3$ alkyl, wherein $C_1$-$C_3$ alkyl and —$OC_1$-$C_3$ alkyl are each optionally substituted with 1-3 halogens and also are optionally substituted with one —$OC_1$-$C_2$ alkyl;

$R^2$ and $R^3$ are each independently selected from the group consisting of H, halogen, —$NR^{10}R^{11}$, —$C_1$-$C_3$ alkyl, —$OC_1$-$C_3$ alkyl, —$C_2$-$C_3$ alkenyl, —$C_3$-$C_6$ cycloalkyl optionally having a double bond, —$OC_3$-$C_6$ cycloalkyl optionally having a double bond, —$C(=O)C_1$-$C_3$ alkyl, —$C(=O)C_3$-$C_6$ cycloalkyl, —$C(=O)H$, —$CO_2H$, —$CO_2C_1$-$C_3$ alkyl, —$C(=O)NR^{10}R^{11}$, —CN, —$NO_2$, and a 5-6-membered heterocyclic ring having 1-4 heteroatoms independently selected from N, S, and O, and optionally 1-3 double bond, wherein $C_1$-$C_3$ alkyl and —$C_2$-$C_3$ alkenyl in all instances are optionally substituted with 1-5 halogens, and —$C_3$-$C_6$ cycloalkyl and the 5-6-membered heterocyclic ring are in all occurrences optionally substituted with 1-3 substituents independently selected from halogen, —$C_1$-$C_3$ alkyl, —$OC_1$-$C_3$ alkyl, —$CF_3$, and —$OCF_3$; and $R^{10}$ and $R^{11}$ are each independently selected from H and —$C_1$-$C_3$ alkyl.

In a subgroup of Formula Ia, $R^2$ and $R^3$ are each independently selected from the group consisting of H, halogen, —$NR^{10}R^{11}$, —$C_1$-$C_3$ alkyl, —$OC_1$-$C_3$ alkyl, —CN, —$NO_2$, and pyridyl, wherein $C_1$-$C_3$ alkyl in all instances is optionally substituted with 1-3 halogens.

A subgroup of Formula Ia has Formula Ib:

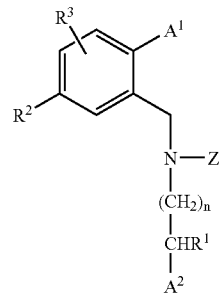

Ib where the definitions of the groups are as defined previously.

In subgroups of compounds having Formula Ia and Formula Ib, $R^2$ is selected from H, halogen, —$NR^{10}R^{11}$, —$C_1$-$C_3$ alkyl, —$OC_1$-$C_3$ alkyl, —CN, —$NO_2$, and pyridyl, wherein $C_1$-$C_3$ alkyl in all instances is optionally substituted with 1-3 halogens; and $R^3$ is selected from H, halogen, —$CH_3$, —$CF_3$, —$OCH_3$, and —$OCF_3$.

In subgroups of Formula I, Ia, and Ib, $R^1$ is H, halogen, or $C_1C_3$ alkyl, wherein $C_1$-$C_3$ alkyl is optionally substituted with 1-3 halogens.

In subgroups of Formula I, Ia, and Ib, $A^1$ may be phenyl, thienyl, furyl, pyridyl, quinolyl, isoquinolyl, benzofuranyl, dihydrobenzofuranyl, indolyl, dihydroindolyl, oxazolyl, isoxazolyl, or oxadiazolyl.

In subgroups of Formula I, Ia, and Ib, $A^2$ may be phenyl, thienyl, furyl, pyridyl, 1-oxidopyridinyl, quinolyl, isoquinolyl, benzofuranyl, dihydrobenzofuranyl, indolyl, dihydroindolyl, oxazolyl, isoxazolyl, oxadiazolyl, and $C_3$-$C_6$ cycloalkyl.

In subgroups of Formula I, Ia, and Ib, $A^2$ may be phenyl, pyridyl, thienyl, 1-oxidopyridinyl, or cyclohexyl.

In subgroups of Formula I, Ia and Ib, $A^1$ may be one of the following: 2-thienyl, 3-thienyl, 2-furyl, 2-pyridyl, 3-pyridyl, 4-pyridyl, 3-quinolyl, 5-quinolyl, 6-quinolyl, 8-quinolyl, 4-isoquinolyl, 5-isoquinolyl, 4-isoxazolyl, 5-1,2,4-oxadiazolyl, 5-(2,3-dihydrobenzofuranyl), or 5-indolyl, where Al is optionally substituted with 1-2 substituent groups independently selected from —$CH_3$, —$OCH_3$, acetyl, and halogen.

In subgroups of Formula I, Ia and Ib, $A^2$ may be one of the following: 2-pyridyl, 3-pyridyl, 4-pyridyl, 2-thienyl, 3-thienyl, 1-oxidopyridin-3-yl, and cyclohexyl, where $A^2$ is optionally substituted with 1-2 substituents which are independently selected from —$CH_3$, —$OCH_3$, acetyl, and halogen.

In subgroups of Formula I, Ia, and Ib, Z is selected from the group consisting of —$C(=O)C_1$-$C_3$ alkyl, —$C(=O)OC_1$-$C_3$ alkyl, —$S(O)_yC_1$-$C_3$ alkyl, —$C(=O)H$, —$C(O)NR^{10}R^{11}$, —$C(=O)SC_1$-$C_3$ alkyl, and —$C(=S)OC_1$-$C_3$ alkyl.

A subgroup of the compounds of this invention has Formula II:

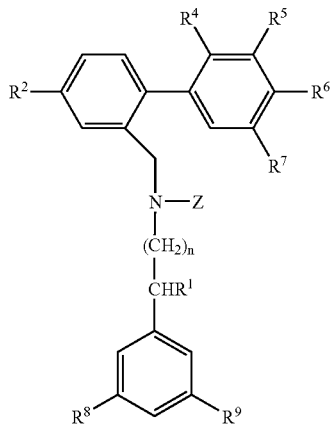

In the compounds of Formula II, $R^2$ is selected from the group consisting of H, halogen, $-NR^{10}R^{11}$, $-OC_1$-$C_3$ alkyl, $C_1$-$C_3$ alkyl, $-CN$, $-NO_2$, and 3-pyridyl, wherein $C_1$-$C_3$ alkyl in all occurrences is optionally substituted with 1-3 halogens;

$R^4$ is selected from the group consisting of H, halogen, $-C_1$-$C_3$ alkyl, $-OC_1$-$C_2$ alkyl, $-SC_1$-$C_2$ alkyl and $-CN$, wherein $-C_1$-$C_3$ alkyl, $-SC_1$-$C_2$ alkyl, and $-OC_1$-$C_2$ alkyl are optionally substituted with 1-3 F;

$R^5$ and $R^6$ are each independently H, halogen, $-CH_3$ or $-OCH_3$, wherein $-CH_3$ and $-OCH_3$ are optionally substituted with 1-3 F;

$R^7$ is selected from the group consisting of H, $-C_1$-$C_5$ alkyl, $-OC_1$-$C_3$ alkyl, $-C_2$-$C_3$ alkenyl, halogen, $-CN$, $-CO_2H$, $-CO_2C_1$-$C_3$ alkyl, $-SC_1$-$C_3$ alkyl, $-C(=O)NR^{10}R^{11}$, $-C(=O)H$, $-C(=O)C_1$-$C_3$ alkyl, and 5-(1,2,4-oxadiazolyl), wherein $-C_1$-$C_3$ alkyl and $-C_1$-$C_5$ alkyl in all occurrences is optionally substituted with 1-6 substituent groups independently selected from 1-5 halogens and one $-OH$, and $-C_2$-$C_3$ alkenyl is optionally substituted with 1-3 halogens;

$R^8$ and $R^9$ are each independently selected from the group consisting of H, $-C_1$-$C_3$ alkyl, halogen, $-S(O)_xC_1$-$C_3$ alkyl, $-NR^{10}R^{11}$, $-OC_1$-$C_3$ alkyl, $C_2$-$C_3$ alkenyl, $-NO_2$, $-CN$, $-C(O)NR^{10}R^{11}$, $-NHC(=O)C_1$-$C_3$ alkyl, $-NHS(O)_2C_1$-$C_3$ alkyl, $CO_2H$, $CO_2C_{1-3}$ alkyl, and pyridyl, wherein $C_1$-$C_3$ alkyl in all occurrences is optionally substituted with 1-3 halogens, and $C_2$-$C_3$ alkenyl is optionally substituted with 1-3 halogens; and $R^{10}$ and $R^{11}$ are each H or $C_1$-$C_3$ alkyl.

In subgroups of Formula Ia, Ib, and II, $R^1$ is H or $CH_3$.

In subgroups of Formula Ia, Ib, and II, $R^2$ is H, $-CF_3$, $-OCH_3$, $-NO_2$, $-CN$, halogen, $-NH_2$ or 3-pyridyl.

In subgroups of Formula Ia, Ib, and II, $R^2$ is a group other than H.

In subgroups of Formula II, $R^4$ is selected from H, halogen, $-CH_3$, $-C_2H_5$, $-OCH_3$, $-OC_2H_5$, $-SCH_3$, and $-CN$.

In subgroups of Formula II, $R^5$ is H or F.

In subgroups of Formula II, $R^6$ is H, F, $-CH_3$, or $-OCH_3$.

In subgroups of Formula II, $R^7$ is selected from H, $C_1$-$C_4$ alkyl, $-C(=O)H$, $-C(=O)CH_3$, $-CH=CH_2$, $-CN$, Cl, F, $-CO_2H$, $-CO_2C_1$-$C_3$ alkyl, $-OCH_3$, $-SCH_3$, $-C(=O)NR^{10}OR^{11}$, $C_3$-$C_6$cycloalkyl and 3-methyl-5-(1,2,4-oxadiazolyl), wherein $C_1$-$C_4$ alkyl and $C_3$-$C_6$cycloalkyl are optionally substituted with 1-6 substituents which are independently selected from 1-5 F and one $-OH$.

In subgroups of Formula II, $R^8$ and $R^9$ each are independently selected from H, $C_1$-$C_2$ alkyl, which is optionally substituted with 1-3 F; halogen; $-CN$; $-NO_2$; $-S(O)_xCH_3$, which is optionally substituted with 1-3F; $-OCH_3$, which is optionally substituted with 1-3 F; $-CH=CH_2$; $-C(=O)H$; $-C(=O)NR^{10}R^{11}$; $-CO_2H$; $-NR^{10}R^{11}$; $-CO_2C_1$-$C_3$ alkyl; $-NHC(=O)CH_3$; $-NHS(O)_2CH_3$; and 4-pyridyl, wherein x is 0, 1, or 2.

In subgroups of Formula I, Ia, Ib, and II, $R^{10}$ and $R^{11}$ are each H or $-CH_3$.

In subgroups of Formula I, Ia, Ib, and II, n is 0. In subgroups of Formula I, Ia, Ib, and II, n is 1.

In subgroups of Formula II, $R^4$ is $-OCH_3$.

In subgroups of Formula II, $R^7$ is $-CH(CH_3)_2$; $-CH(OH)CH_3$; $-CH(OH)CF_3$; $-CH(CH_3)CF_3$; $-C(OH)(CH_3)CF_3$; $-CH_3$, which is optionally substituted with $-OH$ or 1-3 F; $-C_2H_5$, which is optionally substituted with 1-5 F; n-$C_3H_7$; tert-$C_4H_9$; $-C(=O)H$, $-C(=O)CH_3$, $-CH=CH_2$, $-CN$, Cl, F, $-CO_2H$, $-CO_2CH_3$; $-OCH_3$; $-SCH_3$; $-C(=O)NR^{10}R^{11}$; 3-methyl-5-(1,2,4-oxadiazolyl), or $C_3$-$C_6$cycloalkyl.

In subgroups of Formula II, $R^5$ and $R^6$ are H.

In subgroups of Formula II, $R^8$ and $R^9$ are each independently selected from H, $-CH_3$, $-C_2H_5$, $-NO_2$, $-OCH_3$, $-CN$, $-NO_2$, halogen, $S(O)_xCH_3$, $-C(=O)NR^{10}OR^{11}$, and $-CH=CH_2$, where $-CH_3$ and $-OCH_3$ are each independently substituted with 1-3 F.

In subgroups of Formula II, $R^8$ is $-CF_3$, $-NO_2$, Cl, $-CH_3$, $-OCF_3$, or $-OCF_2H$; and $R^9$ is H, $-CF_3$, $-CN$, $-NO_2$, halogen, $-CH_3$, $-C_2H_5$, $-OCH_3$, $-S(O)_xCH_3$, $-CF_2H$, $-C(=O)NR^{10}R^{11}$, or $-CH=CH_2$.

In subgroups of Formula II, at least one of $R^4$ and $R^7$ is a substituent group other than H. In subgroups of Formula II, both of $R^4$ and $R^7$ are substituent groups other than H.

In subgroups of Formula I, Ia, Ib, and II, Z is selected from $-S(O)_2CH_3$ and $-C(=O)X$, where X is selected from H, $-OC_1$-$C_3$ alkyl, $-CH_3$, and $-NR^{10}R^{11}$.

Specific examples of the compounds of this invention are provided in the examples and are summarized in Table 1 below and Tables 2-5 in the examples. The specific embodiments include the compounds and pharmaceutically acceptable salts of the compounds.

TABLE 1

| Example | Structure |
|---------|-----------|
| Ex. 6 | 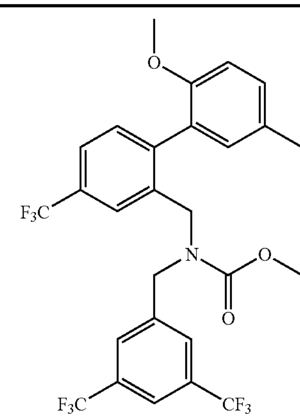 |

TABLE 1-continued

| Example | Structure |
|---------|-----------|
| Ex. 7 | *(biphenyl with 2-methoxy, 5-methyl on one ring; F and CH2-N(C(O)OMe)-CH2-(3,5-bis(trifluoromethyl)phenyl) on the other ring)* |
| Ex. 8 | *(biphenyl with 2-methoxy, 5-isopropyl on one ring; NO2 and CH2-N(C(O)OMe)-CH2-(3,5-bis(trifluoromethyl)phenyl) on the other ring)* |
| Ex. 9 | *(biphenyl with 2-methoxy, 5-isopropyl on one ring; NH2 and CH2-N(C(O)OMe)-CH2-(3,5-bis(trifluoromethyl)phenyl) on the other ring)* |
| Ex. 10 | *(biphenyl with 2-methoxy, 5-isopropyl on one ring; I and CH2-N(C(O)OMe)-CH2-(3,5-bis(trifluoromethyl)phenyl) on the other ring)* |
| Ex. 11 | *(biphenyl with 2-methoxy, 5-isopropyl on one ring; pyridin-3-yl and CH2-N(C(O)OMe)-CH2-(3,5-bis(trifluoromethyl)phenyl) on the other ring)* |
| Ex. 12 | *(biphenyl with 2-methoxy, 5-isopropyl on one ring; CN and CH2-N(C(O)OMe)-CH2-(3,5-bis(trifluoromethyl)phenyl) on the other ring)* |

TABLE 1-continued

| Example | Structure |
|---|---|
| Ex. 13 | (structure) |
| Ex. 14 | (structure) |
| Ex. 19 | (structure) |
| Ex. 22 | (structure) |
| Ex. 28 | (structure) |
| Ex. 29 | (structure) |
| Ex. 30 | (structure) |
| Ex. 31 | (structure) |

TABLE 1-continued
| Example | Structure |
|---------|-----------|
| Ex. 32 | 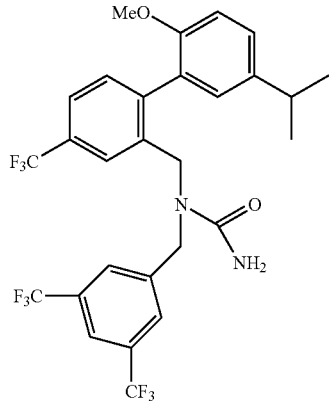 |
| Ex. 33 | 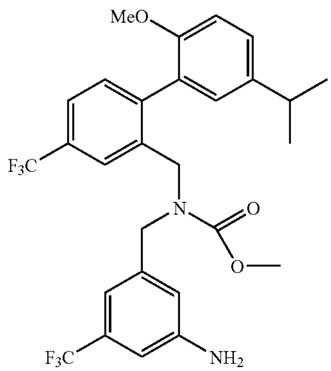 |
| Ex. 34 | 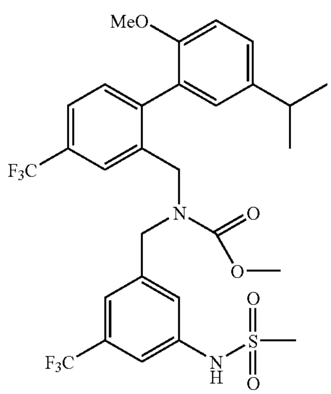 |
| Ex. 35 | 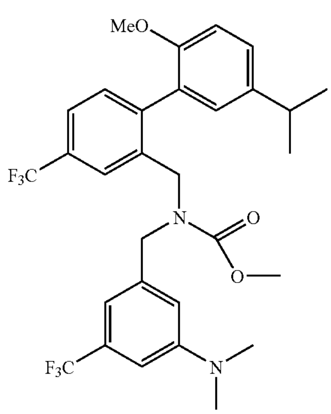 |
| Ex. 36 | |
| Ex. 37 | |
| Ex. 38 | |

TABLE 1-continued
| Example | Structure |
|---|---|
| Ex. 39 | 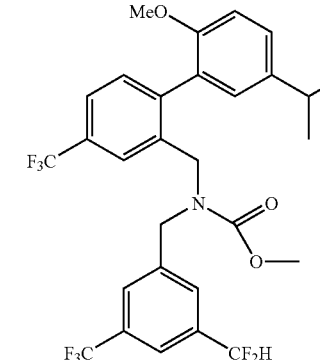 |
| Ex. 40 | 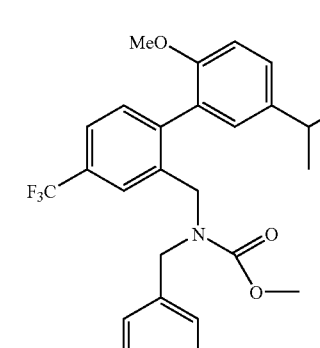 |
| Ex. 41 | 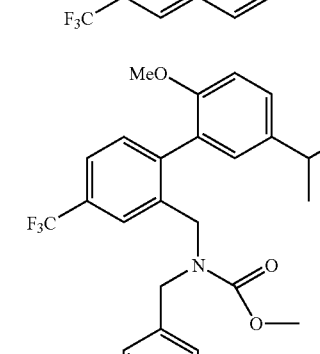 |
| Ex. 42 | 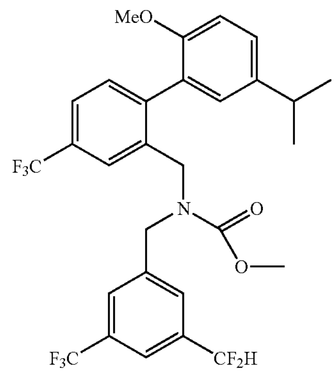 |
| Ex. 43 | 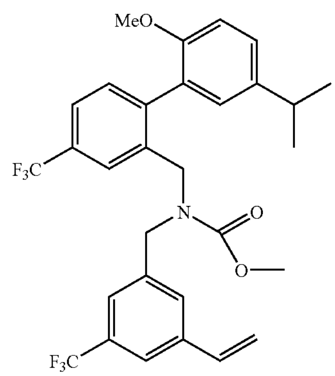 |
| Ex. 44 | 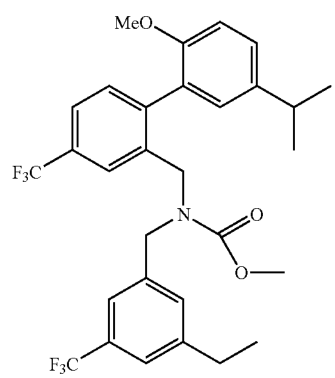 |
| Ex. 45 | 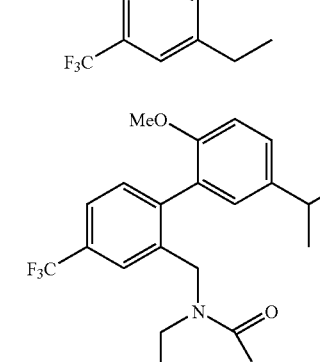 |

TABLE 1-continued
| Example | Structure |
|---|---|
| Ex. 46 | 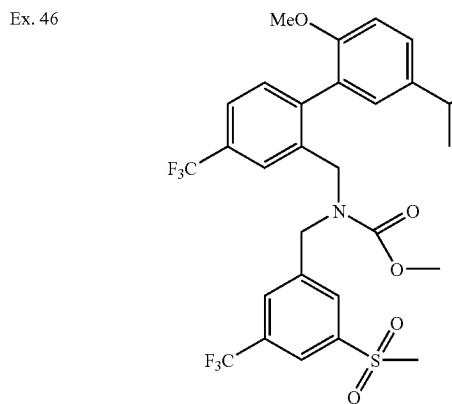 |
| Ex. 47 | 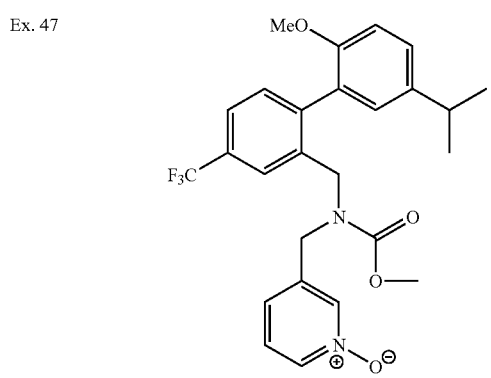 |
| Ex. 48 | 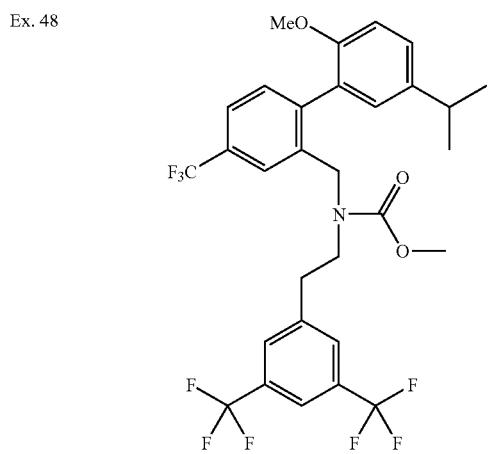 |
TABLE 1-continued
| Example | Structure |
|---|---|
| Ex. 134 | 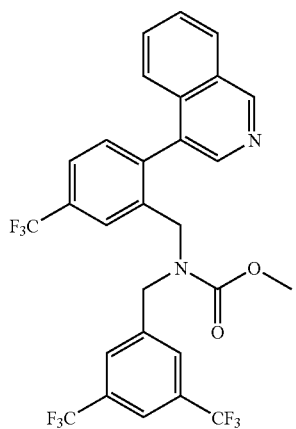 |
| Ex. 135 | 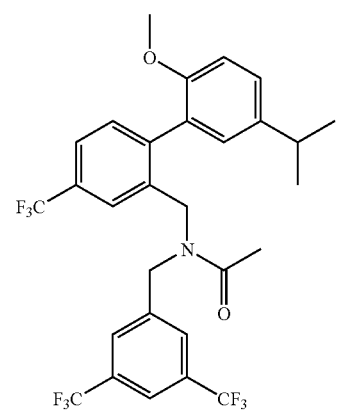 |
| Ex. 136 | 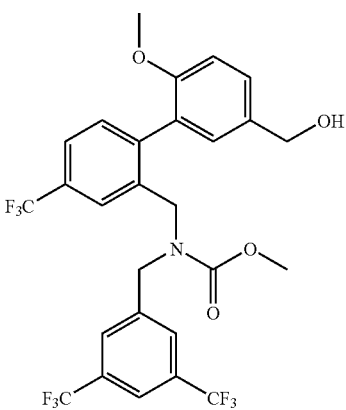 |

TABLE 1-continued
| Example | Structure |
|---|---|
| Ex. 137 | 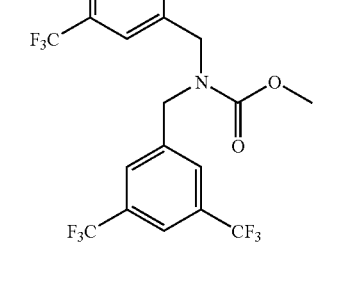 |
| Ex. 138 | 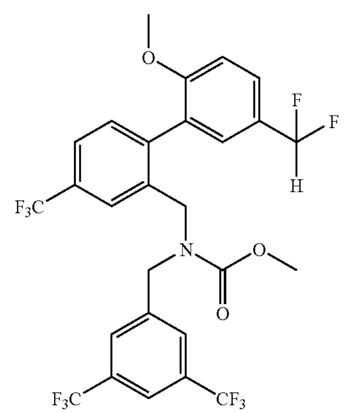 |
| Ex. 139 | |“
TABLE 1-continued
| Example | Structure |
|---|---|
| Ex. 140 | 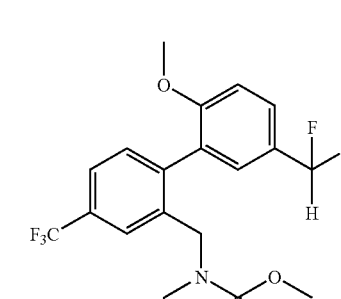 |
| Ex. 141 | 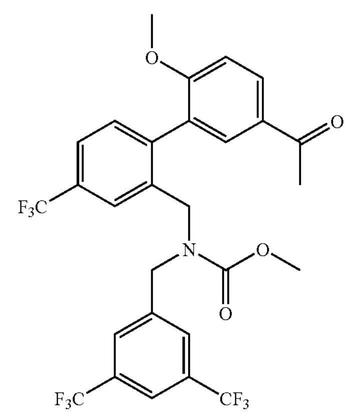 |
| Ex. 142 | 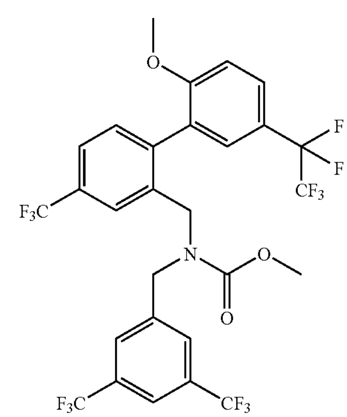 |

TABLE 1-continued

| Example | Structure |
|---------|-----------|
| Ex. 143 | |
| Ex. 144 | |
| Ex. 145 | |
| Ex. 146 | 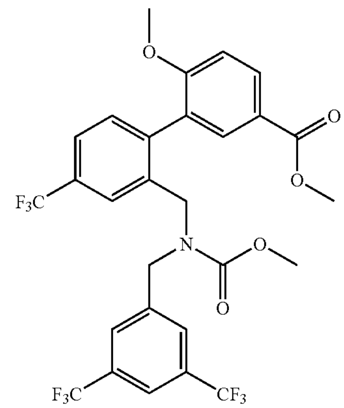 |
| Ex. 147 | 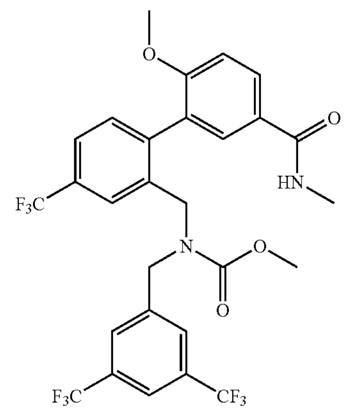 |
| Ex. 148 | 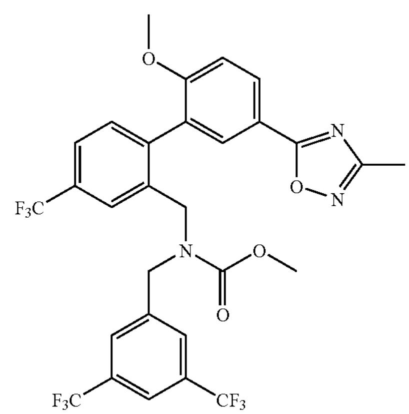 |
| Ex. 149 | 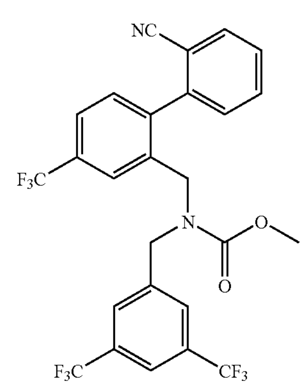 |

TABLE 1-continued

| Example | Structure |
| --- | --- |
| Ex. 150 | 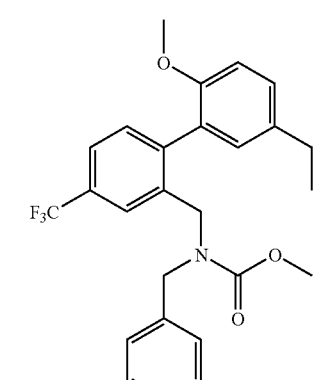 |

Definitions

"Ac" is acetyl, which is CH₃C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—CH₂—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocyclyl," "heterocycle," and "heterocyclic" means a fully or partially saturated or aromatic 5-6 membered ring containing 14 heteroatoms in the ring independently selected from N, S and O, unless otherwise stated. The heterocyclic ring may also be defined to include an optional carbonyl group or —N(O)— group as part of the ring structure. An example of the latter is pyridine N-oxide.

"Benzoheterocycle" represents a phenyl ring fused to a 5-6-membered heterocyclic ring having 1-2 heteroatoms, each of which is O, N, or S, where the heterocyclic ring may be saturated or unsaturated (i.e. the heterocyclic ring may have 1-2 double bonds in addition to the double bond of the phenyl ring). Examples include indole, 2,3-dihydroindole, benzofuran, 2,3-dihydrobenzofuran, quinoline, and isoquinoline. When the fused heterocycle is aromatic, the benzoheterocycle may also be referred to as benzoheteroaromatic or benzheteroaryl.

"Halogen" includes fluorine, chlorine, bromine and iodine. Halogen substituents are most often fluorine or chlorine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of the Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the crystalline forms of compounds of the present invention may exist as polymorphs, and as such are intended to be included in the present invention. In addition, some of the compounds of the instant invention may form solvates with water or common organic solvents. Such solvates and hydrates are likewise encompassed within the scope of this invention.

Some of the biphenyl and biaryl compounds herein are observed as mixtures of atropisomers (rotamers) in the NMR spectra. The individual atropisomers as well as the mixtures are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Prodrugs which yield compounds of Formula I in vivo in which Z is —$CO_2H$ are also compounds of this invention. Compounds of Formula I in which Z is —$CO_2H$ are generally unstable to make and use in pharmaceutical compositions.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, and diseases which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity and endotoxemia.

The compounds of this invention are expected to be particularly effective in raising HDL-C and/or increasing the ratio of HDL-C to LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, ZD4522 and other statins), (ii) bile acid sequestrants (cholestyramine, colestipol, and dialkylaminoalkyl derivatives of a cross-linked dextran), (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate and bezafibrate, (v) cholesterol absorption inhibitors, such as ezetimibe, (vi) acyl CoA:cholesterol acyltransferase (ACAT) inhibitors, such as avasimibe, (vii) phenolic anti-oxidants, such as probucol, and (viii) a microsomal triglyceride transfer protein (MTP)/ApoB secretion inhibitor.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations with atorvastatin, ezetimibe, or both compounds.

Finally compounds of this invention can be used with compounds that are useful for treating other disease, such as diabetes and obesity, as well as other anti-atherosclerostic compounds.

Examples of other active ingredients that may be administered in combination with a compound of this invention include, but are not limited to:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;
(c) protein tyrosine phosphatase-1B (PTP-1B) inhibitors,
(d) dipeptidyl peptidase IV (DP-IV) inhibitors;
(e) insulin or insulin mimetics;
(f) sulfonylureas, such as tolbutamide and glipizide, or related materials;
(g) α-glucosidase inhibitors (such as acarbose);
(h) agents which improve a patient's lipid profile, as described previously;
(i) PPARα/γ dual agonists, such as muraglitazar, tesaglitazar, farglitazar, and JT-501;
(j) PPARδ agonists such as those disclosed in WO97/28149;
(k) antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and β₃ adrenergic receptor agonists;
(l) ileal bile acid transporter inhibitors;
(m) agents intended for use in inflammatory conditions such as aspirin, non-steroidal anti-inflammatory drugs, glucocorticoids, azulfidine, and cyclo-oxygenase 2 selective inhibitors, including etoricoxib and rofecoxib;
(n) glucagon receptor antagonists;
(o) GLP-1,
(p) GIP-1, and
(q) GLP-1 analogs, such as exendins, for example exenitide.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

CETP Assay

An in vitro continuous assay for determining $IC_{50}$'s to identify compounds that are CETP inhibitors was performed based on a modification of the method described by Epps et al. employing BODIPY®-CE as the cholesteryl ester lipid donor. See Epps et al. (1995) Method for measuring the activities of cholesteryl ester transfer protein (lipid transfer protein), *Chem. Phys. Lipids.* 77, 51-63.

Particles used in the assay were created from the following sources: Synthetic donor HDL particles containing DOPC (Dioleoyl Phosphatidyl Choline), BODIPY®-CE (Molecular Probes C-3927), triolein (a triglyceride), and apoHDL were essentially created by probe sonication as described by Epps et al, but with the addition of a non-diffusable quencher molecule, dabcyl dicetylamide, in order to reduce background fluorescence. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat# 7205). An assay cocktail containing CETP, 1× CETP buffer (50 mM Tris, pH 7.4, 100 mM NaCl, 1 mM EDTA), and half the final concentration of acceptor particles was prepared, and 100 µL of the assay cocktail was added to each well of the plate. Test compounds in DMSO were added in a volume of 3 µL. The plate was mixed on a plate shaker and then incubated at 25° C. for 1 hour. A second assay cocktail containing donor particles, the remaining acceptor particles and 1× CETP buffer was prepared. 47 µL of the second assay cocktail was added to the reaction wells to start the assay. Assays were performed at 25° C. in a final volume of 150 µL. Final concentrations of materials were: 5 ng/µL donor particles, 30 ng/µL acceptor particles (each expressed by protein content), 1× CETP buffer, 0.8 nM recombinant human CETP (expressed in CHO cells and partially purified), and up to 2% DMSO when testing compounds. The assay was followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well.

Data was evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following examples are provided so that the invention will be more fully appreciated and understood. They should not be construed as limiting the invention in any way. The scope of the invention is defined by the appended claims. Examples 1-5, 15-18, 20, 21, 23-27, 49, and 50 are examples of synthetic intermediates. The remaining examples are compounds of the invention. Compounds of this invention have an $IC_{50}$ value as measured using the assay described above of less than or equal to 50 µM.

The following Schemes are provided to further teach how compounds that are not specifically disclosed herein can be synthesized by one of ordinary skill in the art. Starting materials are made using known procedures or as illustrated. Some starting materials may also be available for purchase.

SCHEME 1

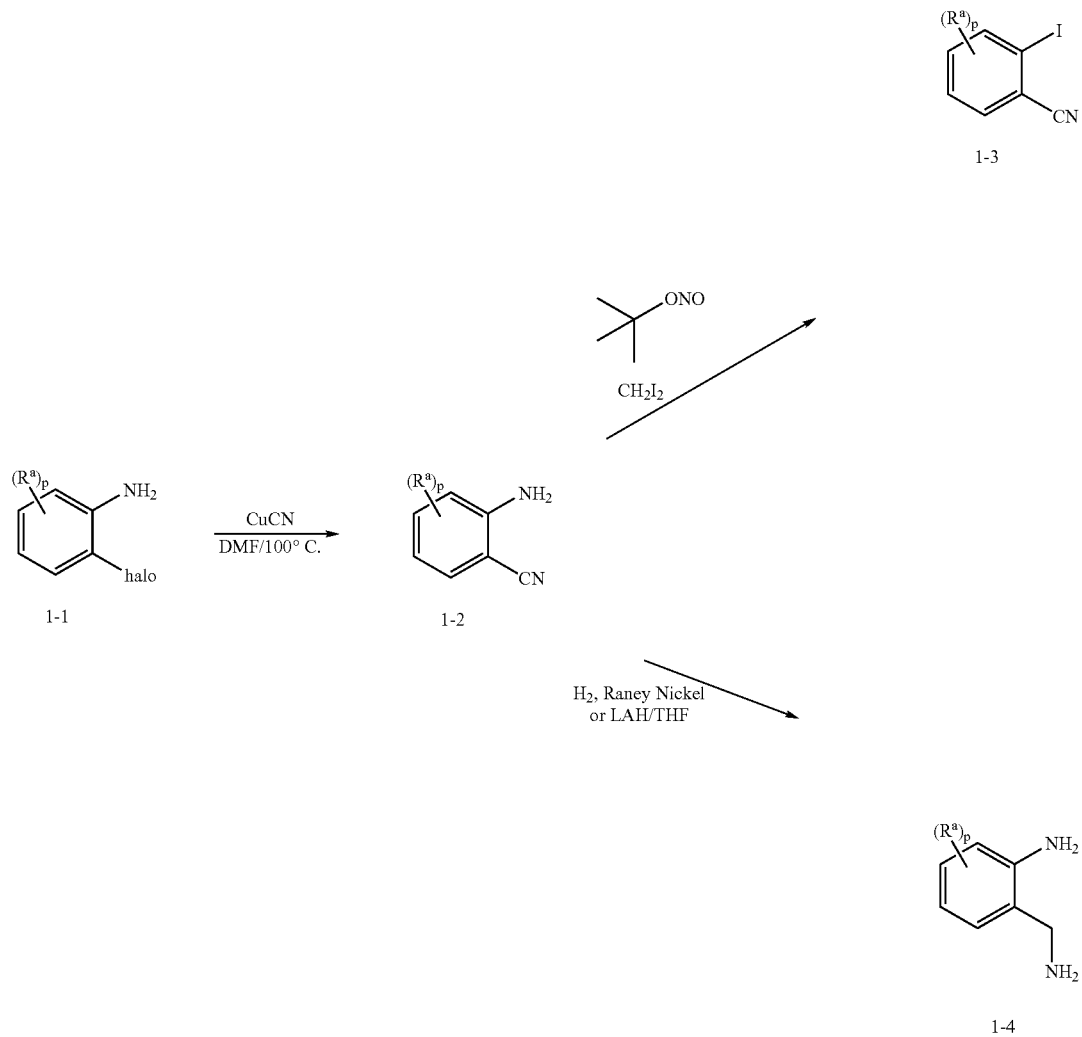

Intermediates 1-2, 1-3 and 1-4 utilized in the present invention can be purchased or prepared as shown in Scheme 1. An appropriately substituted 2-haloaniline wherein $R^a$ and p are as defined in the claims and where the halogen is preferably iodo or bromo is treated with CuCN in DMF at elevated temperature to afford the corresponding 2-cyanoaniline. Alternatively, the nitrite can be prepared by treatment of 1-1 with KCN and CuI in the presence of a palladium (II) salt or in the presence of certain copper or nickel complexes (See: Smith, M. B. and March, J. "March's Advanced Organic Chemistry", $5^{th}$ Ed., John Wiley and Sons, New York, pp. 867 (2001) and references therein). Iodides 1-3 are prepared by treatment of 1-2 with isoamylnitrite, n-pentylnitrite, t-butyl nitrite or the like in diiodomethane (see for example: Smith et al., *J. Org. Chem.* 55, 2543, (1990) and references cited therein). Alternatively, the iodide can be prepared first by diazonium formation using isoamylnitrite, n-pentylnitrite, t-butyl nitrite, sodium nitrite, nitrous acid or the like followed by heating in the presence of iodine or an iodide salt such as copper iodide, sodium iodide, potassium iodide, tetrabutylammonium iodide or the like. Reduction of nitrite 1-2 is carried out using Raney nickel under hydrogen atmosphere in water, methanol, ethanol or the like to afford 2-aminomethyl aniline 1-4. Alternatively, the nitrite can be reduced with Palladium on carbon under hydrogen atmosphere in methanol, ethanol or the like or with lithium aluminum hydride, lithium borohydride, borane or the like in ether, tetrahydrofuran, dimethoxyethane or the like to afford 1-4. Other methods for reduction of a nitrite to an aminomethyl group can be found in Smith, M. B. and March, J. "March's Advanced Organic Chemistry", $5^{th}$ Ed., John Wiley and Sons, New York, pp. 1204 (2001) and references therein.

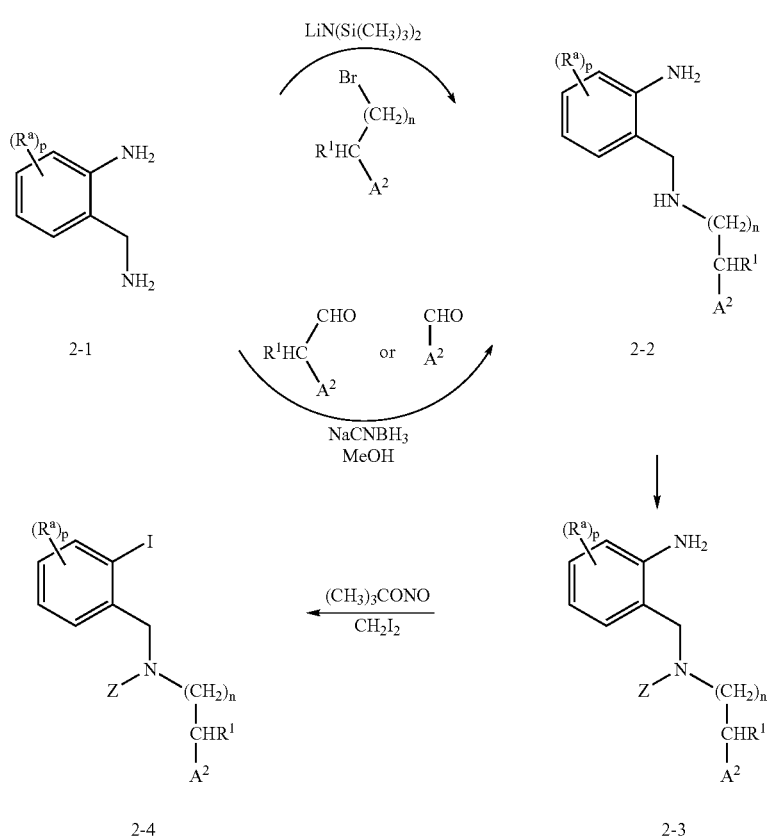

Intermediates 2-4 utilized in the present invention wherein $A^2$, $R^1$, $R^a$, Z, n and p are as defined in the claims can be prepared as shown in Scheme 2. Aminomethylaniline 2-1 can be purchased or prepared according to the procedure outlined in Scheme 1. Alkylation of 2-1 can be carried out by treatment with an appropriately substituted alkyl halide, mesylate or tosylate or the like in dichloromethane, dichloroethane, tetrahydrofuran, dimethoxyethane or the like in the presence of a base such as triethylamine, diisopropylethylamine, N-methylmorpholine, lithium diisopropylamide or lithium-, sodium-, or potassium bis(trimethylsilyl)amide or the like to afford disubstituted amine 2-2. Alternatively, treatment of amine 2-1 with an appropriately substituted aldehyde in the presence of a reducing agent such as sodium borohydride, sodium cyanoborohydride, sodium triacetoxyborohydride or the like in methanol, ethanol, dichloroethane, tetrahydrofuran or the like or according to methods described in Smith, M. B. and March, J. "March's Advanced Organic Chemistry", 5th Ed., John Wiley and Sons, New York, pp. 1187-1189 (2001) and references cited therein affords dialkylamine 2-2. Alternatively, amine 2-1 can be treated with an appropriately substituted carboxylic acid halide, carboxylic acid activated ester or carboxylic acid in the presence of a coupling reagent such as EDC, DCC, BOP, HATU or the like and a hindered base such as triethylamine, diisopropylethylamine, N-methyl morpholine or the like in a suitable solvent such as dichloromethane, dichloroethane, tetrahydrofuran, dimethoxyethane or the like to give the corresponding amide which can be reduced with LAH, borane or the like to afford dialkylamine 2-2. Acylation of 2-2 with a carboxylic acid and coupling reagent such as EDC EDC, DCC, BOP, HATU or the like, or a carboxylic acid activated ester or an acid halide, alkylchloroformate, alkylisocyanate, alkylsulfonyl chloride, chlorosulfonyl isocyanate or the like in dichloromethane, dichloroethane, tetrahydrofuran, dimethoxyethane or the like in the presence of a hindered base such as triethylamine, diisopropylethylamine, N-methylmorpholine, pyridine or the like affords 2-3. Iodide 2-4 can be prepared by treatment of 2-3 with isoamylnitrite, n-pentylnitrite, t-butyl nitrite or the like in diiodomethane (see for example: Smith et al., *J. Org. Chem.* 55, 2543, (1990) and references cited therein). Alternatively, the iodide can be prepared first by diazonium formation using isoamylnitrite, n-pentylnitrite, t-butyl nitrite, sodium nitrite, nitrous acid or the like followed by heating in the presence of iodine or an iodide salt such as copper iodide, sodium iodide, potassium iodide, tetrabutylammonium iodide or the like.

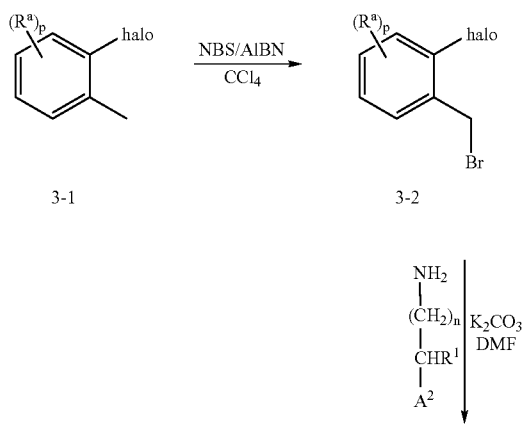

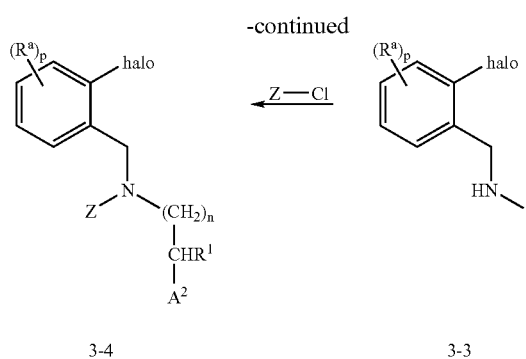

3-4        3-3

Haloaryl intermediates 3-4 of the present invention wherein $A^2$, $R^1$, $R^a$, Z, n and p are as defined in the claims can be prepared as shown in scheme 3. 2-halobenzylbromides 3-2 wherein the halo is preferably iodo or bromo can be purchased or prepared from 2-halotoluenes via benzylic bromination using N-bromosuccinimide in carbon tetrachloride. Treatment of 3-2 with an appropriately substituted benzylamine affords dialkyl amine 3-3. Acylation of 3-3 with a carboxylic acid and coupling reagent such as EDC EDC, DCC, BOP, HATU or the like, or a carboxylic acid activated ester or an acid halide, alkylchloroformate, alkylisocyanate, alkylsulfonyl chloride, chlorosulfonyl isocyanate or the like in dichloromethane, dichloroethane, tetrahydrofuran, dimethoxyethane or the like in the presence of a hindered base such as triethylamine, diisopropylethylamine, N-methylmorpholine, pyridine or the like affords 3-4.

SCHEME 4

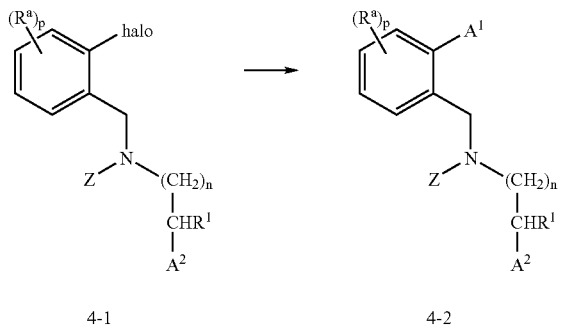

4-1        4-2

Biaryl compounds 4-2 of the present invention wherein $A^1$, $A^2$, $R^1$, $R^a$, Z, n and p are as defined in the claims can be prepared from aryl halide 4-1 where the halide is preferably bromo or iodo via a Suzuki or Stille reaction wherein 4-1 is coupled with an appropriately substituted aryl boronic acid, aryl boronate ester or aryl trialkyl tin in the presence of a palladium catalyst. The coupling reaction may be carried out using Pd(II)acetate and potassium carbonate in aqueous acetone at reflux. Alternatively the reaction may employ tetrakis(triphenylphosphine)palladium in an ethanol/toluene mix in the presence of sodium carbonate. Alternatively, as practiced by those skilled in the art the reaction can employ a number of Palladium (0) compounds and Palladium (II) salts in a number of solvents and in the presence of a variety of ligands, bases, and promoters, generally but not exclusively, with heating and/or microwave irradiation. Some appropriate reaction conditions can be found described in Miyaua et al., *Chem. Rev.* 95, 2457 (1995) and references cited within and as described in Smith, M. B. and March, J. "March's Advanced Organic Chemistry", 5$^{th}$ Ed., John Wiley and Sons, New York, pp. 868-869 (2001) and references cited therein. Compounds 4-1 are prepared as shown in Schemes 2 and 3.

SCHEME 5

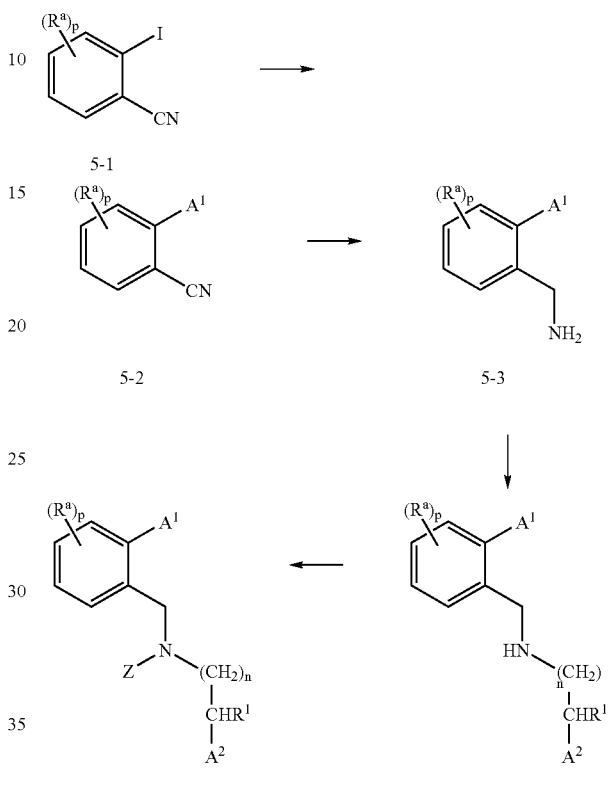

Compounds of the present invention wherein $A^1$, $A^2$, $R^1$, $R^a$, Z, n and p are as defined in the claims can be prepared as shown in Scheme 5. 2-cyano iodobenzenes 5-1 can be purchased or prepared according to the procedures outlined in Scheme 1. Biphenyl compounds 5-2 are prepared via a Suzuki or Stille reaction or variation thereof employing palladium catalyzed cross coupling of iodide 5-1 with an appropriately substituted aryl boronic acid, aryl boronate ester or aryl trialkyl tin as described in Miyaua et al., *Chem. Rev.* 95, 2457 (1995) and references cited within and as described in Smith, M. B. and March, J. "March's Advanced Organic Chemistry", 5$^{th}$ Ed., John Wiley and Sons, New York, pp. 868-869 (2001) and references cited therein. Reduction of nitrile 5-2 is accomplished with Lithium aluminum hydride in diethyl ether to afford 2-aminomethyl aniline 5-3. Alternatively, the nitrile can be reduced with Palladium on carbon or Raney nickel under hydrogen atmosphere in methanol, ethanol or the like. Other methods for reduction of a nitrile to an aminomethyl group can be found in Smith, M. B. and March, J. "March's Advanced Organic Chemistry", 5$^{th}$ Ed., John Wiley and Sons, New York, pp. 1204 (2001) and references therein. Alkylation of 5-3 is achieved by treatment with an appropriately substituted benzyl halide, mesylate or tosylate or the like in dichloromethane, dichloroethane, tetrahydrofuran, dimethoxyethane or the like in the presence of a base such as triethylamine, diisopropylethylamine, N-methylmorpholine, lithium diisopropylamide or lithium-, sodium-, or potassium bis(trimethylsilyl)amide or the like to afford disubstituted amine 5-4. Alternatively, treatment of amine 5-3 with an appropriately substituted aldehyde in the presence of a reducing agent such as sodium borohydride, sodium cyanoborohydride, sodium triacetoxyborohydride or the like in methanol, ethanol, dichloroethane, tetrahydrofuran or the like or according to methods described in Smith, M. B. and March, J. "March's Advanced Organic Chemistry", $5^{th}$ Ed., John Wiley and Sons, New York, pp. 1187-1189 (2001) and references cited therein affords disubstituted amine 5-4. Alternatively, amine 5-3 can be treated with an appropriately substituted carboxylic acid halide, carboxylic acid activated ester or carboxylic acid in the presence of a coupling reagent such as EDC, DCC, BOP, HATU or the like and a hindered base such as triethylamine, diisopropylethylamine, N-methyl morpholine or the like in a suitable solvent such as dichloromethane, dichloroethane, tetrahydrofuran, dimethoxyethane or the like to give the corresponding amide which can be reduced with LAH, borane or the like to afford disubstituted amine 5-4. Acylation of 5-4 with a carboxylic acid and coupling reagent such as EDC EDC, DCC, BOP, HATU or the like, or a carboxylic acid activated ester or an acid halide, alkylchloroformate, alkylisocyanate, alkylsulfonyl chloride, chlorosulfonyl isocyanate or the like in dichloromethane, dichloroethane, tetrahydrofuran, dimethoxyethane or the like in the presence of a hindered base such as triethylamine, diisopropylethylamine, N-methylmorpholine, pyridine or the like affords 5-5.

aqueous potassium hydroxide or the like in the presence of protic solvents such as isopropanol to afford the benzoic acid 6-2. Reduction to the benzyl alcohol 6-3 can be achieved with borane in tetrahydrofuran as described in Smith, M. B. and March, J. "March's Advanced Organic Chemistry", $5^{th}$ Ed., John Wiley and Sons, New York, pp. 1549 (2001) and references therein. Conversion of alcohol 6-3 to bromide 6-4 can be achieved with carbon tetrabromide and triphenylphosphine in dichloromethane (see for example: Iwasaki et al., *Tetrahedron*, 52, 13327 (1996) and references cited therein). Treatment of 6-4 with an appropriately substituted amine followed by acylation with a carboxylic acid and coupling reagent such as EDC EDC, DCC, BOP, HATU or the like, or a carboxylic acid activated ester or an acid halide, alkylchloroformate, alkylisocyanate, alkylsulfonyl chloride, chlorosulfonyl isocyanate or the like in dichloromethane, dichloroethane, tetrahydrofuran, dimethoxyethane or the like in the presence of a hindered base such as triethylamine, diisopropylethylamine, N-methylmorpholine, pyridine or the like affords 6-5.

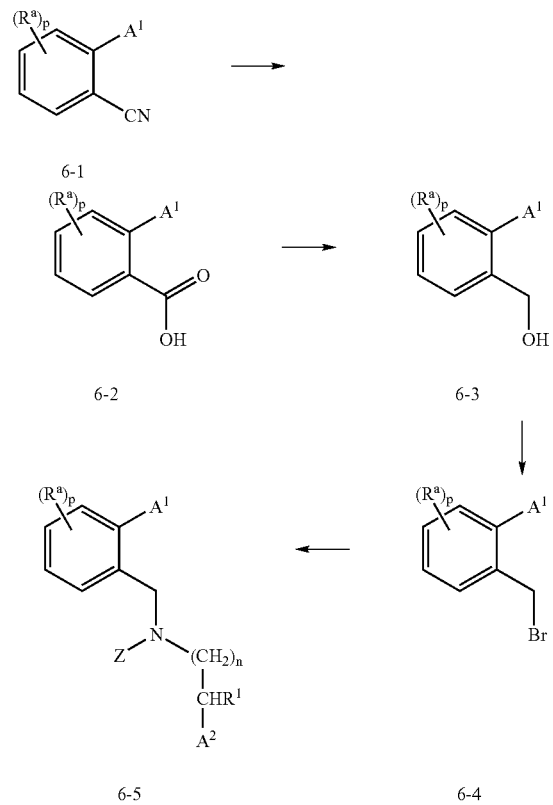

SCHEME 6

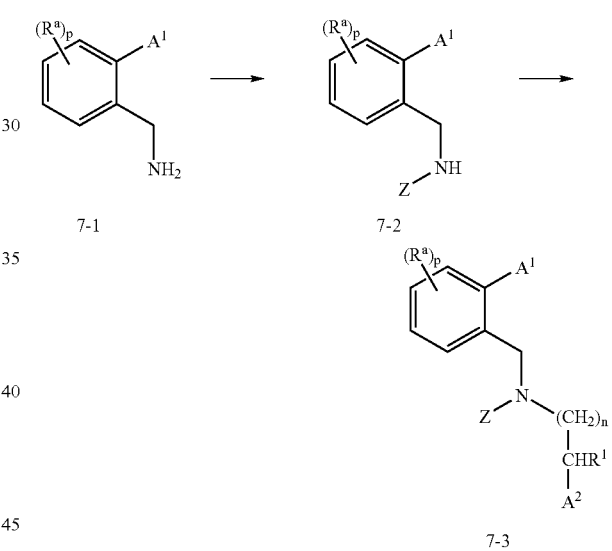

SCHEME 7

Compounds of the present invention wherein $A^1$, $A^2$, $R^1$, $R^a$, Z, n and p are as defined in the claims can be prepared by the procedure described in Scheme 6. Base mediated hydrolysis of 2-cyanobenzenes 6-1 can be achieved by treatment with Compounds of the present invention wherein $A^1$, $A^2$, $R^1$, $R^a$, Z, n and p are as defined in the claims can be prepared by acylation of benzylamine 7-1 with a carboxylic acid and coupling reagent such as EDC EDC, DCC, BOP, HATU or the like, or a carboxylic acid activated ester or an acid halide, alkylchloroformate, alkylisocyanate, alkylsulfonyl chloride, chlorosulfonyl isocyanate or the like in dichloromethane, dichloroethane, tetrahydrofuran, dimethoxyethane or the like in the presence of a hindered base such as triethylamine, diisopropylethylamine, N-methylmorpholine, pyridine or the like affords 7-2. Alkylation of 7-2 can be carried out by treatment with an appropriately substituted alkyl halide, mesylate or tosylate or the like in dichloromethane, dichloroethane, tetrahydrofuran, dimethoxyethane or the like in the presence of a base such as triethylamine, diisopropylethylamine, N-methylmorpholine, lithium diisopropylamide or lithium-, sodium-, or potassium bis(trimethylsilyl)amide or the like to afford compounds 7-3.

SCHEME 8

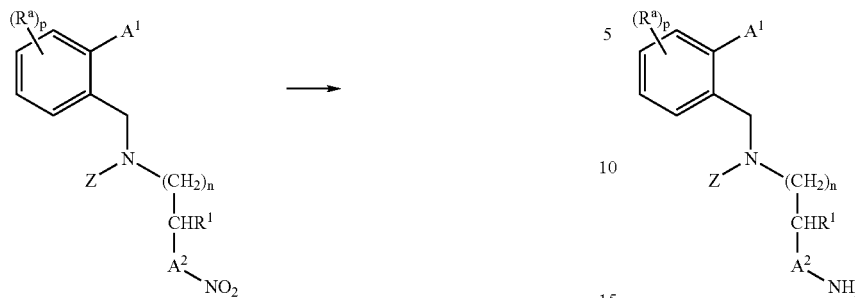

8-1

8-2

8-3

SCHEME 9

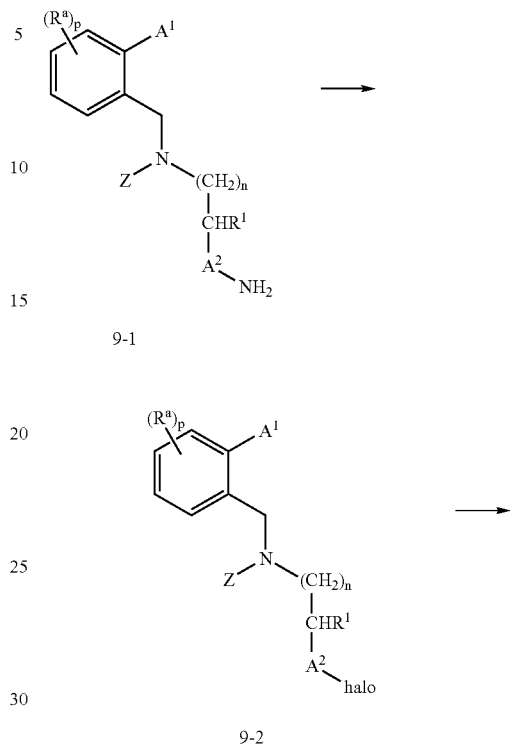

9-1

9-2

9-3

Compounds of the present invention wherein $A^1$, $A^2$, $R^1$, $R^a$, Z, n and p are as defined in the claims can be prepared as shown in scheme 8. Nitro compounds 8-1 can be reduced with catalysts such as platinum oxide and the like under a hydrogen atmosphere in solvents such as tetrahydrofuran and the like to afford aryl amines 8-2. Acylation of amine 8-2 with an acid chloride, alkylchloroformate, sulfonyl chloride, alkylisocyanate or the like in dichloromethane, dichloroethane, tetrahydrofuran, dimethoxyethane or the like in the presence of a hindered base such as triethylamine, diisopropylethylamine, N-methyl morpholine, pyridine or the like affords compounds 8-3. Alternatively, alkylation of aniline 8-2 with an alkyl halide, mesylate or tosylate or the like in the presence of organic bases such as potassium hexamethyldisilazide and the like in solvents such as tetrahydrofuran, diethyl ether and the like affords compounds 8-3.

Compounds of the present invention wherein $A^1$, $A^2$, $R^1$, $R^a$, Z, n and p are as defined in the claims can be prepared as shown in scheme 9. Aryl amine 9-1 can be converted to the corresponding aryl iodide 9-2 by treatment with isoamylnitrite, n-pentylnitrite, t-butyl nitrite or the like in diiodomethane (see for example: Smith et al., *J. Org. Chem.* 55, 2543, (1990) and references cited therein). Alternatively, the iodide can be prepared first by diazonium formation using isoamylnitrite, n-pentylnitrite, t-butyl nitrite, sodium nitrite, nitrous acid or the like followed by heating in the presence of iodine or an iodide salt such as copper iodide, sodium iodide, potassium iodide, tetrabutylammonium iodide or the like to afford compounds 9-1. Compounds 9-2 can be converted to compounds 9-3 via Suzuki or Stille reaction by coupling with an appropriately substituted aryl boronic acid, aryl boronate ester or aryl trialkyl tin in the presence of a palladium catalyst (see for example: Miyaua et al., *Chem Rev.* 95, 2457 and references cited therein).

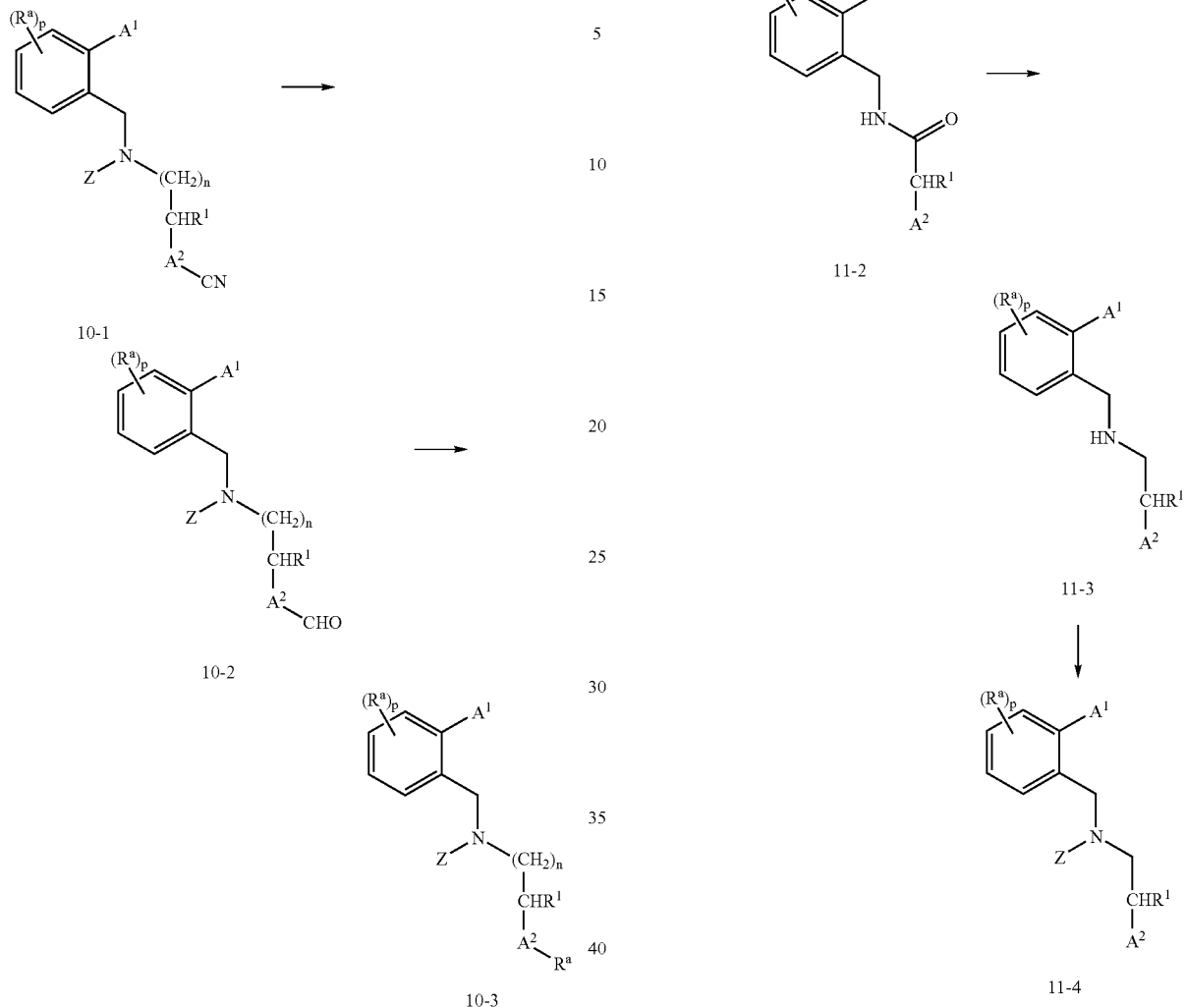

Compounds of the present invention wherein $A^1$, $A^2$, $R^1$, $R^a$, Z, n and p are as defined in the claims can be prepared as shown in scheme 10. Treatment of nitrites 10-1 with aqueous formic acid in the presence of catalysts such as platinum oxide and the like affords aldehyde 10-2 which can be further modified by reaction with organophosphorane reagents such as methyltriphenylphosphonium bromide as described in Smith, M. B. and March, J. "March's Advanced Organic Chemistry", 5$^{th}$ Ed., John Wiley and Sons, New York, pp. 1231-1237 (2001) to give compounds 10-3.

Phenethyl substituted compounds 11-4 of the present invention can be prepared as described in scheme 11. Intermediate 11-2 can be prepared by treating benzylamine 11-1 with a appropriately substituted phenyl acetic acid halide, phenyl acetic acid activated ester or phenyl acetic acid in the presence of a coupling reagent such as EDC, DCC, BOP, HATU or the like in a suitable solvent such as dichloromethane, dichloroethane and the like. Amide 11-2 can be reduced with lithium aluminum hydride, borane or the like in ether, tetrahydrofuran or the like to afford 11-3. Acylation of 11-3 with an acid chloride, alkyl chloroformate, alkyl isocyanate or the like in dichloromethane, dichloroethane, tetrahydrofuran, dimethoxyethane or the like affords compounds 11-4.

Example 1

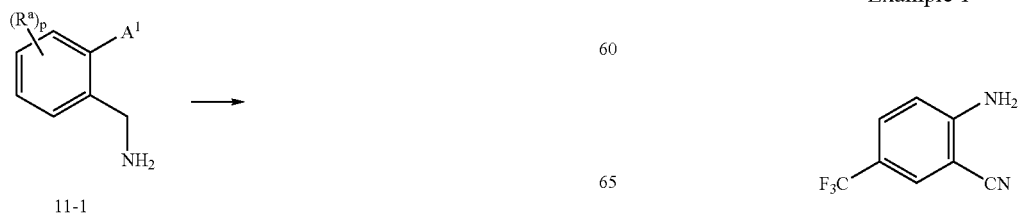

2-Amino-5-(trifluoromethyl)benzonitrile

In a 2-liter flask equipped with a septum inlet, magnetic stirring bar, and condenser leading to a mercury bubbler was placed 100 g (0.348 mol) of 4-amino-3-iodobenzotrifluoride in 1 liter DMF. To this reaction flask with stirring was added 37.4 g (0.416 mol) of copper cyanide and the contents were heated to 100° C. under nitrogen for fourteen hours. Afterwards, TLC analysis revealed minor starting material (20/80) ethyl acetate/hexane. The contents were cooled to 40° C. and filtered through a pad of Celite. The solids were washed with ether and the filtrate transferred to a separatory funnel and washed with about 5% aqueous ammonium hydroxide. The aqueous layer was back-extracted with ether and the organics were combined and washed with brine, dried over magnesium sulfate, filtered and concentrated to yield a black oil. The oil was chromatographed on a Biotage 75L cartridge with ethyl acetate/hexane to obtain 68 g 2-amino-5-(trifluoromethyl)benzonitrile as a black solid.

Example 2

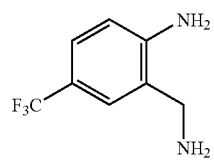

[2-(Aminomethyl)-4-(trifluoromethyl)phenyl]amine

In a rocker shaker was charged 37 g (0.2 mol) of 2-amino-5-(trifluoromethyl)benzonitrile in 500 mL of ethanol and 76 mL of ammonium hydroxide. The contents were degassed/blanketed with nitrogen, 25 g of Raney nickel were added, then the shaker was pressurized with 40 psi hydrogen gas. At 15 hours TLC analysis (20/80 ethyl acetate/hexane) revealed no starting material. The contents were filtered through Celite and washed with ether and concentrated to 37 g black oil. The oil was chromatographed on a Biotage 75L cartridge with methanol/methylene chloride and ammonium hydroxide/methanol/methylene chloride to give [2-(aminomethyl)-4-(trifluoromethyl)phenyl]amine as a green oil.

Example 3

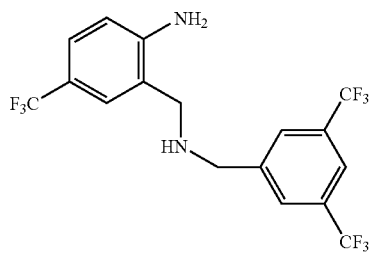

[2-Amino-5-(trifluoromethyl)benzyl][3,5-bis(trifluoromethyl)benzyl]amine

In a 500-mL flask equipped with a septum inlet, magnetic stirring bar, and condenser leading to a mercury bubbler was placed 22.8 g (0.12 mol) of [2-(aminomethyl)4-(trifluoromethyl)phenyl]amine in 218 mL dimethoxyethane. To this reaction flask with stirring was added 26 mL (0.24 mol) N-methylmorpholine and 24 mL (0.13 mol) 3,5-bis(trifluoromethyl)benzyl bromide. The contents were heated to and maintained at reflux under nitrogen for 12 hours. Afterwards, TLC analysis revealed a minor amount of starting material remaining. The contents were cooled to room temperature, diluted with ether and transferred to a separatory funnel and washed with water and brine, dried over magnesium sulfate, filtered and concentrated to afford an oil. The oil was dissolved in hexane, cooled in an ice bath and acetic acid was added slowly while stirring to precipitate solids. The solids were filtered, dissolved in ether, and cooled in an ice bath and stirred while saturated sodium bicarbonate was added slowly until basic. The contents were transferred to a separatory funnel and washed with brine, dried over magnesium sulfate, filtered, and concentrated to give 12 g [2-amino-5-(trifluoromethyl)benzyl][3,5-bis(trifluoromethyl)benzyl]amine as an orange oil. In addition the hexane mother liquor contained significant amounts of product and byproducts. This liquor was concentrated to yield dark yellow oil that was used without further purification in the following step.

Example 4

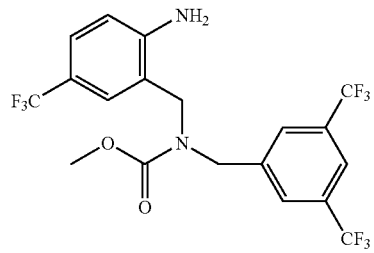

Methyl [2-amino-5-(trifluoromethyl)benzyl][3,5-bis(trifluoromethyl)benzyl]carbamate In a 250-mL flask equipped with a septum inlet, magnetic stirring bar, and connecting tube leading to a mercury bubbler was placed 12 g (0.029 mol) of [2-amino-5-(trifluoromethyl)benzyl][3,5-bis(trifluoromethyl)benzyl]amine in 120 mL DME. To the reaction flask with stirring was added 6.4 mL (0.058 mol) N-methylmorpholine and the mixture was cooled in an ice bath under nitrogen. To this mixture was added dropwise over ten minutes, 2.7 mL (0.035 mol) of methyl chloroformate. Afterwards, the mixture was allowed to stir for 15 minutes and HPLC showed no starting material present. Water was added to the mixture and the contents were diluted with hexane and transferred to a separatory funnel. The layers were separated, then washed with brine, dried over magnesium sulfate, filtered and concentrated to give 13 g crude oil. The oil was chromatographed on a Biotage 40M cartridge with methylene chloride/hexane to give methyl [2-amino-5-(trifluoromethyl)benzyl][3,5-bis(trifluoromethyl)benzyl]carbamate as a yellow oil.

Example 5

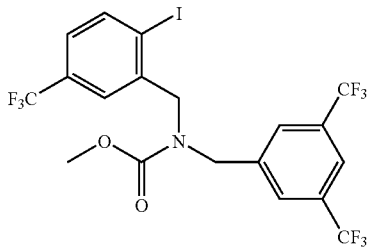

Methyl [3,5-bis(trifluoromethyl)benzyl][2-iodo-5-(trifluoromethyl)benzyl]carbamate In a 250-mL flask equipped with a septum inlet, magnetic stirring bar, and condenser leading to a mercury bubbler was placed 9 g (0.019 mol) of methyl [2-amino-5-(trifluoromethyl)benzyl][3,5-bis(trifluoromethyl)benzyl]carbamate in 90 mL $CHCl_3$. To this stirred solution was added 3.6 mL (0.027 mol) of isoamyl nitrite (tech. grade). The mixture was stirred at room temperature for 5 minutes under a nitrogen blanket. To this was added 9.7 g (0.038 mol) of iodine and the mixture was heated to and maintained at reflux for 2 hrs. The mixture was cooled and diluted with methylene chloride, transferred to a separatory funnel and washed with saturated aqueous sodium thiosulfate and brine; dried over magnesium sulfate, filtered, concentrated and chromatographed on a Biotage 40M cartridge with methylene chloride/hexane to give methyl [3,5-bis(trifluoromethyl)benzyl][2-iodo-5-(trifluoromethyl)benzyl]carbamate.

Example 6

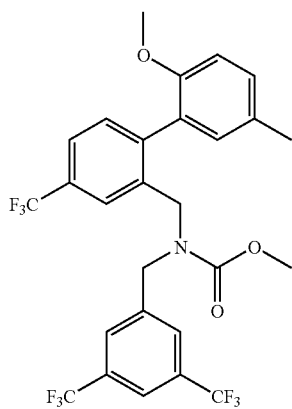

Methyl [3,5-bis(trifluoromethyl)benzyl]{[2'-methoxy-5'-methyl-4-(trifluoromethyl)biphenyl-2-yl]methyl}carbamate A mixture of methyl [3,5-bis(trifluoromethyl)benzyl][2-iodo-5-(trifluoromethyl)benzyl]carbamate (0.10 g, 0.17 mmol) from Example 5, and 2-methoxy-5-methylphenyl boronic acid (0.034 g, 0.2 mmol), palladium acetate (0.0038 g, 0.017 mmol) and potassium carbonate (0.047 g, 0.34 mmol) in 4:1 acetone/water (10 ml) was heated and maintained at reflux for 1 h. The color of the solution turned dark. Acetone was removed and the residue was extracted with methylene chloride (3×10 ml). The combined organic layers were washed with water, then brine, and dried over sodium sulfate. The title compound was obtained as a colorless oil by preparative thin layer chromatography using acetone/hexane (5:95) as the eluant. $^1H$ NMR ($CDCl_3$, 500 MHz): δ 7.73 (s, 1H), 7.58 (d, J=8.5 Hz, 1H), 7.47 (s, 2H), 7.35 (m, 1H), 7.32 (d, J=8.0 Hz, 1H), 7.19 (m, 1H), 6.85 (m, 2H), 4.23-4.36 (m, 4H), 3.79 (m, 3H), 3.68 (s, 3H), 2.25 (s, 3H). LC-MS (M+1): 580.0 (4.61 min).

Example 7

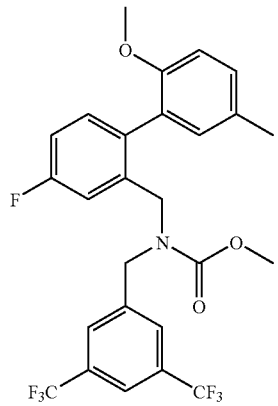

Methyl [3,5-bis(trifluoromethyl)benzyl][(4-fluoro-2'-methoxy-5'-methylbiphenyl-2-yl)methyl]carbamate Step A: [3,5-Bis(trifluoromethyl)benzyl](2-bromo-5-fluorobenzyl)amine To a solution of 2-bromo-5-fluoro benzyl bromide (0.5 g, 1.86 mmol) and 3,5-bis(trifluoromethyl)benzylamine (0.45 g, 1.86 mmol) in methylene chloride (10 ml) at 0° C., triethyl amine (0.39 ml, 2.80 mmol) was added. The solution was slowly warmed to room temperature and stirred for 18 h. The solvent was removed under reduced pressure. The title compound was obtained by flash column chromatography using EtOAc/hexane (2:8) as the eluant. $^1H$ NMR ($CDCl_3$, 500 MHz) δ 7.88 (s, 2H), 7.80 (s, 1H), 7.53 (dd, J=8.8, 5.3 Hz, 1H), 7.18 (dd, J=9, 3.3 Hz, 1H), 6.91 (dt, J=8.5, 3.3 Hz, 1H), 3.98 (s, 2H), 3.90 (s, 2H).

Step B: Methyl [3,5-bis(trifluoromethyl)benzyl](2-bromo-5-fluorobenzyl)carbamate To a solution of [3,5-bis(trifluoromethyl)benzyl](2-bromo-5-fluorobenzyl)amine from Step A (0.14 g) in methylene chloride at room temperature, excess methyl chloroformate (0.1 ml) and triethyl amine (0.1 ml) were added. The solution was stirred at room temperature for 2 h and the solvent was removed under reduced pressure. The title compound was obtained by flash column chromatography using EtOAc/hexane (1:9) as the eluant. $^1H$ NMR ($CDCl_3$, 500 MHz) δ 7.80 (s, 1H), 7.68 (s, 1H), 7.60 (s, 1H), 7.48 (m, 1H), 6.88 (m, 2H), 4.60 (m, 4H), 3.81 (s, 3H).

Step C: Methyl [3,5-bis(trifluoromethyl)benzyl][(4-fluoro-2'-methoxy-5'-methylbiphenyl-2-yl)methyl]carbamate A mixture of the Methyl [3,5-bis(trifluoromethyl)benzyl](2-bromo-5-fluorobenzyl)carbamate from Step B (0.02 g, 0.04 mmol), potassium carbonate (0.01 g, 0.08 mmol), 2-methoxy-5-methyl phenyl boronic acid (0.008 g, 0.05 mmol) and catalytic amount of palladium acetate (1 mg) in 4:1 acetone/water (2.5 ml) was heated to and maintained at reflux for 1 h. TLC analysis (acetone/hexane=5:95) showed no starting material. The solvent was removed under reduced pressure and the residue was extracted with methylene chloride (3×10 ml). The combined organic layers were washed with brine and dried over sodium sulfate. The title compound was obtained by preparative thin layer chromatography using acetone:hexane (5:95) as the eluant. $^1$H NMR (CDCl$_3$, 500 MHz) δ 7.75 (s, 1H), 7.50 (s, 1H), 7.38 (s, 1H), 7.20 (m, 2H), 7.04 (m, 2H), 6.84 (s, 1H), 6.80 (m, 1H), 4.18-4.60 (m, 4H), 3.80 (s, 3H), 3.68 (s, 3H), 2.32 (s, 3H). LC-MS (M+1) 530.4 (4.43 min).

Example 8

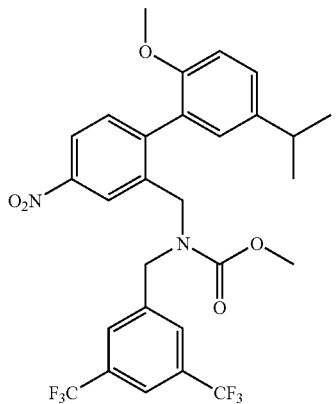

Methyl [3,5-bis(trifluoromethyl)benzyl][(5'-isopropyl-2'-methoxy-4-nitrobiphenyl-2-yl)methyl]carbamate Step A: (2-Bromo-5-nitrophenyl)methanol To a solution of methyl 2-bromo-5-nitro benzoate (0.52 g, 2.00 mmol) in THF (10 ml) at 0° C., a 1.0 M solution of DIBAL in THF (2.4 ml, 2.4 mmol) was added dropwise. The mixture was stirred at 0° C. for 4 h. The reaction was quenched with water extracted with ethyl acetate (3×20 ml). The combined organic layers were washed with brine, and dried over sodium sulfate. The title compound was obtained as a white solid following flash column chromatography using 8:92 EtOAc/hexane as the eluant. $^1$H NMR (CDCl$_3$, 500 MHz) δ 8.46 (d, J=2.5 Hz, 1H), 8.05 (dd, J=8.5, 3.0 Hz, 1H), 7.74 (d, J=8.5 Hz, 1H), 4.84 (s, 2H).

Step B: 2-Bromo-5-nitrobenzyl methanesulfonate

To a solution of the (2-bromo-5-nitrophenyl)methanol from Step A (0.33 g, 1.42 mmol) in methylene chloride (20 ml) at 0° C., methanesulfonyl chloride (0.13 ml, 1.70 mmol) and triethylamine (0.3 ml, 2.1 mmol) were added. The solution was stirred at 0° C. for 1 h. The reaction was diluted with methylene chloride (30 ml). The solution was washed with water, brine, and dried over sodium sulfate. The title compound was obtained by flash column chromatography using 10:90 EtOAc/hexane as the eluant. $^1$H NMR (CDCl$_3$, 500 MHz) δ 8.40 (d, J=2.5 Hz, 1H), 8.17 (dd, J=8.5, 3.0 Hz, 1H), 7.82 (d, J=8.5 Hz, 1H), 5.40 (s, 2H), 3.20 (s, 3H).

Step C: [3,5-bis(trifluoromethyl)benzyl](2-bromo-5-nitrobenzyl)amine

To a solution of 2-bromo-5-nitrobenzyl methanesulfonate from Step B (0.42 g, 1.35 mmol) and 3,5-bis-trifluoromethyl benzylamine (0.33 g, 1.35 mmol) in DMF (10 ml) at 0° C., potassium carbonate (0.37 g, 2.69 mmol) was added. The mixture was stirred at 0° C. for 2 h. TLC analysis (EtOAc/hexane=2:8) showed completion of the reaction. Water (50 ml) was added. The mixture was extracted with EtOAc (3×40 ml). The combined organic layers were washed with brine, and dried over sodium sulfate. The title compound was obtained by flash column chromatography using 2:8 EtOAc/hexane as the eluant. $^1$H NMR (CDCl$_3$, 500 MHz) δ 8.35 (d, J=2.5 Hz, 1H), 8.03 (dd, J=8.5, 2.5 Hz, 1H), 7.88 (s, 2H), 7.81 (s, 1H), 8.76 (d, J=8.5 Hz, 1H), 4.00 (s, 4H).

Step D: Methyl [3,5-bis(trifluoromethyl)benzyl](2-bromo-5-nitrobenzyl)carbamate

To a solution of [3,5-bis(trifluoromethyl)benzyl](2-bromo-5-nitrobenzyl)amine from Step C (0.47 g, 1.0 mmol) in methylene chloride (20 ml) at room temperature, methyl chloroformate (0.12 ml, 1.54 mmol) and triethylamine (0.29 ml, 2.05 mmol) were added. The solution was stirred at room temperature for 18 h. The solvent was removed under reduced pressure. The title compound was obtained by flash column chromatography using 1:9 EtOAc/hexane as the eluant. $^1$H NMR (CDCl$_3$, 500 MHz) δ 8.11 (m, 1H), 8.02 (dd, J=9.0, 2.5 Hz, 1H), 7.81 (s, 1H), 7.74 (d, J=9.0 Hz, 1H), 7.70 (m, 1H), 7.65 (m, 1H), 4.67 (m, 4H), 3.89 (s, 3H).

Step E: Methyl [3,5-bis(trifluoromethyl)benzyl][(5'-isopropyl-2'-methoxy-4-nitrobiphenyl-2-yl)methyl]carbamate To a mixture of Methyl [3,5-bis(trifluoromethyl)benzyl](2-bromo-5-nitrobenzyl)carbamate from Step D (0.39 g, 0.75 mmol), 2-methoxy-5-isopropylphenyl boronic acid (0.175 g, 0.90 mmol), and potassium carbonate (0.21 g, 1.50 mmol) in 4:1 acetone/water (10 ml), a catalytic amount of palladium acetate (10 mg) was added. The mixture was heated to and maintained at reflux for 2 h. TLC analysis (acetone/hexane=5:95) showed completion of the reaction. The acetone was removed under reduced pressure and the organic was extracted with methylene chloride (3×25 ml). The combined organic layers were washed with brine and dried over sodium sulfate. The title compound was obtained by flash column chromatography using 5:95 acetone/hexane as the eluant. $^1$H NMR (CDCl$_3$, 500 MHz) δ 8.20 (m, 2H), 7.75 (s, 1H), 7.48 (m, 1H), 7.40 (d, J=8.0 Hz, 1H), 7.29 (m, 1H), 6.93 (m, 2H), 4.25-4.60 (m, 4H), 3.80 (m, 3H), 3.69 (s, 3H), 2.89 (m, 1H), 1.20 (s, 6H). LC-MS (M+1) 585.4 (4.49 min).

Example 9

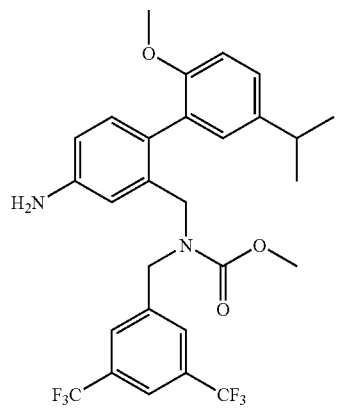

Methyl [(4-amino-5'-isopropyl-2'-methoxybiphenyl-2-yl)methyl][3,5-bis(trifluoromethyl)benzyl]carbamate A solution of the methyl [3,5-bis(trifluoromethyl)benzyl][(5'-isopropyl-2'-methoxy-4-nitrobiphenyl-2-yl)methyl]carbamate from Example 8 (0.31 g, 0.53 mmol) in MeOH (10 ml) was charged with a catalytic amount Pd/C and hydrogen at 40 psi for 1 h. The mixture was filtered through Celite and the filtrate was concentrated. The title compound was obtained by flash column chromatography using 3:7 EtOAc/hexane as the eluant. $^1$H NMR (CDCl$_3$, 500 MHz) δ 7.72 (m, 1H), 7.50 (s, 1H), 7.30 (s, 1H), 7.16 (m, 1H), 7.03 (d, J=8.0 Hz, 1H), 6.94 (s, 1H), 6.82 (m, 1H), 6.69 (dd, J=8.5, 2.5 Hz, 1H), 6.58 (m, 1H), 4.18-4.30 (m, 4H), 3.75 (s, 3H), 3.65 (s, 3H), 2.83 (m, 1H), 1.20 (s, 6H). LC-MS (M+1): 555.3 (3.58 min).

Example 10

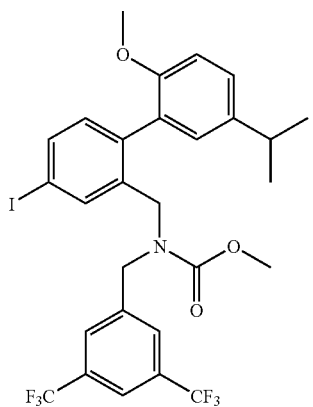

Methyl [3,5-bis(trifluoromethyl)benzyl][(4-iodo-5'-isopropyl-2'-methoxybiphenyl-2-yl)methyl]carbamate To a solution of the methyl [(4-amino-5'-isopropyl-2'-methoxybiphenyl-2-yl)methyl][3,5-bis(trifluoromethyl)benzyl]carbamate from Example 9 (0.31 g, 0.56 mmol) in chloroform (10 ml), n-amyl nitrite (0.11 ml, 0.84 mmol) and iodine (0.28 g, 1.1 mmol) were added. The mixture was heated to and maintained at reflux for 2 h. TLC analysis (5:95 EtOAc/hexane) showed completion of the reaction. The mixture was diluted with methylene chloride (20 ml) and washed with saturated sodium thiosulfate solution, brine. The light yellow solution was dried over sodium sulfate. The title compound was obtained by flash column chromatography using 5:95 EtOAc/hexane as the eluant. $^1$H NMR (CDCl$_3$, 500 MHz) δ 7.74 (s, 1H), 7.67 (dd, J=8.0, 2.0 Hz, 1H), 7.47 (m, 1H), 7.31 (dd, J=8.0, 2.0 Hz, 1H), 7.21 (d, J=8.0 Hz, 1H), 7.16 (d, J=8.5 Hz, 1H), 6.95 (d, J=8.0 Hz, 1H), 6.91 (dd, J=4.0, 2.5 Hz, 1H), 6.87 (d, J=8.5 Hz, 1), 4.20-4.48 (m, 4H), 3.78 (s, 3H), 3.70 (s, 3H), 2.92 (m, 1H), 1.23 (s, 3H), 1.21 (s, 3H). LC-MS (M+1) 666.0 (4.74 min).

Example 11

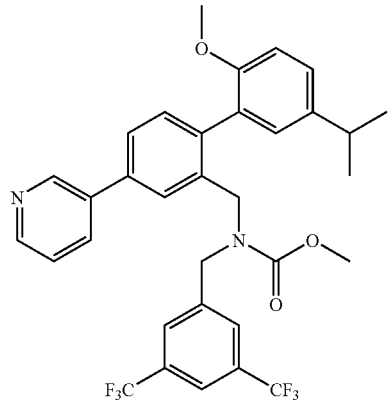

Methyl [3,5-bis(trifluoromethyl)benzyl][(5'-isopropyl-2'-methoxy-4-pyridin-3-ylbiphenyl-2-yl)methyl]carbamate A mixture of methyl [3,5-bis(trifluoromethyl)benzyl][(4-iodo-5'-isopropyl-2'-methoxybiphenyl-2-yl)methyl]carbamate from Example 10 (0.03 g, 0.045 mmol), potassium carbonate (0.012 g, 0.09 mmol), 3-pyridyl boronic acid (0.0066 g, 0.054 mmol) and a catalytic amount of palladium acetate (1 mg) in 4:1 acetone/water (2 ml) was heated to and maintained at reflux for 5 h. Acetone was removed and the organic was extracted with methylene chloride (3×10 ml). The combined organic layers were washed with brine and dried over sodium sulfate. The title compound was obtained after preparative thin layer chromatography using 3:7 EtOAc/hexane as the eluant. $^1$H NMR (CDCl$_3$, 500 MHz) δ 8.90 (m, 1H), 8.65 (m, 1H), 7.90 (m, 1H), 7.72 (s, 1H), 7.70 (m, 1H), 7.60 (dd, J=8.0, 2.5 Hz, 1H), 7.48 (m, 2H), 7.39 (d, J=8.0 Hz, 1H), 7.35 (s, 1H), 7.25 (m, 1H), 7.00 (s, 1H), 6.93 (d, J=8.0 Hz, 1H), 4.20-4.62 (m, 4H), 3.77 (s, 3H), 3.72 (s, 3H), 2.90 (m, 1H), 1.22 (s, 6H). LC-MS (M+1) 617.0 (3.76 min).

Example 12

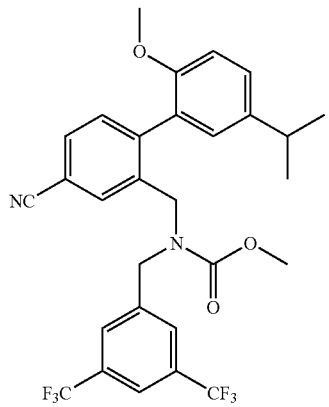

Methyl [3,5-bis(trifluoromethyl)benzyl][(4-cyano-5'-isopropyl-2'-methoxybiphenyl-2-yl)methyl]carbamate A mixture of methyl [3,5-bis(trifluoromethyl)benzyl][(4-iodo-5'-isopropyl-2'-methoxybiphenyl-2-yl)methyl]carbamate from Example 10 (0.03 g, 0.045 mmol) and CuCN (0.008 g, 0.09 mmol) in DMF (1 ml) was stirred at 100° C. overnight. Water (10 ml) was added and the mixture was extracted with EtOAc (3×15 ml). The combined EtOAc layers were washed with brine, and dried over sodium sulfate. The title compound was obtained after preparative thin layer chromatography using 2:8 EtOAc/hexane as the eluant. $^1$H NMR (CDCl$_3$, 500 MHz) δ 7.72 (s, 1H), 7.74 (m, 1H), 7.64 (d, J=8.0 Hz, 1H), 7.49 (m, 1H), 7.38 (m, 1H), 7.36 (d, J=8.0 Hz, 1H), 7.28 (m, 1H), 6.94 (d, J=2.5 Hz, 1H), 6.91 (m, 1H), 4.26-4.49 (m, 4H), 3.81 (m, 3H), 3.70 (s, 3H), 2.92 (m, 1H), 1.22 (s, 6H). LC-MS (M+1) 565.3 (4.42 min).

Example 13

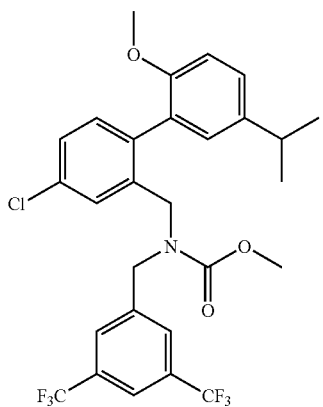

Methyl [3,5-bis(trifluoromethyl)benzyl][(4-chloro-5'-isopropyl-2'-methoxybiphenyl-2-yl)methyl]carbamate The title compound was prepared following the procedures from Example 8, Steps A, B, C, D, and E starting from methyl 2-bromo-5-chlorobenzoate. $^1$H NMR (CDCl$_3$, 500 MHz) δ 7.74 (s, 1H), 7.47 (s, 1H), 7.38 (m, 1H), 7.32 (s, 1H), 7.31 (dd, J=8.5, 2.5 Hz, 1H), 7.24 (d, J=2.5 Hz, 1H), 7.22 (m, 1H), 6.94 (d, J=2.5 Hz, 1H), 6.87 (d, J=8.5 Hz, 1H), 4.18-4.50 (m, 4H), 3.75 (s, 3H), 3.70 (s, 3H), 2.83 (m, 1H), 1.20 (s, 6H). LC-MS (M+1) 574.3 (4.66 min).

Example 14

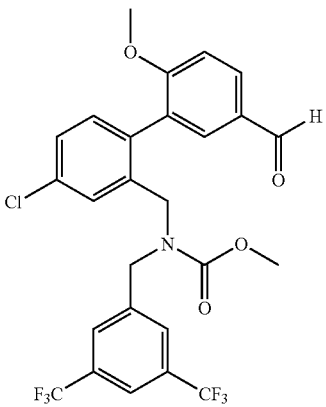

Methyl [3,5-bis(trifluoromethyl)benzyl][(4-chloro-5'-formyl-2'-methoxybiphenyl-2-yl)methyl]carbamate The title compound was prepared followed the procedures from Example 8, Step A, B, C, D, and E starting from methyl 2-bromo-5-chlorobenzoate and using 2-methoxy-5-formylphenyl boronic acid for Step E. $^1$H NMR (CDCl$_3$, 500 MHz) δ 9.95 (s, 1H), 7.92 (d, J=9.0 Hz, 1H), 7.74 (s, 1H), 7.65 (d, J=2.0 Hz, 1H), 7.48 (m, 1H), 7.38 (dd, J=8.0, 2.0 Hz, 1H), 7.34 (m, 1H), 7.23 (d, J=2.0 Hz, 1H), 7.20 (m, 1H), 7.06 (d, J=9.0 Hz, 1H), 4.10-4.58 (m, 4H), 3.82 (s, 3H), 3.70 (s, 3H). LC-MS (M+1) 560.1 (4.13 min).

Example 15

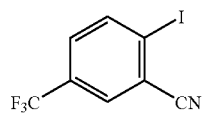

2-Iodo-5-(trifluoromethyl)benzonitrile

2-Amino-5-(trifluoromethyl)benzonitrile (3.06 g, 16.45 mmol) was suspended in CH$_2$I$_2$ (36 mL) and t-butyl nitrite (3.9 mL, 32.9 mmol) was added dropwise by syringe. The reaction was heated slowly to 100° C. and was maintained at this temperature for 30 minutes. The reaction was then cooled to room temperature, diluted with hexanes (200 mL), loaded on a silica gel column, and purified with 100% hexanes to 15% EtOAc/hexanes. The resulting product, 2-iodo-5-(trifluoromethyl)benzonitrile was contaminated with minor impurities which were removed by silica gel chromatography with 25% CH$_2$Cl$_2$/hexanes. 2-Iodo-5-(trifluoromethyl)benzonitrile was obtained as a white solid. R$_f$=0.44 (15% EtOAc/hexanes). $^1$H NMR (CDCl$_3$, 500 MHz) δ 8.10 (d, J=8.5 Hz, 1H), 7.85 (d, J=1.8 Hz, 1H), 7.52 (dd, J=8.5, 1.8 Hz, 1H).

Example 16

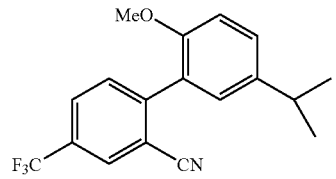

5'-Isopropyl-2'-methoxy-4-(trifluoromethyl)biphenyl-2-carbonitrile

To a solution of 2-iodo-5-(trifluoromethyl)benzonitrile (2.0 g, 6.7 mmol) and (5-isopropyl-2-methoxyphenyl)boronic acid (1.6 g, 8.4 mmol) in dimethyl ethylene glycol (30.4 mL) was added 2M Na$_2$CO$_3$ (6.8 mL), ethanol (9.6 mL), and water (10 mL). The solution was degassed with nitrogen for 2 minutes. Pd(PPh$_3$)$_4$ (774 mg, 0.67 mmol) was added and the solution was degassed with nitrogen again for 2 minutes. The solution was divided equally into two 40 mL microwave tubes. Each tube was degassed with nitrogen for 1 minute, sealed, and placed in a microwave reactor. The wattage was set for 200 W until the temperature reached 150° C. and then the temperature was held at 150° C. for ten minutes. The tubes were then cooled to room temperature, combined, poured into H₂O (50 mL), and extracted with EtOAc (100 mL). The organic layer was washed with brine (50 mL), dried over Na₂SO₄, filtered, and concentrated. Purification by flash chromatography with 15% CH₂Cl₂/hexanes afforded 5'-isopropyl-2'-methoxy-4-(trifluoromethyl)biphenyl-2-carbonitrile as a light yellow oil. $R_f$=0.65 (25% EtOAc/hexanes). ¹H NMR (CDCl₃, 500 MHz) δ 7.97 (s, 1H), 7.85 (d, J=8.0 Hz, 1H), 7.63 (d, J=8.0 Hz, 1H), 7.31 (dd, J=8.5, 2.0 Hz, 1H), 7.12 (d, J=2.0 Hz, 1H), 6.97 (d, J=8.5 Hz, 1H), 3.82 (s, 3H), 2.93 (m, 1H), 1.27 (d, J=7.0 Hz, 6H).

Example 17

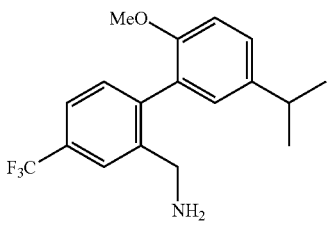

1-[5'-Isopropyl-2'-methoxy-4-(trifluoromethyl)biphenyl-2-yl]methanamine

5'-Isopropyl-2'-methoxy-4-(trifluoromethyl)biphenyl-2-carbonitrile (996.2 mg, 3.12 mmol) was dissolved in Et₂O (33 mL) and cooled to 0° C. LAH (12.49 mL of a 1 M solution in Et₂O, 12.49 mmol) was added dropwise by syringe. After stirring at 0° C. for 10 minutes, the reaction was warmed to room temperature and stirred at room temperature for 6 hours. The reaction was then quenched by slow dropwise addition of 1.5 mL of H₂O (vigorous evolution of gas), followed by 1.5 mL of 30% NaOH, followed by 3.0 mL of H₂O. The resulting gelatinous precipitate was washed with 5×20 mL of CH₂Cl₂; the organic washes were dried over Na₂SO₄, filtered and concentrated. Purification of the residue by flash chromatography with 2% MeOH/CH₂Cl₂ containing 0.1% Et₃N afforded 1-[5'-isopropyl-2'-methoxy-4-(trifluoromethyl)biphenyl-2-yl]methanamine. $R_f$=0.30 (10% MeOH/CH₂Cl₂). LCMS=324.3 (M+1)⁺. ¹H NMR (CDCl₃, 500 MHz) δ 7.77 (s, 1H), 7.55 (d, J=6.8 Hz, 1H), 7.32 (d, J=7.8 Hz, 1H), 7.25 (dd, J=8.3, 2.1 Hz, 1H), 7.00 (d, J=2.1 Hz, 1H), 6.92 (d, J=8.4 Hz, 1H), 3.66-3.74 (m, 5H), 2.91 (m, 1H), 1.26 (d, J=6.9 Hz, 6H).

Example 18

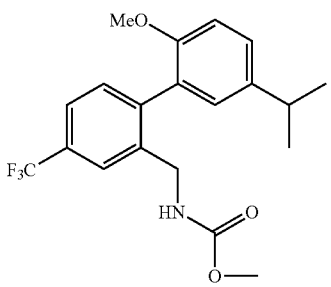

Methyl {[5'-isopropyl-2'-methoxy-4-(trifluoromethyl)biphenyl-2-yl]methyl}carbamate To a solution of 1-[5'-isopropyl-2'-methoxy-4-(trifluoromethyl)biphenyl-2-yl]methanamine (166 mg, 0.51 mmol) and methyl chloroformate (107 μL, 1.39 mmol) in CH₂Cl₂ (5 mL) was added N,N-diisopropylethylamine (485 μL, 2.79 mmol). The reaction was stirred at room temperature for twenty minutes and then was poured into H₂O (50 mL). The mixture was extracted with EtOAc (100 mL), and the organic layer was washed with brine (50 mL), dried over Na₂SO₄, filtered, and concentrated. Purification by flash chromatography with 2% to 20% EtOAc/hexanes afforded methyl {[5'-isopropyl-2'-methoxy-4-(trifluoromethyl)biphenyl-2-yl]methyl}carbamate. $R_f$=0.29 (15% EtOAc/hexanes). LCMS=382.3 (M+1)⁺. ¹H NMR (CDCl₃, 500 MHz) δ 7.68 (s, 1H), 7.57 (d, J=8.0 Hz, 1H), 7.31 (d, J=8.0 Hz, 1H), 7.25 (dd, J=8.5, 2.5 Hz, 1H), 6.97 (d, J=2.5 Hz, 1H), 6.91 (d, J=8.5 Hz, 1H), 4.17 (m, 2H), 3.75 (s, 3H), 3.65 (s, 3H), 2.89 (m, 1H), 1.25 (d, J=7.0 Hz, 6H).

Example 19

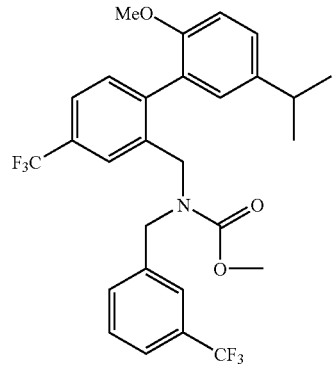

Methyl {[5'-isopropyl-2'-methoxy-4-(trifluoromethyl)biphenyl-2-yl]methyl}[3-(trifluoromethyl)benzyl]carbamate Methyl {[5'-isopropyl-2'-methoxy-4-(trifluoromethyl)biphenyl-2-yl]methyl}carbamate (20 mg, 0.053 mmol) was dissolved in THF (1 mL). 3-(Trifluoromethyl)benzyl bromide (122 μL, 0.79 mmol) was added followed by potassium bis(trimethylsilyl)amide (320 μL of a 0.5 M solution in toluene, 0.160 mmol). The reaction was stirred for two hours and then poured into H₂O (10 mL). The mixture was extracted with EtOAc (50 mL), and the organic extracts were washed with brine (10 mL), dried over Na₂SO₄, filtered, and concentrated. Purification by flash chromatography with 2% to 25% EtOAc/hexanes afforded methyl {[5'-isopropyl-2'-methoxy-4-(trifluoromethyl)biphenyl-2-yl]methyl}[3-(trifluoromethyl)benzyl]carbamate. $R_f$=0.67 (15% EtOAc/hexanes). LCMS=540.3 (M+1)⁺. ¹H NMR (C₆D₆, 500 MHz, 70° C.) δ 7.72 (s, 1H), 7.36 (dd, J=8.0, 1.0 Hz, 1H), 7.19-7.23 (m, 2H), 7.03-7.07 (m, 3H), 6.86 (m, 2H), 6.57 (d, J=8.5 Hz, 1H), 4.41 (s, 2H), 4.05 (s, 2H), 3.36 (s, 3H), 3.22 (s, 3H), 2.73 (m, 1H), 1.25 (d, J=6.5 Hz, 6H).

Example 20

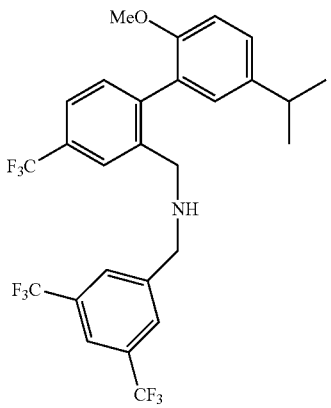

[3,5-Bis(trifluoromethyl)benzyl]{[5'-isopropyl-2'-methoxy-4-(trifluoromethyl)biphenyl-2-yl]methyl}amine 1-[5'-Isopropyl-2'-methoxy-4-(trifluoromethyl)biphenyl-2-yl]methanamine (94.1 mg, 0.291 mmol) was dissolved in THF (4 mL). 3,5-Bis(trifluoromethyl)benzyl bromide (320 µL, 1.75 mmol) was added followed by potassium bis(trimethylsilyl)amide (2.33 mL of a 0.5 M solution in toluene, 1.164 mmol). The reaction was stirred at room temperature for 72 hours and then poured into H$_2$O (30 mL). The mixture was extracted with EtOAc (75 mL). The organic layer was washed with brine (25 mL), dried over Na$_2$SO$_4$, filtered, and concentrated. Purification by flash chromatography with 0 to 15% EtOAc/hexanes, then a second column with 50% CH$_2$Cl$_2$, then a third column with 25% EtOAc/hexanes afforded [3,5-bis(trifluoromethyl)benzyl]{[5'-isopropyl-2'-methoxy-4-(trifluoromethyl)biphenyl-2-yl]methyl}amine as a light yellow oil. R$_f$=0.18 (40% CH$_2$Cl$_2$/hexanes). LCMS=550.3 (M+1)$^+$. $^1$H NMR (CDCl$_3$, 600 MHz) δ 7.75 (s, 1H), 7.74 (s, 1H), 7.70 (s, 2H), 7.58 (d, J=7.9 Hz, 1H), 7.34 (d, J=7.8 Hz, 1H), 7.24 (dd, J=8.5, 2.2 Hz, 1H), 6.99 (d, J=2.2 Hz, 1H), 6.90 (d, J=8.5 Hz, 1H), 3.68-3.76 (m, 4H), 3.68 (s, 3H), 2.88 (m, 1H), 1.22 (d, J=6.4 Hz, 6H).

Example 21

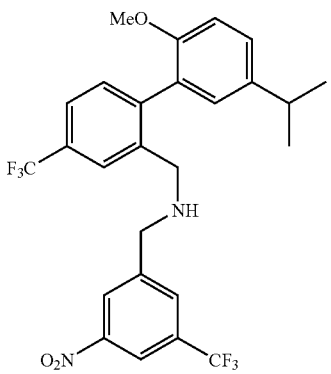

{[5'-Isopropyl-2'-methoxy-4-(trifluoromethyl)biphenyl-2-yl]methyl}[3-nitro-5-(trifluoromethyl)benzyl]amine To a solution of 3-nitro-5-(trifluoromethyl)benzaldehyde (366 mg, 1.67 mmol) in MeOH (4 mL) was added a solution of 1-[5'-isopropyl-2'-methoxy-4-(trifluoromethyl)biphenyl-2-yl]methanamine (270 mg, 0.84 mmol) in MeOH (4 mL) followed by addition of NaCNBH$_3$ (105 mg, 1.67 mmol) and one drop of acetic acid. The reaction was stirred for 24 hours at room temperature and then poured into H$_2$O (30 mL). The mixture was extracted with EtOAc (60 mL), and the organic extracts were washed with brine (20 mL), dried over Na$_2$SO$_4$, filtered, and concentrated. Purification by flash chromatography with 2% to 25% EtOAc/hexanes afforded {[5'-isopropyl-2'-methoxy-4-(trifluoromethyl)biphenyl-2-yl]methyl}[3-nitro-5-(trifluoromethyl)benzyl]amine as a yellow oil. R$_f$=0.45 (15% EtOAc/hexanes). LCMS=527.2 (M+1)$^+$. $^1$H NMR (CDCl$_3$, 500 MHz) δ 8.33 (s, 1H), 8.27 (s, 1H), 7.85 (s, 1H), 7.74 (s, 1H), 7.56 (d, J=8.0 Hz, 1H), 7.33 (d, J=8.0 Hz, 1H), 7.22 (dd, J=8.5 Hz, 2.0 Hz, 1H), 6.97 (d, J=2.0 Hz, 1H), 6.89 (d, J=8.5 Hz, 1H), 3.67-3.78 (m, 4H), 3.70 (s, 3H), 2.87 (m, 1H), 1.25 (d, J=7.0 Hz, 6H).

Example 22

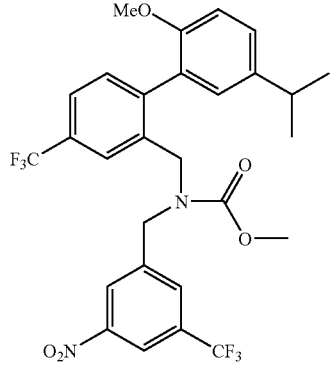

Methyl {[5'-isopropyl-2'-methoxy-4-(trifluoromethyl)biphenyl-2-yl]methyl}[3-nitro-5-(trifluoromethyl)benzyl]carbamate To a solution of {[5'-isopropyl-2'-methoxy-4-(trifluoromethyl)biphenyl-2-yl]methyl}[3-nitro-5-(trifluoromethyl)benzyl]amine (428 mg, 0.81 mmol) and methyl chloroformate (126 µL, 1.39 mmol) in CH$_2$Cl$_2$ (10 mL) was added N,N-diisopropylethylamine (566 µL, 3.25 mmol). The reaction was stirred at room temperature for twenty minutes and then was poured into H$_2$O (25 mL). The mixture was extracted with EtOAc (70 mL), and the organic extracts were washed with brine (25 mL), dried over Na$_2$SO$_4$, filtered, and concentrated. Purification by flash chromatography with 2% to 20% EtOAc/hexanes afforded methyl {[5'-isopropyl-2'-methoxy-4-(trifluoromethyl)biphenyl-2-yl]methyl}[3-nitro-5-(trifluoromethyl)benzyl]carbamate. R$_f$=0.37 (25% EtOAc/hexanes). LCMS=585.3 (M+1)$^+$. $^1$H NMR (C$_6$D$_6$, 500 MHz, 70° C.) δ 8.03 (s, 1H), 7.78 (s, 1H), 7.64 (s, 1H), 7.37 (s, 1H), 7.33 (d, J=8.0 Hz, 1H), 7.04-7.06 (m, 2H), 6.83 (s, 1H), 6.60

(d, J=8.4 Hz, 1H), 4.37 (bs, 2H), 3.93 (bs, 2H), 3.36 (s, 3H), 3.26 (s, 3H), 2.73 (m, 1H), 1.15 (d, J=6.8 Hz, 6H).

Example 23

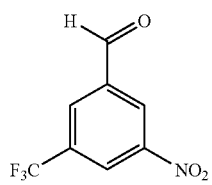

3-Nitro-5-(trifluoromethyl)benzaldehyde

Step A: [3-Nitro-5-(trifluoromethyl)phenyl]methanol

To a solution of 3-nitro-5-(trifluoromethyl)benzoic acid (2.0 g, 8.5 mmol) in THF (100 mL) was added borane-THF (17 mL of a 1 M solution in THF, 17 mmol). The reaction was stirred at 60° C. for 24 hours and then poured into $H_2O$ (50 mL). The resultant mixture was extracted with EtOAc (100 mL) and the organic layer was washed with brine (50 mL), dried over $Na_2SO_4$, filtered, and concentrated. Purification by flash chromatography with 50% EtOAc/hexanes afforded [3-nitro-5-(trifluoromethyl)phenyl]methanol. $R_f$=0.35 (75% EtOAc/hexanes). $^1$H NMR (CDCl$_3$, 500 MHz) δ 8.44 (s, 1H), 8.40 (s, 1H), 7.98 (s, 1H), 4.91 (s, 2H), 2.07 (bs, 1H).

Step B: 3-Nitro-5-(trifluoromethyl)benzaldehyde

A solution of [3-nitro-5-(trifluoromethyl)phenyl]methanol (400 mg, 1.88 mmol) in CH$_2$Cl$_2$ (20 mL) was cooled to 0° C. and then Dess-Martin periodinane (1.59 g, 3.76 mmol) was added. The reaction was slowly warmed to room temperature. After stirring at room temperature for twenty minutes, the reaction was poured into 1N NaOH (25 mL). The mixture was extracted with EtOAc (50 mL) and the organic extracts were washed with brine (25 mL), dried over Na$_2$SO$_4$, filtered, and concentrated. Purification by flash chromatography with 0% to 15% EtOAc/hexanes afforded 3-nitro-5-(trifluoromethyl)benzaldehyde. $R_f$=0.39 (15% EtOAc/hexanes). $^1$H NMR (CDCl$_3$, 500 MHz) δ 10.18 (s, 1H), 8.91 (s, 1H), 8.74 (s, 1H), 8.48 (s, 1H).

Example 24

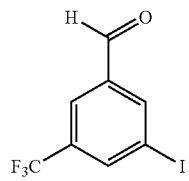

3-Iodo-5-(trifluoromethyl)benzaldehyde

Step A: [3-Amino-5-(trifluoromethyl)phenyl]methanol

To a solution of [3-nitro-5-(trifluoromethyl)phenyl]methanol (1.8 g, 8.0 mmol) (Step A, Example 23) in THF (36 mL) was added concentrated HCl (18 mL) and SnCl$_2$.2H$_2$O (8.7 g, 38.8 mmol). The reaction was stirred at room temperature for 24 hours and then poured slowly into saturated NaHCO$_3$ (250 mL). After neutralization was complete, the reaction was extracted with EtOAc (3×50 mL). The organic extracts were washed with brine (75 mL), dried over Na$_2$SO$_4$, filtered, and concentrated. Purification by flash chromatography with 50% EtOAc/hexanes afforded 1.5 g (quantitative) of [3-amino-5-(trifluoromethyl)phenyl]methanol. $R_f$=0.35 (50% EtOAc/hexanes). $^1$H NMR (CDCl$_3$, 500 MHz) δ 6.98 (s, 1H), 6.84 (s, 1H), 6.81 (s, 1H), 4.65 (s, 2H), 3.87 (bs, 1H).

Step B: [3-Iodo-5-(trifluoromethyl)phenyl]methanol

[3-amino-5-(trifluoromethyl)phenyl]methanol (500 mg, 5.2 mmol) was suspended in CH$_2$I$_2$ (5 mL) and t-butyl nitrite (622 μL, 5.2 mmol) was added dropwise by syringe. The reaction was heated slowly to 100° C. and was maintained at this temperature for 30 minutes. The reaction was then cooled to room temperature, diluted with hexanes (50 mL), loaded on a silica gel column, and purified with 100% hexanes to 25% EtOAc/hexanes to afford [3-iodo-5-(trifluoromethyl)phenyl]methanol. $R_f$=0.19 (15% EtOAc/hexanes). $^1$H NMR (CDCl$_3$, 500 MHz) δ 7.91 (s, 1H), 7.87 (s, 1H), 7.59 (s, 1H), 4.73 (d, J=4.9 Hz, 2H), 1.86 (t, J=5.6 Hz, 1H).

Step C: 3-Iodo-5-(trifluoromethyl)benzaldehyde

A solution of [3-iodo-5-(trifluoromethyl)phenyl]methanol (287 mg, 0.95 mmol) in CH$_2$Cl$_2$ (10 mL) was cooled to 0° C. and then Dess-Martin periodinane (604 mg, 1.42 mmol) was added. The reaction was slowly warmed to room temperature. After stirring at room temperature for twenty minutes, the reaction was poured into 1N NaOH (25 mL). The mixture was extracted with EtOAc (50 mL) and the organic extracts were washed with brine (25 mL), dried over Na$_2$SO$_4$, filtered, and concentrated. Purification by flash chromatography with 0% to 10% EtOAc/hexanes afforded 3-iodo-5-(trifluoromethyl)benzaldehyde. $R_f$=0.54 (15% EtOAc/hexanes). $^1$H NMR (CDCl$_3$, 600 MHz) δ 9.98 (s, 1H), 8.39 (s, 1H), 8.19 (s, 1H), 8.09 (s, 1H).

Example 25

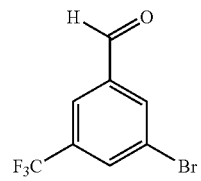

3-Bromo-5-(trifluoromethyl)benzaldehyde

Step A: [3-Bromo-5-(trifluoromethyl)-phenyl]methanol

[3-amino-5-(trifluoromethyl)phenyl]methanol (900 mg, 4.71 mmol) (Step A, Example 24) was suspended in CHBr$_3$ (9 mL), and t-butyl nitrite (600 μL, 5.04 mmol) was added dropwise by syringe. The reaction was heated slowly to 80° C. and was maintained at this temperature for 10 minutes. The reaction was then cooled to room temperature, diluted with hexanes (50 mL), loaded on a silica gel column, and purified with 100% hexanes to 20% EtOAc/hexanes (2 columns) to afford [3-bromo-5-(trifluoromethyl) phenyl]methanol. $R_f$=0.31 (25% EtOAc/hexanes). $^1$H NMR (CDCl$_3$, 500 MHz) δ 7.71 (s, 1H), 7.68 (s, 1H), 7.56 (s, 1H), 4.76 (d, J=5.5 Hz, 2H), 1.86 (t, J=5.7 Hz, 1H).

Step B: 3-Bromo-5-(trifluoromethyl)benzaldehyde

A solution of [3-bromo-5-(trifluoromethyl)phenyl]methanol (409 mg, 1.61 mmol) in $CH_2Cl_2$ (25 mL) was cooled to 0° C. and then Dess-Martin periodinane (1.02 g, 2.41 mmol) was added. The reaction was stirred at 0° C. for 30 minutes and then warmed to room temperature. After stirring at room temperature for thirty minutes, the reaction was poured into 1N NaOH (25 mL). The mixture was extracted with EtOAc (100 mL), and the organic extracts were washed with 1N NaOH (25 mL), then brine (25 mL), dried over $Na_2SO_4$, filtered, and concentrated. Purification by flash chromatography with 25% EtOAc/hexanes afforded 3-bromo-5-(trifluoromethyl)benzaldehyde. $R_f$=0.60 (25% EtOAc/hexanes). $^1$H NMR ($CDCl_3$, 500 MHz) δ 10.02 (s, 1H), 8.20 (s, 1H), 8.07 (s, 1H), 8.02 (s, 1H).

Example 26

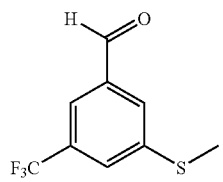

3-(Methylthio)-5-(trifluoromethyl)benzaldehyde

Step A: [3-(Methylthio)-5-(trifluoromethyl)phenyl]methanol

To a solution of [3-amino-5-(trifluoromethyl)phenyl]methanol (319 mg, 1.67 mmol) (Step A, Example 24) in $CHCl_3$ (5 mL) was added dimethyl disulfide (296 µL, 3.34 mmol). Next, t-butyl nitrite (285 µL, 2.4 mmol) was added dropwise by syringe. The reaction was stirred at room temperature for two hours and then poured into $H_2O$ (15 mL). The mixture was extracted with EtOAc (50 mL), washed with brine (15 mL), dried over $Na_2SO_4$, filtered, and concentrated. Purification by flash chromatography with 0% to 50% EtOAc/hexanes afforded [3-(methylthio)-5-(trifluoromethyl)phenyl]-methanol. The [3-(methylthio)-5-(trifluoromethyl)phenyl]methanol was contaminated with minor impurities that were removed after the next step. $R_f$=0.53 (50% EtOAc/hexanes). $^1$H NMR ($CDCl_3$, 500 MHz) δ 7.63 (s, 1H), 7.40 (s, 1H), 7.35 (s, 1H), 4.71 (s, 2H), 2.51 (s, 3H).

Step B: 3-(Methylthio)-5-(trifluoromethyl)benzaldehyde

A solution of [3-(methylthio)-5-(trifluoromethyl)phenyl]methanol (200 mg, 0.99 mmol) in $CH_2Cl_2$ (20 mL) was cooled to 0° C. and then Dess-Martin periodinane (573 mg, 1.35 mmol) was added. The reaction was slowly warmed to room temperature. After stirring at room temperature for twenty minutes, the reaction was poured into 1N NaOH (25 mL). The mixture was extracted with EtOAc (75 mL). The organic extracts were washed with brine (25 mL), dried over $Na_2SO_4$, filtered, and concentrated. Purification by flash chromatography with 1% to 10% EtOAc/hexanes afforded 3-(methylthio)-5-(trifluoromethyl)benzaldehyde. $R_f$=0.55 (25% EtOAc/hexanes). $^1$H NMR ($CDCl_3$, 500 MHz) δ 10.02 (s, 1H), 7.87 (s, 1H), 7.84 (s, 1H), 7.68 (s, 1H), 2.58 (s, 3H).

Example 27

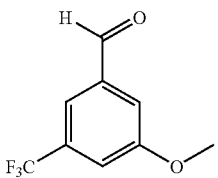

3-Methoxy-5-(trifluoromethyl)benzaldehyde

Step A: 1-Iodo-3-methoxy-5-(trifluoromethyl)benzene 3-methoxy-5-(trifluoromethyl)aniline (100 mg, 0.52 mmol) was dissolved in $CHCl_3$ (5.2 mL) and t-butyl nitrite (124 µL, 1.05 mmol) was added dropwise by syringe. Iodine (266 mg, 1.05 mmol) was added and then the reaction was slowly heated to 50° C. and was maintained at this temperature for an hour and thirty minutes. The reaction was then cooled to room temperature and poured into aq. $NaHSO_3$ (50 mL). The mixture was extracted with EtOAc (50 mL) and the organic extracts were washed with aq. $NaHSO_3$ (3×50 mL) and brine (20 mL), dried over $Na_2SO_4$, filtered, and concentrated. Purification by flash chromatography with 1% to 15% EtOAc/hexanes afforded 1-iodo-3-methoxy-5-(trifluoromethyl)benzene. $R_f$=0.75 (25% EtOAc/hexanes). $^1$H NMR ($CDCl_3$, 500 MHz) δ 7.53 (s, 1H), 7.41 (s, 1H), 7.09 (s, 1H), 3.82 (s, 3H).

Step B: 3-Methoxy-5-(trifluoromethyl)benzonitrile

To a solution of 1-iodo-3-methoxy-5-(trifluoromethyl)benzene (200 mg, 0.66 mmol) in DMF (2 mL) was added CuCN (300 mg, 5.0 mmol). The reaction was stirred at 100° C. for 24 hours and then poured into aq. $NH_3$ (40 mL). The mixture was extracted with EtOAc (70 mL) and the organic extracts were washed with brine (25 mL), dried over $Na_2SO_4$, filtered, and concentrated. Purification by flash chromatography with 5% to 80% EtOAc/hexanes afforded 3-methoxy-5-(trifluoromethyl)benzonitrile. $R_f$=0.64 (50% EtOAc/hexanes). $^1$H NMR ($CDCl_3$, 600 MHz) δ 7.47 (s, 1H), 7.34 (s, 1H), 7.31 (s, 1H), 3.89 (s, 3H).

Step C: 3-Methoxy-5-(trifluoromethyl)benzaldehyde

A mixture of 3-methoxy-5-(trifluoromethyl)benzonitrile (88 mg, 0.43 mmol) and $PtO_2$ (9.8 mg, 0.043 mmol) in 88% formic acid (651 µL) was heated to 60° C. The reaction was stirred at this temperature for thirty minutes. The reaction was then cooled to room temperature, diluted with hexanes (5 mL), loaded on a silica gel column, and purified with 1% to 15% EtOAc/hexanes to afford 3-methoxy-5-(trifluoromethyl)benzaldehyde. $R_f$=0.56 (25% EtOAc/hexanes). $^1$H NMR ($CDCl_3$, 500 MHz) δ 10.01 (s, 1H), 7.71 (s, 1H), 7.56 (s, 1H), 7.39 (s, 1H), 3.92 (s, 3H).

Example 28

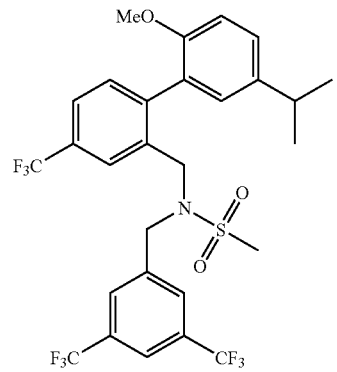

61

N-[3,5-Bis(trifluoromethyl)benzyl]-N-{[5'-isopropyl-2'-methoxy-4-(trifluoromethyl)-biphenyl-2-yl]methyl}methanesulfonamide To a solution of [3,5-bis(trifluoromethyl)benzyl]{[5'-isopropyl-2'-methoxy-4-(trifluoromethyl)biphenyl-2-yl]methyl}amine (8.3 mg, 0.015 mmol) (Example 20) and methanesulfonyl chloride (10.5 μL, 0.135 mmol) in CH$_2$Cl$_2$ (500 μL) was added N,N-diisopropylethylamine (47.4 μL, 0.273 mmol). The reaction was stirred at room temperature for twenty minutes and then was poured into H$_2$O (10 mL). The mixture was extracted with EtOAc (50 mL), and the organic extracts were washed with brine (10 mL), dried over Na$_2$SO$_4$, filtered, and concentrated. Purification by flash chromatography with 50% CH$_2$Cl$_2$/hexanes afforded N-[3,5-bis(trifluoromethyl)benzyl]-N-{[5'-isopropyl-2'-methoxy-4-(trifluoromethyl)biphenyl-2-yl]methyl}methanesulfonamide. R$_f$=0.20 (50% CH$_2$Cl$_2$/hexanes). LCMS=628.3 (M+1)$^+$. $^1$H NMR (CDCl$_3$, 600 MHz) δ 7.69 (s, 1H), 7.55 (s, 1H), 7.50 (d, J=8.4 Hz, 1H), 7.47 (s, 2H), 7.28-7.30 (m, 2H), 6.94 (d, J=9.0 Hz, 1H), 6.92 (d, J=1.8 Hz, 1H), 4.44 (d, J=15.0, 1H), 4.32 (d, J=15.0 Hz, 1H), 4.19 (d, J=15.6 Hz, 1H), 4.14 (d, J=15.6 Hz, 1H), 3.72 (s, 3H), 2.89 (m, 1H), 2.69 (s, 3H), 1.21-1.25 (m, 6H).

Example 29

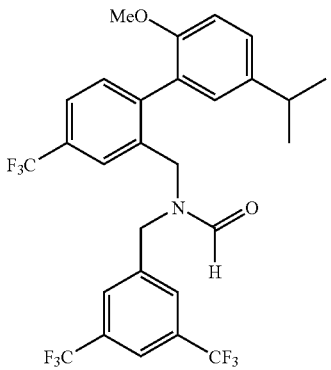

[3,5-Bis(trifluoromethyl)benzyl]{[5'-isopropyl-2'-methoxy-4-(trifluoromethyl)biphenyl-2-yl]methyl}formamide A solution of [3,5-bis(trifluoromethyl)benzyl]{[5'-isopropyl-2'-methoxy-4-(trifluoromethyl)biphenyl-2-yl]methyl}amine (88 mg, 0.43 mmol) (Example 20) in 80% formic acid (3 mL) was heated to and maintained at reflux for 24 hours. The reaction was then cooled to room temperature, poured into saturated NaHCO$_3$ (30 mL), and, after neutralization was complete, extracted with EtOAc (25 mL). The organic extracts were washed with brine (10 mL), dried over Na$_2$SO$_4$, filtered, and concentrated. Purification by flash chromatography with 15% EtOAc/hexanes afforded [3,5-bis(trifluoromethyl)benzyl]{[5'-isopropyl-2'-methoxy-4-(trifluoromethyl)biphenyl-2-yl]methyl}formamide. R$_f$=0.20 (15% EtOAc/hexanes). LCMS=578.3 (M+1)$^+$. $^1$H NMR (CD$_2$Cl$_2$, 600 MHz, rotamers present, ratio of major:minor ~3:1. Data for major rotamer given.) δ 6.86-8.31 (m, 10H), 4.24-4.47 (m, 4H), 3.71 (s, 3H), 2.87 (m, 1H), 1.27 (m, 6H).

62

Example 30

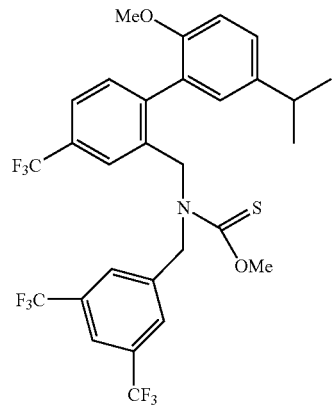

O-Methyl [3,5-bis(trifluoromethyl)benzyl]{[5'-isopropyl-2'-methoxy-4-(trifluoromethyl)-biphenyl-2-yl]methyl}thiocarbamate In a dry flask was placed CH$_2$Cl$_2$ (1 mL) and thiophosgene (20 μL, 0.262 mmol). [3,5-Bis(trifluoromethyl)benzyl]{[5'-isopropyl-2'-methoxy-4-(trifluoromethyl)biphenyl-2-yl]methyl}amine (15 mg, 0.027 mmol) (Example 20) was added to the flask as a solution in CH$_2$Cl$_2$ (0.5 mL). The reaction was stirred for several minutes at room temperature, and then a slurry of NaOMe (133 mg, 2.46 mmol) in MeOH (2 mL) was added. The reaction was stirred at room temperature for 20 minutes and then poured into saturated NH$_4$Cl (25 mL). The mixture was extracted with EtOAc (50 mL) and the organic extract was washed with brine (25 mL), dried over Na$_2$SO$_4$, filtered, and concentrated. The residue was purified by preparative thin layer chromatography (40% CH$_2$Cl$_2$/hexanes) to yield O-methyl[3,5-bis(trifluoromethyl)benzyl]{[5'-isopropyl-2'-methoxy-4-(trifluoromethyl)biphenyl-2-yl]methyl}thiocarbamate. R$_f$=0.41 (40% CH$_2$Cl$_2$/hexanes). LCMS=624.2 (M+1)$^+$. $^1$H NMR (CDCl$_3$, 500 MHz) (rotamers present; doubling of some peaks; partial data given) δ 7.55-7.73 (m, 3H), 7.22-7.36 (m, 4H), 6.87-6.93 (m, 2H), 5.11 (s), 5.02 (d, J=15.6 Hz), 4.85 (d, J=15.6 Hz), 4.70 (d, J=15.8 Hz), 4.50 (s), 4.49 (d, J=15.8 Hz), 4.09 (s, minor rotamer), 4.01 (s, major rotamer), 3.68 (s, minor rotamer), 3.67 (s, major rotamer), 2.87 (m, 1H), 1.19-1.22 (m, 6H).

Example 31

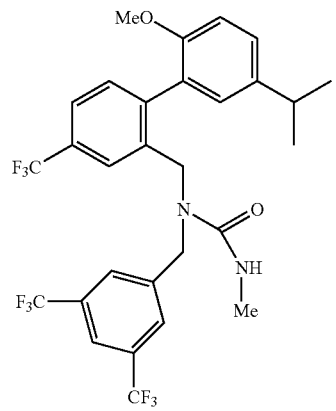

N-[3,5-Bis(trifluoromethyl)benzyl]-N-{[5'-isopropyl-2'-methoxy-4-(trifluoromethyl)biphenyl-2-yl]methyl}-N'-methylurea To a solution of [3,5-bis(trifluoromethyl)benzyl]{[5'-isopropyl-2'-methoxy-4-(trifluoromethyl)biphenyl-2-yl]methyl}amine (17.4 mg, 0.031 mmol) (Example 20) in CH$_2$Cl$_2$ (2 mL) was added methyl isocyanate (3 drops added by pipette, ~15 µL). The reaction was stirred at room temperature for 30 minutes, and then MeOH (1 mL) was added and the reaction was stirred for 5 minutes. The reaction was diluted with EtOAc (30 mL) and washed with water and brine (15 mL each). The organic layer was dried over Na$_2$SO$_4$, filtered, and concentrated. Purification by flash chromatography (40% EtOAc/hexanes) gave N-[3,5-bis(trifluoromethyl)benzyl]-N-{[5'-isopropyl-2'-methoxy-4-(trifluoromethyl)biphenyl-2-yl]methyl}-N'-methylurea. R$_f$=0.32 (40% EtOAc/hexanes). LCMS=607.4 (M+1)$^+$. $^1$H NMR (CDCl$_3$, 500 MHz) δ 7.74 (s, 1H), 7.66 (s, 2H), 7.59 (d, J=7.7 Hz, 1H), 7.43 (s, 1H), 7.32 (d, J=7.8 Hz, 1H), 7.24 (dd, J=8.7, 2.3 Hz, 1H), 6.90-6.92 (m, 2H), 4.85 (d, J=15.8 Hz, 1H), 4.50 (d, J=15.8 Hz, 1H), 4.45 (m, 1H), 4.39 (d, J=17.9 Hz, 1H), 4.02 (d, J=17.8 Hz, 1H), 3.71 (s, 3H), 2.87 (m, 1H), 2.76 (d, J=4.3 Hz, 3H), 1.20-1.22 (m, 6H).

Example 32

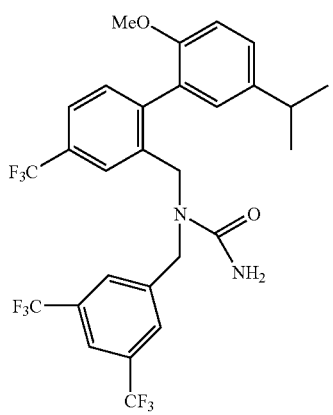

N-[3,5-Bis(trifluoromethyl)benzyl]-N-{[5'-isopropyl-2'-methoxy-4-(trifluoromethyl)-biphenyl-2-yl]methyl}urea

[3,5-Bis(trifluoromethyl)benzyl]{[5'-isopropyl-2'-methoxy-4-(trifluoromethyl)biphenyl-2-yl]methyl}amine (40.3 mg, 0.073 mmol) (Example 20) was dissolved in CH$_2$Cl$_2$ (3 mL) and the solution was cooled to −78° C. Chlorosulfonyl isocyanate (32 µL, 0.367 mmol) was added dropwise by syringe. The reaction was stirred at −78° C. for 15 minutes, and then at 0° C. for 20 minutes. The reaction was then poured into H$_2$O (15 mL) and saturated NaHCO$_3$ (15 mL) was added. The mixture was extracted with CH$_2$Cl$_2$ (2×25 mL). The organic extracts were dried over Na$_2$SO$_4$, filtered, and concentrated. Purification of the residue by flash chromatography with 50% EtOAc/hexanes afforded N-[3,5-bis(trifluoromethyl)benzyl]-N-{[5'-isopropyl-2'-methoxy-4-(trifluoromethyl)biphenyl-2-yl]methyl}urea. R$_f$=0.24 (40% EtOAc/hexanes). LCMS=593.3 (M+1)$^+$. $^1$H NMR (CDCl$_3$, 600 MHz) δ 7.75 (s, 1H), 7.66 (s, 2H), 7.60 (d, J=7.7 Hz, 1H), 7.47 (s, 1H), 7.33 (d, J=8.0 Hz, 1H), 7.25 (dd, J=8.5, 2.3 Hz, 1H), 6.92 (d, J=2.4 Hz, 1H), 6.90 (d, J=8.5 Hz, 1H), 4.80 (d, J=15.8 Hz, 1H), 4.53 (s, 2H), 4.48 (d, J=15.8 Hz, 1H), 4.45 (d, J=17.8 Hz, 1H), 4.07 (d, J=17.8 Hz, 1H), 3.69 (s, 3H), 2.87 (m, 1H), 1.20-1.22 (m, 6H).

Example 33

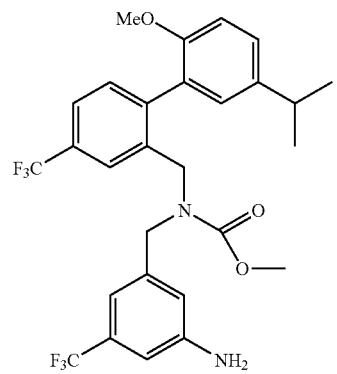

Methyl[3-amino-5-(trifluoromethyl)benzyl]{[5'-isopropyl-2'-methoxy-4-(trifluoromethyl)biphenyl-2-yl]methyl}carbamate A solution of methyl{[5'-isopropyl-2'-methoxy-4-(trifluoromethyl)biphenyl-2-yl]methyl}[3-nitro-5-(trifluoromethyl)benzyl]carbamate (174 mg, 0.03 mmol) (Example 22) and PtO$_2$ (10 mg) in THF (10 mL) was placed under hydrogen. The reaction was stirred at room temperature under hydrogen for two hours. The reaction was then diluted with hexanes (25 mL), loaded on a silica gel column, and purified with 15% EtOAc/hexanes to afford methyl[3-amino-5-(trifluoromethyl)benzyl]{[5'-isopropyl-2'-methoxy-4-(trifluoromethyl)biphenyl-2-yl]methyl}carbamate. R$_f$=0.31 (25% EtOAc/hexanes). LCMS=555.3 (M+1)$^+$. $^1$H NMR (CDCl$_3$, 600 MHz) δ 7.59-6.28 (m, 9H), 4.48-3.62 (m, 12H), 2.87 (m, 1H), 1.22 (broad singlet, 6H).

Example 34

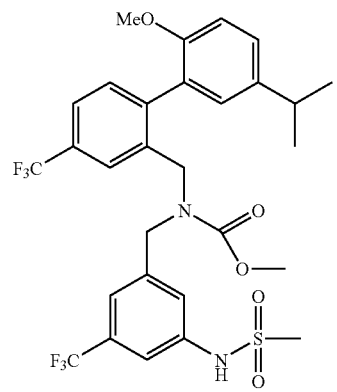

Methyl{[5'-isopropyl-2'-methoxy-4-(trifluoromethyl)
biphenyl-2-yl]methyl}[3-[(methylsulfonyl)amino]-5-
(trifluoromethyl)benzyl]carbamate To a solution of methyl[3-amino-5-(trifluoromethyl)benzyl]{[5'-isopropyl-2'-methoxy-4-(trifluoromethyl)biphenyl-2-yl]methyl}carbamate (8 mg, 0.014 mmol) (Example 33) and methanesulfonyl chloride (3.3 µL, 0.043 mmol) in CH$_2$Cl$_2$ (1 mL) was added N,N-diisopropylethylamine (15 µL, 0.086 mmol). The reaction was stirred at room temperature for thirty minutes and then was poured into H$_2$O (10 mL). The mixture was extracted with EtOAc (50 µL), and the organic extracts were washed with brine (10 mL), dried over Na$_2$SO$_4$, filtered, and concentrated. Purification by preparative thin layer chromatography with 25% EtOAc/hexanes followed by a preparative thin layer chromatography in 2:2:1 (CH$_2$Cl$_2$:Hex:Et$_2$O) and then a third and final purification by silica gel chromatography with 2% to 25% EtOAc/hexanes afforded methyl{[5'-isopropyl-2'-methoxy-4-(trifluoromethyl)biphenyl-2-yl]methyl}[3-[(methylsulfonyl)amino]-5-(trifluoromethyl)benzyl]carbamate. R$_f$=0.40 (25% EtOAc/hexanes). $^1$H NMR (C$_6$D$_6$, 500 MHz, 70° C.) δ 7.69 (s, 1H), 7.52 (s, 1H), 7.38-7.25 (m, 3H), 7.08-7.04 (m, 2H), 6.86 (s, 1H), 6.30 (d, J=8.5 Hz, 1H), 4.40 (broad singlet, 2H), 4.04-3.99 (m, 2H), 3.33 (s, 3H), 3.26 (s, 3H), 2.74 (m, 1H), 2.67 (s, 3H), 1.22 (d, J=6.5 Hz, 6H).

Example 35

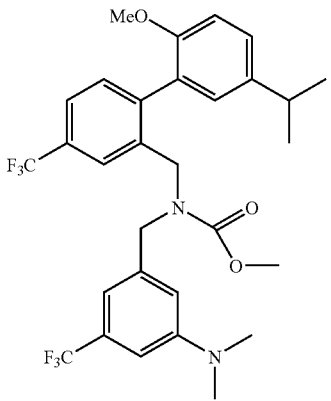

Methyl[3-(dimethylamino)-5-(trifluoromethyl)benzyl]{[5'-isopropyl-2'-methoxy-4-(trifluoromethyl)
biphenyl-2-yl]methyl}carbamate Methyl[3-amino-5-(trifluoromethyl)benzyl]{[5'-isopropyl-2'-methoxy-4-(trifluoromethyl)biphenyl-2-yl]methyl}carbamate (8 mg, 0.014 mmol) (Example 33) was dissolved in THF (1 mL). MeI (3.6 µL, 0.056 mmol) was added followed by potassium bis(trimethylsilyl)amide (112 µl of a 0.5 M solution in toluene, 0.056 mmol). The reaction was stirred at room temperature for two hours and then poured into H$_2$O (10 mL). The mixture was extracted with EtOAc (50 mL), and the organic extracts were washed with brine (10 mL), dried over Na$_2$SO$_4$, filtered, and concentrated. Purification by flash chromatography with 5% to 25% EtOAc/hexanes afforded methyl[3-(dimethylamino)-5-(trifluoromethyl)benzyl]{[5'-isopropyl-2'-methoxy-4-(trifluoromethyl)biphenyl-2-yl]methyl}carbamate. R$_f$=0.53 (25% EtOAc/hexanes). LCMS=583.3 (M+1)$^+$. $^1$H NMR (CDCl$_3$, 500 MHz) δ 7.56-6.44 (m, 9H), 4.49-4.13 (m, 4H), 3.73-3.65 (m, 6H), 2.92-2.85 (m, 7H), 1.21 (broad singlet, 6H).

Example 36

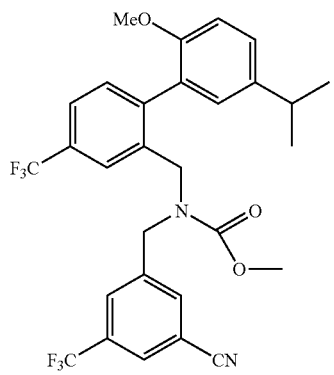

Methyl[3-cyano-5-(trifluoromethyl)benzyl]{[5'-isopropyl-2'-methoxy-4-(trifluoromethyl)biphenyl-2-yl]
methyl}carbamate To a solution of methyl[3-iodo-5-(trifluoromethyl)benzyl]{[5'-isopropyl-2'-methoxy-4-(trifluoromethyl)biphenyl-2-yl]methyl}carbamate (Example 119, 508 mg, 0.76 mmol) in DMF (40 mL) was added CuCN (1.7 g, 19.0 mmol). The reaction was stirred at 100° C. for 30 hours. The reaction was poured into aq. NH$_3$ (40 mL) and extracted with EtOAc (3×40 mL). All the collected organic extracts were washed with brine (40 mL), dried over Na$_2$SO$_4$, filtered, and concentrated. Purification by flash chromatography with 5% to 80% EtOAc/hexanes afforded methyl[3-cyano-5-(trifluoromethyl)benzyl]{[5'-isopropyl-2'-methoxy-4-(trifluoromethyl)biphenyl-2-yl]methyl}carbamate. R$_f$=0.55 (20% EtOAc/hexanes). LCMS=565.3 (M+1)$^+$. $^1$H NMR (C$_6$D$_6$, 500 MHz, 70° C.) δ 7.63 (s, 1H), 7.43-7.38 (m, 3H), 7.17-7.13 (m, 3H), 6.86 (s, 1H), 6.74 (d, J=8.5 Hz, 1H), 4.37 (broad singlet, 2H), 4.08 (broad singlet, 2H), 3.45 (s, 3H), 3.40 (s, 3H), 2.80 (m, 1H), 1.18 (d, J=7.0 Hz, 6H).

Example 37

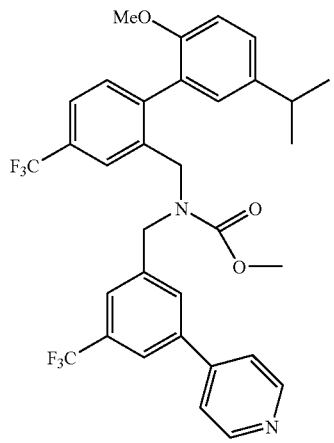

Methyl{[5'-isopropyl-2'-methoxy-4-(trifluoromethyl)biphenyl-2-yl]methyl}[3-pyridin-4-yl-5-(trifluoromethyl)benzyl]carbamate Methyl[3-iodo-5-(trifluoromethyl)benzyl]{[5'-isopropyl-2'-methoxy-4-(trifluoromethyl)biphenyl-2-yl]methyl}carbamate (Example 119, 20 mg, 0.03 mmol) and pyridine-4-boronic acid (4.6 mg, 0.04 mmol) were placed in a microwave tube, and dissolved with dimethyl ethylene glycol (170 μL). Next, 2M Na$_2$CO$_3$ (38 μL), ethanol (42 μL), and water (56 μL) were added. The solution was degassed with nitrogen for 2 minutes. Pd(PPh$_3$)$_4$ (3.5 mg, 0.003 mmol) was added and the solution was degassed with nitrogen again for 2 minutes. The solution was sealed and placed in a microwave reactor. The wattage was set for 60 W until the temperature reached 150° C. and then the temperature was held at 150° C. for twenty minutes. The mixture was then cooled to room temperature, poured into H$_2$O (10 mL), and extracted with EtOAc (30 mL). The organic layer was washed with brine (10 mL), dried over Na$_2$SO$_4$, filtered, and concentrated. Purification by flash chromatography with 5% to 80% EtOAc/hexanes afforded methyl{[5'-isopropyl-2'-methoxy-4-(trifluoromethyl)biphenyl-2-yl]methyl}[3-pyridin-4-yl-5-(trifluoromethyl)benzyl]carbamate. R$_f$=0.40 (75% EtOAc/hexanes). LCMS=617.3 (M+1)$^+$. $^1$H NMR (C$_6$D$_6$, 500 MHz, 70° C.) δ 8.54 (broad singlet, 2H), 7.70 (s, 1H), 7.51 (s, 1H), 7.38 (s, 1H), 7.35 (d, J=8.0, 1H), 7.28 (s, 1H), 7.06 (d, J=8.0, 1H), 7.02 (dd, J=2.0 Hz, 8.5, 1H), 6.89 (m, 2H), 6.83 (d, J=2.0, 1H), 6.58 (d, J=8.5, 1H), 4.45 (broad singlet, 2H), 4.13 (broad singlet, 2H), 3.38 (s, 3H), 3.23 (s, 3H), 2.65 (m, 1H), 1.12 (d, J=7.0 Hz, 6H).

Example 38

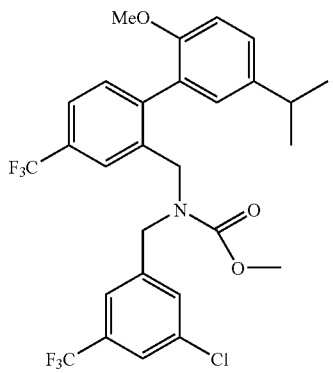

Methyl[3-chloro-5-(trifluoromethyl)benzyl]{[5'-isopropyl-2'-methoxy-4-(trifluoromethyl)biphenyl-2-yl]methyl}carbamate To a solution of CuCl$_2$ (11.9 mg, 0.09 mmol) in acetonitrile (1 mL) was added t-butyl nitrite (11 μL, 0.092 mmol). Next, the solution was cooled to 0° C. and methyl[3-amino-5-(trifluoromethyl)benzyl]{[5'-isopropyl-2'-methoxy-4-(trifluoromethyl)biphenyl-2-yl]methyl}carbamate (41 mg, 0.074 mmol) (Example 33) was added as a solution in acetonitrile (1.5 mL). The reaction was slowly warmed to room temperature. After stirring at room temperature for 2 hours, the mixture was diluted with EtOAc (30 mL) and poured into 20% HCl (5 mL). The organic extracts were washed with 20% HCl (2×5 mL), H$_2$O (10 mL), brine (10 mL), dried over Na$_2$SO$_4$, filtered, and concentrated. Purification by flash chromatography with 5% to 80% EtOAc/hexanes afforded methyl[3-chloro-5-(trifluoromethyl)benzyl]{[5'-isopropyl-2'-methoxy-4-(trifluoromethyl)biphenyl-2-yl]methyl}carbamate. R$_f$=0.65 (15% EtOAc/hexanes). LCMS=574.3 (M+1)$^+$. $^1$H NMR (C$_6$D$_6$, 500 MHz, 70° C.) δ 7.68 (s, 1H), 7.36 (d, J=7.5 Hz, 1H), 7.30 (s, 1H), 7.08-7.05 (m, 4H), 6.83 (d, J=2.5 Hz, 1H), 6.60 (d, J=8.5 Hz, 1H), 4.35 (broad singlet, 3H), 4.01 (broad singlet, 1H), 3.36 (s, 3H), 3.26 (s, 3H), 2.74 (m, 1H), 1.16 (d, J=7.0 Hz, 6H).

Example 39

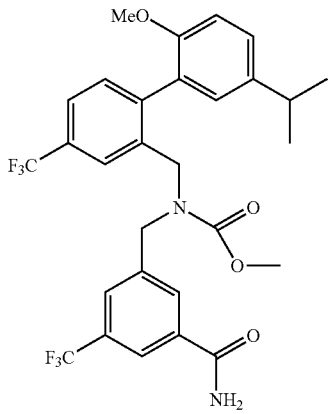

Methyl[3-(aminocarbonyl)-5-(trifluoromethyl)benzyl]{[5'-isopropyl-2'-methoxy-4-(trifluoromethyl)biphenyl-2-yl]methyl}carbamate A solution of methyl[3-cyano-5-(trifluoromethyl)benzyl]{[5'-isopropyl-2'-methoxy-4-(trifluoromethyl)biphenyl-2-yl]methyl}carbamate (35.0 mg, 0.06 mmol) (Example 36) in DMSO (248 μL) was cooled to 0° C. Next, K$_2$CO$_3$ (17.4 mg, 0.05 mmol) was added followed by 30% H$_2$O$_2$ (42.2 μL), and the reaction was slowly warmed to room temperature. After stirring at room temperature for 15 minutes, the mixture was diluted with EtOAc (50 mL) and poured into H$_2$O (15 mL). The organic extract was washed with brine (10 mL), dried over Na$_2$SO$_4$, filtered, and concentrated. Purification by flash chromatography with 5% to 80% EtOAc/hexanes afforded methyl[3-(aminocarbonyl)-5-(trifluoromethyl)benzyl]{[5'-isopropyl-2'-methoxy-4-(trifluoromethyl)biphenyl-2-yl]methyl}carbamate. R$_f$=0.45 (20% EtOAc/hexanes). LCMS=583.3 (M+1)$^+$. $^1$H NMR (C$_6$D$_6$, 500 MHz, 70° C.) δ 7.75 (s, 1H), 7.68 (s, 2H), 7.35 (s, 1H), 7.34 (s, 1H), 7.08-7.04 (m, 2H), 6.87 (d, J=2.5 Hz, 1H), 6.62 (d, J=8.5 Hz, 1H), 5.08 (broad singlet, 2H), 4.41 (broad singlet, 2H), 4.07 (broad singlet, 2H), 3.37 (s, 3H), 3.29 (s, 3H), 2.75 (m, 1H), 1.16 (d, J=7.5 Hz, 6H).

Example 40

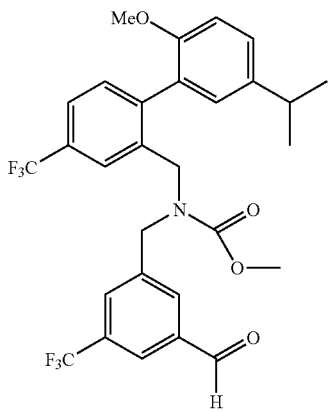

Methyl[3-formyl-5-(trifluoromethyl)benzyl]{[5'-isopropyl-2'-methoxy-4-(trifluoromethyl)biphenyl-2-yl]methyl}carbamate A mixture of methyl[3-cyano-5-(trifluoromethyl)benzyl]{[5'-isopropyl-2'-methoxy-4-(trifluoromethyl)biphenyl-2-yl]methyl}carbamate (150 mg, 0.26 mmol) (Example 36) and PtO$_2$ (30 mg, 0.132 mmol) in 88% formic acid (2 mL) was heated to 60° C. The reaction was stirred at this temperature for 4 hours. The reaction was then cooled to room temperature, diluted with hexanes (5 mL), loaded on a silica gel column, and purified with 5% to 25% EtOAc/hexanes to afford methyl[3-formyl-5-(trifluoromethyl)benzyl]{[5'-isopropyl-2'-methoxy-4-(trifluoromethyl)biphenyl-2-yl]methyl}carbamate. R$_f$=0.34 (25% EtOAc/hexanes). LCMS=568.2 (M+1)$^+$. $^1$H NMR (C$_6$D$_6$, 500 MHz, 70° C.) δ 9.40 (s, 1H), 7.67 (broad singlet, 1H), 7.64 (s, 1H), 7.50 (broad singlet, 1H), 7.39 (broad singlet, 1H), 7.35 (d, J=7.5 Hz, 1H), 7.07-7.03 (m, 2H), 6.85 (d, J=2.0 Hz, 1H), 6.60 (d, J=8.5 Hz, 1H), 4.40 (broad singlet, 2H), 4.03 (broad singlet, 2H), 3.38 (s, 3H), 3.26 (s, 3H), 2.73 (m, 1H), 1.15 (d, J=7.0 Hz, 6H).

Example 41

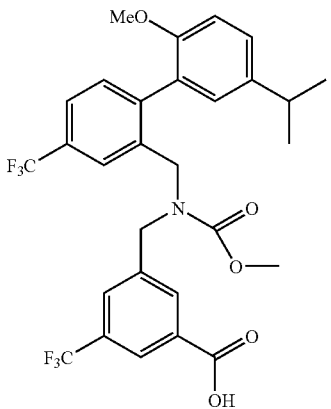

3-{[{[5'-Isopropyl-2'-methoxy-4-(trifluoromethyl)biphenyl-2-yl]methyl}-(methoxycarbonyl)amino]methyl}-5-(trifluoromethyl)benzoic acid To a solution of methyl[3-formyl-5-(trifluoromethyl)benzyl]{[5'-isopropyl-2'-methoxy-4-(trifluoromethyl)biphenyl-2-yl]methyl}carbamate (37.0 mg, 0.065 mmol) (Example 40) in THF (123 µL) was added t-butanol (360 µL), 2-methyl 2-butene (123 µL), and a solution of NaClO$_2$ (12.9 mg, 0.014 mmol) and NaH$_2$PO$_4$ (19.7 mg, 0.014 mmol) in H$_2$O (152 µL). The reaction was stirred vigorously for two hours at room temperature, diluted with EtOAc (30 mL), and poured into 1N HCl (10 mL). The aqueous layer was extracted with EtOAc (3×20 mL) and the combined organic extracts were washed with brine (10 mL), dried over Na$_2$SO$_4$, filtered, and concentrated. Purification by flash chromatography with 0.1% acetic acid in 8% MeOH/CH$_2$Cl$_2$ afforded 3-{[{[5'-isopropyl-2'-methoxy-4-(trifluoromethyl)biphenyl-2-yl]methyl}(methoxycarbonyl)amino]methyl}-5-(trifluoromethyl)benzoic acid. R$_f$=0.35 (10% MeOH/CH$_2$Cl$_2$). LCMS=584.3 (M+1)$^+$. $^1$H NMR (C$_6$D$_6$, 500 MHz, 70° C.) δ 8.28 (broad singlet, 1H), 8.04 (broad singlet, 1H), 7.68 (broad singlet, 1H), 7.37-7.34 (m, 2H), 7.07-7.05 (m, 2H), 6.87 (s, 1H), 6.62 (d, J=8.0 Hz, 1H), 4.43 (broad singlet, 2H), 4.41 (broad singlet, 2H), 3.40 (s, 3H), 3.29 (s, 3H), 2.75 (m, 1H), 1.17 (d, J=6.5 Hz, 6H).

Example 42

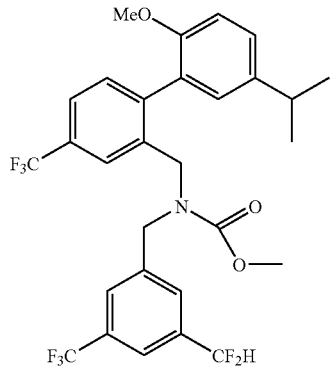

Methyl[3-(difluoromethyl)-5-(trifluoromethyl)benzyl]{[5'-isopropyl-2'-methoxy-4-(trifluoromethyl)biphenyl-2-yl]methyl}carbamate A solution of methyl[3-formyl-5-(trifluoromethyl)benzyl]{[5'-isopropyl-2'-methoxy-4-(trifluoromethyl)biphenyl-2-yl]methyl}carbamate (24.7 mg, 0.044 mmol) (Example 40) in CH$_2$Cl$_2$ (300 µL) was cooled to 0° C. DAST (92.8 µL, 9.6 mmol) was added and the reaction was slowly warmed to room temperature. After stirring at room temperature for 24 hours, the reaction was diluted with EtOAc (30 mL), and poured into NaHCO$_3$ (10 mL). The organic extract was washed with brine (10 mL), dried over Na$_2$SO$_4$, filtered, and concentrated. Purification by flash chromatography with 5% to 25% EtOAc/hexanes afforded methyl[3-(difluoromethyl)-5-(trifluoromethyl)benzyl]{[5'-isopropyl-2'-methoxy-4-(trifluoromethyl)biphenyl-2-yl]methyl}carbamate. R$_f$=0.42 (25% EtOAc/hexanes) LCMS=590.3 (M+1)$^+$. $^1$H NMR (C$_6$D$_6$, 500 MHz, 70° C.) δ 7.67 (broad singlet, 1H), 7.40 (s, 1H), 7.34 (d, J=7.5 Hz, 1H), 7.29 (broad singlet, 1H), 7.22 (broad singlet, 1H), 7.07-7.03 (m, 2H), 6.84 (d, J=2.0 Hz, 1H), 6.59 (d, J=8.5 Hz, 1H), 5.97 (t, J=56 Hz, 1H), 4.39 (broad singlet, 2H), 4.01 (broad singlet, 2H), 3.34 (s, 3H), 3.24 (s, 3H), 2.73 (m, 1H), 1.15 (d, J=7.0 Hz, 6H).

Example 43

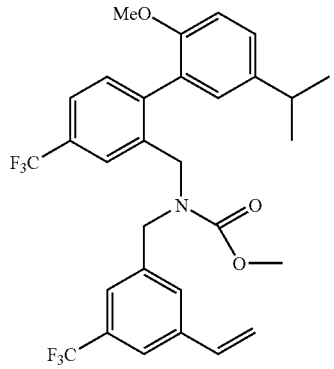

Methyl{[5'-isopropyl-2'-methoxy-4-(trifluoromethyl) biphenyl-2-yl]methyl}[3-(trifluoromethyl)-5-vinyl-benzyl]carbamate A suspension of Ph₃PCH₃Br (53.4 mg, 0.15 mmol) in THF (500 μL) was cooled to 0° C. potassium bis(trimethylsilyl) amide (256 μL of a 0.5 M solution in toluene, 0.128 mmol) was added slowly and the reaction was kept at 0° C. After fifteen minutes, methyl[3-formyl-5-(trifluoromethyl)benzyl] {[5'-isopropyl-2'-methoxy-4-(trifluoromethyl)biphenyl-2-yl]methyl}carbamate (24.2 mg, 0.043 mmol) (Example 40) was dissolved in THF (1 mL) and was added via cannula to the reaction which was then slowly warmed to room temperature. After fifteen minutes at room temperature, the reaction was diluted with EtOAc (30 mL), and poured into NaHCO₃ (10 mL). The organic extract was washed with brine (10 mL), dried over Na₂SO₄, filtered, and concentrated. Purification by flash chromatography with 5% to 25% EtOAc/hexanes afforded methyl{[5'-isopropyl-2'-methoxy-4-(trifluoromethyl)biphenyl-2-yl]methyl}[3-(trifluoromethyl)-5-vinyl-benzyl]carbamate. $R_f$=0.42 (25% EtOAc/hexanes) LCMS=566.2 (M+1)⁺. ¹H NMR (C₆D₆, 500 MHz, 70° C.) δ 7.68 (broad singlet, 1H), 7.36 (s, 1H), 7.34 (d, J=8.0 Hz, 1H), 7.15 (broad singlet, 1H), 7.10 (d, J=10.5 Hz, 1H), 7.03 (d, J=8.0 Hz, 1H), 7.01 (dd, J=8.5, 2.0 Hz, 1H), 6.81 (d, J=2.0 Hz, 1H), 6.54 (d, J=8.5 Hz, 1H), 6.32-6.27 (m, 1H), 5.40 (d, J=18 Hz, 1H), 4.97 (d, J=11 Hz, 1H), 4.37 (broad singlet, 2H), 4.04 (broad singlet, 2H), 3.34 (s, 3H), 3.20 (s, 3H), 2.69 (m, 1H), 1.12 (d, J=7.0 Hz, 6H).

Example 44

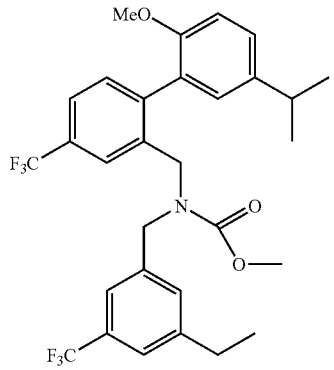

Methyl[3-ethyl-5-(trifluoromethyl)benzyl]{[5'-isopropyl-2'-methoxy-4-(trifluoromethyl)biphenyl-2-yl]methyl}carbamate A solution of methyl{[5'-isopropyl-2'-methoxy-4-(trifluoromethyl)biphenyl-2-yl]methyl}[3-(trifluoromethyl)-5-vinylbenzyl]carbamate (14 mg, 0.025 mmol) (Example 44) and Pd/C (5 mg) in THF (1 mL) and MeOH (500 μL) was placed under hydrogen. The reaction was stirred at room temperature under hydrogen for two hours. The reaction was then diluted with hexanes (25 mL), loaded on a silica gel column, and purified with 20% EtOAc/hexanes to afford methyl[3-ethyl-5-(trifluoromethyl)benzyl]{[5'-isopropyl-2'-methoxy-4-(trifluoromethyl)biphenyl-2-yl]methyl}carbamate. $R_f$=0.31 (25% EtOAc/hexanes). LCMS=568.3 (M+1)⁺. ¹H NMR (C₆D₆, 500 MHz, 70° C.) δ 7.72 (broad singlet, 1H), 7.34 (d, J=7.5 Hz, 1H), 7.20 (s, 1H), 7.10 (s, 1H), 7.07 (d, J=8.0 Hz, 1H), 7.01 (dd, J=2.0 Hz, 8.5, 1H), 7.01 (broad singlet, 1H), 6.86 (d, J=2.5 Hz, 1H), 6.59 (d, J=8.5 Hz, 1H), 4.44 (broad singlet, 2H), 4.11 (broad singlet, 2H), 3.39 (s, 3H), 3.24 (s, 3H), 2.73 (m, 1H), 2.25 (q, J=7.5 Hz, 2H), 1.15 (d, J=7.0 Hz, 6H), 0.92 (t, J=7.5 Hz, 3H).

Example 45

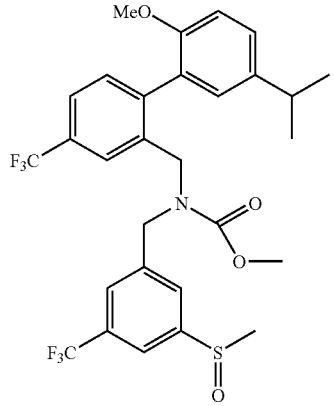

Methyl{[5'-isopropyl-2'-methoxy-4-(trifluoromethyl) biphenyl-2-yl]methyl}[3-(methylsulfinyl)-5-(trifluoromethyl)benzyl]carbamate Methyl{[5'-isopropyl-2'-methoxy-4-(trifluoromethyl)biphenyl-2-yl]methyl}[3-(methylthio)-5-(trifluoromethyl) benzyl]carbamate (21.7 mg, 0.037 mmol) (Example 129) in CH₂Cl₂ (1 mL) was cooled to −78° C. Next, m-CPBA (8.3 mg, 0.037 mmol) was added. The reaction was stirred at −78° C. for fifteen minutes, then was warmed to 45° C., and after five minutes at −45° C. was poured into NaHSO₃ (10 mL). The mixture was extracted with EtOAc (50 mL), and the organic extracts were washed with water (10 mL), brine (10 mL), dried over Na₂SO₄, filtered, and concentrated. Purification by flash chromatography with 50% EtOAc/hexanes afforded methyl{[5'-isopropyl-2'-methoxy-4-(trifluoromethyl)biphenyl-2-yl]methyl}[3-(methylsulfinyl)-5-(trifluoromethyl)benzyl]carbamate. $R_f$=0.20 (50% EtOAc/hexanes). LCMS=602.2 (M+1)⁺. ¹H NMR (C₆D₆, 500 MHz, 70° C.) δ 7.63 (broad singlet, 1H), 7.54 (broad singlet, 1H), 7.48 (broad singlet, 1H), 7.33 (s, 1H), 7.32 (s, 1H), 7.07-7.05 (m, 2H), 6.89 (s, 1H), 6.62 (d, J=8.0 Hz, 1H), 4.41 (broad singlet, 2H), 4.04 (broad singlet, 2H), 3.37 (s, 3H), 3.30 (s, 3H), 2.75 (m, 1H), 1.93 (s, 3H), 1.16 (d, J=6.5 Hz, 6H).

Example 46

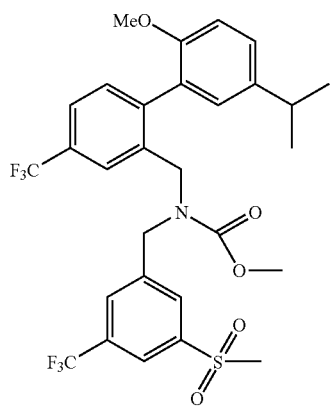

Methyl{[5'-isopropyl-2'-methoxy-4-(trifluoromethyl)biphenyl-2-yl]methyl}[3-(methylsulfonyl)-5-(trifluoromethyl)benzyl]carbamate Methyl{[5'-isopropyl-2'-methoxy-4-(trifluoromethyl)biphenyl-2-yl]methyl}[3-(methylthio)-5-(trifluoromethyl)benzyl]carbamate (18.0 mg, 0.031 mmol) (Example 129) in $CH_2Cl_2$ (1 mL) was cooled to 0° C. Next, m-CPBA (17.3 mg, 0.078 mmol) was added. The reaction was stirred at 0° C. for fifteen minutes and then was poured into $NaHSO_3$ (10 mL). The mixture was extracted with EtOAc (50 mL), and the organic extracts were washed with water (10 mL), brine (10 mL), dried over $Na_2SO_4$, filtered, and concentrated. Purification by flash chromatography with 50% EtOAc/hexanes afforded methyl{[5'-isopropyl-2'-methoxy-4-(trifluoromethyl)biphenyl-2-yl]methyl}[3-(methylsulfonyl)-5-(trifluoromethyl)benzyl]carbamate. $R_f$=0.61 (50% EtOAc/hexanes). LCMS=618.2 $(M+1)^+$. $^1$H NMR ($C_6D_6$, 500 MHz, 70° C.) δ 8.01 (s, 1H), 7.73 (s, 1H), 7.59 (broad singlet, 1H), 7.44 (broad singlet, 1H), 7.32 (d, J=8.0 Hz, 1H), 7.06 (s, 1H), 7.05 (s, 1H), 6.87 (d, J=2.5 Hz, 1H), 6.63 (d, J=8.5 Hz, 1H), 4.39 (broad singlet, 2H), 3.96 (broad singlet, 2H), 3.36 (s, 3H), 3.31 (s, 3H), 2.75 (m, 1H), 2.20 (s, 3H), 1.16 (d, J=7.0Hz, 6H).

Example 47

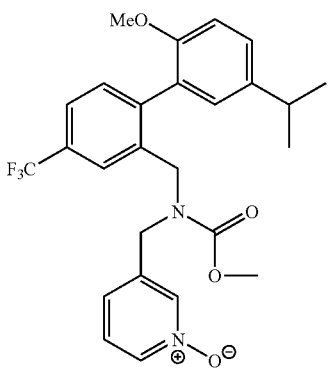

Methyl{[5'-isopropyl-2'-methoxy-4-(trifluoromethyl)biphenyl-2-yl]methyl}[(1-oxidopyridin-3-yl)methyl]carbamate To a solution of methyl{[5'-isopropyl-2'-methoxy-4-(trifluoromethyl)biphenyl-2-yl]methyl}(pyridin-3-ylmethyl)carbamate (12 mg, 0.025 mmol) (Example 123) in $CH_2Cl_2$ (400 μL) was added m-CPBA (28 mg, 0.13 mmol). The reaction was stirred at room temperature for two hours and then was poured into $NaHSO_3$ (10 mL). The mixture was extracted with EtOAc (50 mL), and the organic extracts were washed with water (10 mL), brine (10 mL), dried over $Na_2SO_4$, filtered, and concentrated. Purification by flash chromatography with 10 to 20% MeOH/EtOAc afforded methyl{[5'-isopropyl-2'-methoxy-4-(trifluoromethyl)biphenyl-2-yl]methyl}[(1-oxidopyridin-3-yl)methyl]carbamate. $R_f$=0.36 (20% MeOH/EtOAc). LCMS=489.2 $(M+1)^+$. $^1$H NMR ($C_6D_6$, 500 MHz, 70° C.) δ 6.21-8.22 (m, aromatics, 10H), 4.32 (s, 2H), 3.77 (s, 2H), 3.37 (s, 3H), 3.17 (s, 3H), 2.89 (m, 1H), 1.19 (d, J=7.0 Hz, 6H).

Example 48

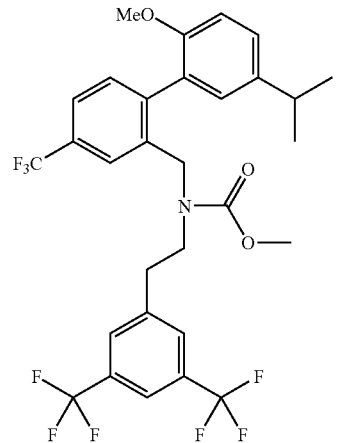

Methyl{2-[3,5-bis(trifluoromethyl)phenyl]ethyl}{[5'-isopropyl-2'-methoxy-4-(trifluoromethyl)biphenyl-2-yl]methyl}carbamate Step A 2-[3,5-Bis(trifluoromethyl)phenyl]-N-{[5'-isopropyl-2'-methoxy-4-(trifluoromethyl)biphenyl-2-yl]methyl}acetamide A solution of 3,5-bis(trifluoromethyl)phenylacetic acid (105.3 mg, 0.387 mmol) in $CH_2Cl_2$ (5 mL) was cooled to 0° C. N,N-diisopropylethylamine (169 μL, 0.968 mmol) was added, followed by HATU (139 mg, 0.3667 mmol). The reaction was stirred at 0° C. for 2 minutes and then a solution of 1-[5'-isopropyl-2'-methoxy-4-(trifluoromethyl)biphenyl-2-yl]methanamine (62.5 mg, 0.193 mmol) in $CH_2Cl_2$ (2 mL) was added. The reaction was stirred for 1 hour at 0° C. and then diluted with EtOAc (75 mL). The organics were washed with saturated $NaHCO_3$ and brine (25 mL each), dried over $Na_2SO_4$, filtered, and concentrated. Purification of the residue by flash chromatography with 100% $CH_2Cl_2$ gave 2-[3,5-bis(trifluoromethyl)phenyl]-N-{[5'-isopropyl-2'-methoxy-4-(trifluoromethyl)biphenyl-2-yl]methyl}acetamide. $R_f$=0.26 (25% EtOAc/hexanes). LCMS=578.2 $(M+1)^+$. $^1$H NMR ($CDCl_3$, 500 MHz) δ 7.79 (s, 1H), 7.70 (s, 2H), 7.59 (m, 2H), 7.33 (d, J=8.5 Hz, 1H), 7.25 (m, 1H), 6.97 (d, J=2.0 Hz, 1H), 6.91 (d, J=8.5 Hz, 1H), 5.84 (bs, 1H), 4.48 (dd, J=15.1, 6.6 Hz, 1H), 4.20 (dd, J=14.9, 4.3 Hz, 1H), 3.69 (s, 3H), 3.55 (s, 2H), 2.88 (m, 1H), 1.24 (d, J=6.8 Hz, 6H).

Step B: 2-[3,5-Bis(trifluoromethyl)phenyl]ethyl{[5'-isopropyl-2'-methoxy-4-(trifluoromethyl)biphenyl-2-yl]methyl}amine To a solution of 2-[3,5-bis(trifluoromethyl)phenyl]-N-{[5'-isopropyl-2'-methoxy-4-(trifluoromethyl)biphenyl-2-yl]methyl}acetamide (77.6 mg, 0.134 mmol) in THF (4.4 mL) was added $BH_3$ (1.34 mL of a 1M solution in THF, 1.34 mmol). The reaction was stirred overnight at room temperature and then 1 N HCl (10 mL) was added. The mixture was stirred for 5 minutes and then adjusted to a slightly basic pH with 1 N NaOH. The mixture was then extracted with $CH_2Cl_2$ (4×20 mL). The organic extracts were dried over $Na_2SO_4$, filtered, and concentrated. Purification of the residue by flash chromatography with 25 to 40% EtOAc/hexanes gave {2-[3,5-bis(trifluoromethyl)phenyl]ethyl}{[5'-isopropyl-2'-methoxy-4-(trifluoromethyl)biphenyl-2-yl]methyl}amine. R$_f$=0.17 (25% EtOAc/hexanes). LCMS=564.3 (M+1)$^+$. $^1$H NMR (CD$_2$Cl$_2$, 500 MHz) δ 7.75 (s, 1H), 7.73 (s, 1H), 7.64 (s, 2H), 7.53 (d, J=8.0 Hz, 1H), 7.30 (d, J=8.0 Hz, 1H), 7.24 (dd, J=8.2, 2.0 Hz, 1H), 6.98 (d, J=2.3 Hz, 1H), 6.91 (d, J=8.5 Hz, 1H), 3.58-3.73 (m, 5H), 2.88 (m, 1H), 2.74-2.81 (m, 4H), 1.22 (d, J=6.9 Hz, 6H).

Step C: Methyl{2-[3,5-bis(trifluoromethyl)phenyl]ethyl}{[5'-isopropyl-2'-methoxy-4-(trifluoromethyl)biphenyl-2-yl]methyl}carbamate To a solution of amine {2-[3,5-bis(trifluoromethyl)phenyl]ethyl}{[5'-isopropyl-2'-methoxy-4-(trifluoromethyl)biphenyl-2-yl]methyl}amine (16.6 mg, 0.0295 mmol) in CH$_2$Cl$_2$ (2 mL) was added methyl chloroformate (5 µL, 0.059 mmol) followed by N,N-diisopropylethylamine (20 µL, 0.116 mmol). The reaction was stirred at room temperature for 30 minutes and then poured into saturated NaHCO$_3$ (15 mL). The mixture was extracted with EtOAc (40 mL) and the organic layer was washed with brine (20 mL), dried over Na$_2$SO$_4$, filtered, and concentrated. Purification by flash chromatography with 25% EtOAc/hexanes yielded methyl{2-[3,5-bis(trifluoromethyl)phenyl]ethyl}{[5'-isopropyl-2'-methoxy-4-(trifluoromethyl)biphenyl-2-yl]methyl}carbamate. R$_f$=0.24 (25% EtOAc/hexanes). LCMS=622.2 (M+1)$^+$. $^1$H NMR (C$_6$D$_6$ at 70° C., 600 MHz) δ 7.74 (bs, 1H), 7.62 (s, 1H), 7.36 (d, J=7.0Hz, 1H), 7.22 (s, 2H), 7.07 (m, 2H), 6.88 (s, 1H), 6.63 (d, J=8.1 Hz, 1H), 4.30 (bs, 2H), 3.34 (s, 3H), 3.25 (s, 3H), 2.97-3.04 (m, 2H), 2.75 (m, 1H), 2.33 (bs, 2H), 1.17 (d, J=6.4 Hz, 6H).

Example 49

Methyl[3,5-bis(trifluoromethyl)benzyl][2-cyano-5-(trifluoromethyl)benzyl]carbamate To a solution of Example 5 dissolved in DMF (1.5 mL) was added CuCN (20 mg, 0.22 mmol) and the resultant mixture was heated at 100° C. for 16 h. The reaction was cooled to room temperature, poured into NH$_4$OH (10 mL) and extracted with EtOAC (4×30 mL). The combined organic extracts were washed with H$_2$O and brine (10 mL each), dried over MgSO$_4$, filtered and concentrated in vacuo. Purification by flash chromatography (0 to 25% EtOAc/hexanes) afforded the title compound as a colorless oil. LCMS=485 (M+1)$^+$. $^1$H NMR (CDCl$_3$, 500 MHz): δ 7.81 (s, 1H), 7.78 (d, J=7.7 Hz, 1H), 7.67-7.31 (m, 4H), 4.82 (br s, 2H), 4.72 (s, 2H), 3.91 (s, 3H).

Example 50

Methyl[3,5-bis(trifluoromethyl)benzyl][2-formyl-5-(trifluoromethyl)benzyl]carbamate Example 49 (85 mg, 0.18 mmol) was dissolved in 80% aqueous formic acid (5 mL) and platinum oxide (80% hydrate, 4.0 mg, 0.018 mmol) was added in one portion. The reaction was heated at 60° C. for 16 h and the platinum removed by filtration. H$_2$O (15 mL) was added and the mixture extracted with diethyl ether (4×30 mL). The combined organic extracts were washed with H$_2$O and brine (10 mL each), dried over Na$_2$SO$_4$, filtered and concentrated in vacuo. Purification by flash chromatography (0 to 25% EtOAc/hexanes) gave the title compound as a colorless oil. LCMS=488 (M+1)$^+$. $^1$H NMR (CDCl$_3$, 500 MHz): δ 10.21 (s, 1H), 7.96 (d, J=8.0 Hz, 1H), 7.81 (s, 1H), 7.79 (d, J=8.0 Hz, 1H), 7.72-7.55 (m, 3H), 5.18 (br, s, 2H), 4.78 (br s, 2H), 3.85 (s, 3H).

Following the procedures outlined for Examples 1-50 the compounds listed in Tables 2-5 were prepared.

TABLE 2

| Example | A$^1$ | LC/MS Data |
|---|---|---|
| 51 | 2-MeO-phenyl | 566.3 |
| 52 | 2-MeO-4-methylphenyl | 564.1 |
| 53 | 2-MeO-4-Cl-phenyl | 600.3 |
| 54 | 2-methylphenyl | 550.3 |
| 55 | 2-Cl-phenyl | 570.2 |
| 56 | 2,4-diCl-phenyl | 604.0 |
| 57 | 2-EtO-4-methylphenyl | 594.3 |

TABLE 2-continued

| Example | A¹ | LC/MS Data |
|---|---|---|
| 58 | 2-MeO, 4-F phenyl | 584.3 |
| 59 | 2-MeO, 3-F, 5-F phenyl | 602.0 |
| 60 | 5-MeO, 3-F, 4-F phenyl | 602.0 |
| 61 | 2-MeO, 5-OMe phenyl | 596.3 |
| 62 | 2-MeO, 5-isopropyl phenyl | 608.3 |
| 63 | 3-OMe phenyl | 588. (M + Na) |
| 64 | 2-MeO, 4-F phenyl | 584.4 |
| 65 | 2-Me, 5-OMe phenyl | 602.4 (M + Na) |
| 66 | 2-MeO, 4-OMe phenyl | 618. (M + Na) |
| 67 | 2-Me, 5-Me phenyl | 564.4 |
| 68 | 2-MeO, 5-CF₃ phenyl | 634 |
| 69 | 2-MeO, 5-propyl phenyl | 608.1 |
| 70 | 2-MeO, 5-tBu phenyl | 622.0 |
| 71 | 2-Me, 4-Me, 5-Me phenyl | 578.1 |
| 72 | 2-SMe phenyl | 604.3 |
| 73 | 4-MeO, 3-CHO phenyl | 594.3 |

TABLE 2-continued

| Example | A¹ | LC/MS Data |
|---------|----|----|
| 74 | MeO, F, isopropyl-substituted phenyl | 626.1 |
| 75 | MeO, F, methyl-substituted phenyl | 598.0 |
| 76 | 8-methylquinolin-5-yl | 601.3 |
| 77 | quinolin-6-yl | 587.2 |
| 78 | 8-methoxyquinolin-5-yl | 617.2 |
| 79 | 2-methoxypyridin-3-yl | 567.2 |
| 79a | 2-methoxy-5-trifluoromethylpyridin-3-yl | 635.0 |
| 80 | quinolin-8-yl | 587.2 |
| 81 | quinolin-3-yl | 587.2 |
| 82 | Cl, F, methyl-substituted phenyl | 602.1 |
| 83 | isoquinolin-5-yl | 587.2 |
| 84 | quinolin-5-yl | 587.2 |
| 85 | 1H-indol-5-yl | 597.2 |

TABLE 2-continued

| Example | A¹ | LC/MS Data |
|---|---|---|
| 86 | 2,3-dihydrobenzofuran-5-yl | 600.2 |
| 87 | thiophen-2-yl | 542 |
| 88 | 5-chlorothiophen-2-yl | 576 |
| 89 | furan-2-yl | 526 |
| 90 | 4-methylthiophen-3-yl | 556 |
| 91 | phenyl | 536.2 |
| 92 | 5-methylthiophen-2-yl | 556 |
| 93 | pyridin-3-yl | 537.2 |
| 94 | 4-methoxypyridin-3-yl | 567.2 |
| 95 | 4-methylthiophen-2-yl | 556 |
| 96 | 2-ethylphenyl | 564.4 |
| 97 | 4-methoxy-3-vinylphenyl | 592.2 |
| 98 | thiophen-3-yl | 542 |
| 99 | 3,5-dimethylisoxazol-4-yl | 555 |
| 100 | pyridin-4-yl | 537.2 |
| 101 | 3-methoxy-6-methylpyridin-2-yl | 581.2 |

TABLE 2-continued

[Structure: benzyl group with A¹ and CF₃ substituents, connected via N-CH₂ to 3,5-bis(trifluoromethyl)benzyl, with methyl carbamate on N]

| Example | A¹ | LC/MS Data |
|---|---|---|
| 101a | 3-MeO, 6-isopropyl pyridin-2-yl | 609.2 |
| 102 | 5-acetyl-thiophen-2-yl | 584 |

TABLE 3

[Structure: benzyl group with A¹ and R² substituents, connected via N-CH₂ to 3,5-bis(trifluoromethyl)benzyl, with methyl carbamate on N]

| EXAMPLE | A¹ | R² | LC/MS |
|---|---|---|---|
| 103 | 2-MeO-5-methyl-phenyl | OMe | 564.4 (M + Na) (4.40) |
| 104 | 2-MeO-5-isopropyl-phenyl | OMe | 592.4 (M + Na) (4.60) |
| 105 | 2-MeO-5-isopropyl-phenyl | F | 558.4 (M + 1) (4.62) |
| 106 | 2-MeO-5-propyl-phenyl | F | 558.4 (M + 1) (4.64) |
| 107 | 2-MeO-5-tert-butyl-phenyl | F | 572.5 (M + 1) (4.68) |
| 108 | 2-MeO-5-methyl-phenyl | H | 512.2 (M + 1) (4.56) |
| 108a | 5-MeO-2-fluoro-4-methyl-phenyl | Cl | 564.0 (M + 1) (4.57) |
| 109 | 2-MeO-5-isopropyl-phenyl | H | 540.2 (M + 1) (4.76) |
| 110 | 5-MeO-2-fluoro-4-isopropyl-phenyl | Cl | 592.2 (M + 1) (4.74) |

TABLE 4
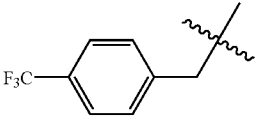
| EXAMPLE | Q | LC/MS Data |
|---|---|---|
| 111 | 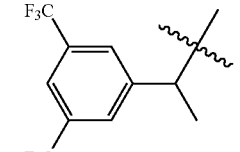 | 540.3 (M + 1) |
| 112 | 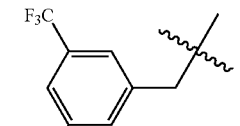 | 622.3 (M + 1) |
| 113 | 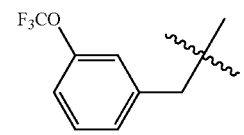 | 558.3 (M + 1) |
| 114 | 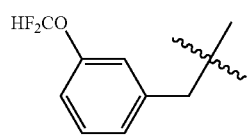 | 556.3 (M + 1) |
| 115 | 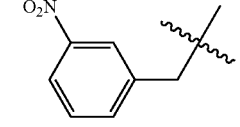 | 538.3 (M + 1) |
| 116 | 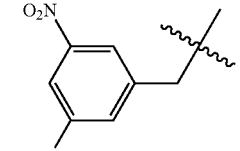 | 517.3 (M + 1) |
| 117 | 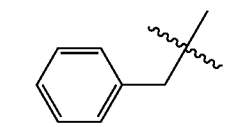 | 562.2 (M + 1) |
| 118 | 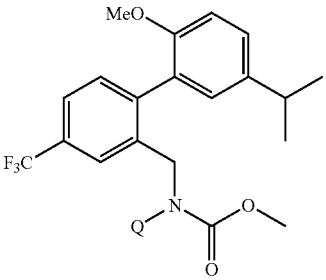 | 472.4 (M + 1) |
TABLE 4-continued
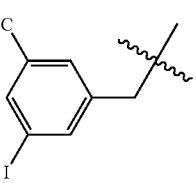
| EXAMPLE | Q | LC/MS Data |
|---|---|---|
| 119 | 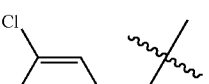 | 666.2 (M + 1) |
| 120 |  | 540.2 (M + 1) |
| 121 | 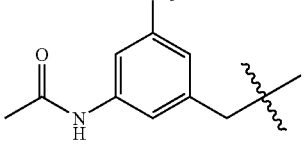 | 597.4 (M + 1) |
| 122 | 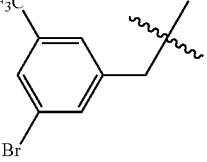 | 620.2 (M + 1) |
| 123 | 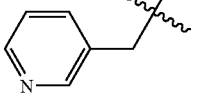 | 473.2 (M + 1) |
| 124 | 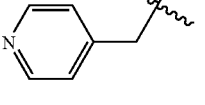 | 473.3 (M + 1) |
| 125 | | 473.3 (M + 1) |

TABLE 4-continued

| EXAMPLE | Q | LC/MS Data |
|---|---|---|
| 126 | 3,5-dimethylbenzyl | 500.3 (M + 1) |
| 127 | thiophen-2-ylmethyl | 478.2 (M + 1) |
| 128 | cyclohexylmethyl | 478.3 (M + 1) |
| 129 | 3-(methylthio)-5-(trifluoromethyl)benzyl | 586.2 (M + 1) |
| 130 | 3-methoxy-5-(trifluoromethyl)benzyl | 570.2 (M + 1) |

TABLE 5

| EXAMPLE | Z | LCMS (M + 1)$^+$ |
|---|---|---|
| 131 | propanoyl | 606.3 |
| 132 | N,N-dimethylcarbamoyl | 621.4 |
| 133 | (methylthio)carbonyl | 624.3 |

Example 134

Methyl [3,5-bis(trifluoromethyl)benzyl][2-isoquinolin-4-yl-5-(trifluoromethyl)benzyl]carbamate To a solution of methyl [3,5-bis(trifluoromethyl)benzyl] (2-iodo-5-trifluoromethyl-benzyl)carbamate (41 mg, 0.070 mmol) (Example 5) in 3:2 EtOH:toluene, 4-isoquinolineboronic acid (18.2 mg, 0.105 mmol) and 2.5 M sodium carbonate (0.175 mmol) were added. The solution was degassed, followed by the addition of a catalytic amount of tetrakis(triphenylphosphine)palladium. The solution was stirred at 95-100° C. until completion of the reaction. Upon cooling, the solvent was removed in vacuo. The desired product was obtained by preparative thin layer chromatography using 25% acetone/hexane. $^1$H NMR (CDCl$_3$, 500 MHz) δ 9.36 (s, 1H), 8.38 (s, 1H), 8.10-8.13 (m, 1H), 7.68-7.80 (m, 4H), 7.26-7.64 (m, 5H), 4.22-4.48 (m, 4H), 3.64-3.78 (m, 3H). LC-MS (M+1) 587.2 (3.48 min).

Example 135

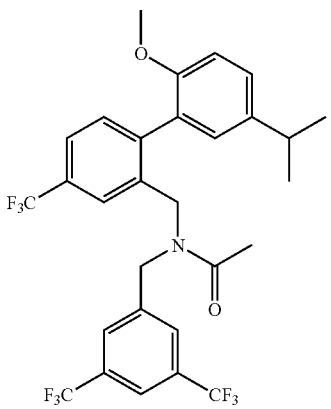

N-[3,5-Bis(trifluoromethyl)benzyl]-N-{[5'-isopropyl-2'-methoxy-4-trifluoromethyl)biphenyl-2-yl]methyl}acetamide Step A: N-[2-amino-5-(trifluoromethyl)benzyl]-N-[3,5-bis(trifluoromethyl)benzyl]-acetamide To a solution of [2-amino-5-(trifluoromethyl)benzyl][3,5-bis(trifluoromethyl)benzyl]amine (Example 3) (270 mg, 0.65 mmol) in methylene chloride at 0° C., acetic anhydride (0.061 mL, 0.65 mmol) in methylene chloride and then triethylamine were added (0.018 mL, 0.13 mmol). The solution was stirred for 0.5 hours at 0° C. This solution was washed with saturated sodium bicarbonate, dried over anhydrous sodium sulfate, filtered and concentrated. The title compound was purified by column chromatography using 40% EtOAC/hexane. $^1$H NMR (CDCl$_3$, 500 MHz) δ 7.80 (s, 1H), 7.56 (s, 2H), 7.30 (d, J=8.5 Hz, 1H), 7.04 (s, 1H), 6.65 (d, J=8.5 Hz, 1H), 4.67 (s, 2H), 4.65 (s, 2H), 2.22 (s, 3H).

Step B: N-[3,5-bis(trifluoromethyl)benzyl]-N-[2-iodo-5-(trifluoromethyl)benzyl]acetamide To a solution of the title compound from Step A (58 mg, 0.127 mmol) in chloroform at room temperature, n-amyl nitrite (0.025 mL, 0.191 mmol) was added. The solution was stirred for 5 minutes and then iodine (65 mg, 0.254 mmol) was added. This solution was stirred at 70° C. for 1 hour. Upon cooling to room temperature, the organic solution was washed with saturated sodium thiosulfate and brine, dried over anhydrous sodium sulfate, filtered and concentrated. The title compound was purified by column chromatography using 25% EtOAc/hexane. $^1$H NMR (CDCl$_3$, 500 MHz): a 1:2 mixture of rotamers δ 8.01 (d, J=8.0 Hz, 2/3H), 7.93 (d, J=8.0 Hz, 1/3H), 7.84 (s, 1/3H), 7.79 (s, 2/3H), 7.67 (s, 4/3H), 7.60 (s, 2/3H), 7.43 (s, 1/3H), 7.29 (d, J=8.0 Hz, 2/3H), 7.23 (m, 1H), 4.78 (s, 2/3H), 4.72 (s, 4/3H), 4.68 (s, 2/3H), 4.55 (s, 4/3H), 2.32 (s, 1H), 2.27 (s, 2H).

Step C: N-[3,5-Bis(trifluoromethyl)benzyl]-N-{[5'-isopropyl-2'-methoxy-4-(trifluoromethyl)biphenyl-2-yl]methyl}acetamide The title compound was prepared according to the procedure described in Example 6, but using (5-isopropyl-2-methoxyphenyl)boronic acid. $^1$H NMR (CDCl$_3$, 500 MHz): a mixture of 1:3 rotamers δ 7.76 (m, 1H), 7.58-7.63 (m, 2H), 7.24-7.37 (m, 3H), 6.8-6.94 (m, 3H), 3.69 (s, 9/4H), 3.62 (s, 3/4H), 2.79-2.91 (m, 1H), 2.09 (s, 3/4H), 2.01 (s, 9/4H), 1.15-1.26 (m, 6H). LC-MS (M+1) 592.0 (4.60 min).

Example 136

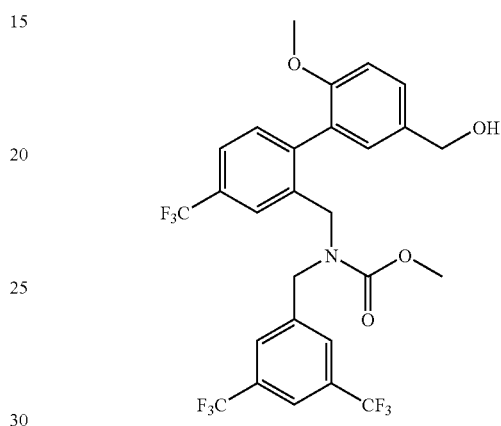

Methyl [3,5-bis(trifluoromethyl)benzyl]{[5'-(hydroxymethyl)-2'-methoxy-4-(trifluoromethyl)biphenyl-2-yl]methyl}carbamate Sodium borohydride (9.9 mg, 0.262 mmol) was added to a solution of methyl [3,5-bis(trifluoromethyl)benzyl]{[5'-formyl-2'-methoxy-4-(trifluoromethyl)biphenyl-2-yl]methyl}carbamate (Example 73, 78 mg, 0.131 mmol) in methanol at room temperature. The reaction was stirred for one hour, then solvent was removed in vacuo. The title compound was obtained by column chromatography using 3:7 acetone/hexane. $^1$H NMR (CDCl$_3$, 500 MHz) δ 7.25 (s, 1H), 7.30-7.62 (m, 6H), 7.08 (m, 1H), 6.94 (m, 1H), 4.64 (s, 2H), 4.15-4.40 (m, 4H), 3.64-3.74 (m, 6H). LC-MS (M-17) 578.0 (4.09 min).

Example 137

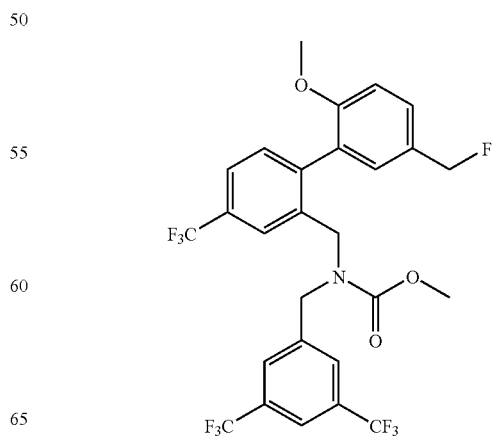

91

Methyl [3,5-bis(trifluoromethyl)benzyl]{[5'-(fluoromethyl)-2'-methoxy-4-(trifluoromethyl)biphenyl-2-yl]methyl}carbamate Diethylaminosulfur trifluoride (0.014 mL, 0.103 mmol) was added dropwise to a solution of methyl [3,5-bis(trifluoromethyl)benzyl]{[5'-(hydroxymethyl)-2'-methoxy-4-(trifluoromethyl)biphenyl-2-yl]methyl}carbamate (Example 136, 41 mg, 0.069 mmol) in anhydrous methylene chloride at 0° C. The reaction was gradually warmed to room temperature until the reaction was complete. At this time, the reaction was re-cooled to 0° C. and water was added. The organic layer was diluted with methylene chloride, washed with brine, dried over anhydrous sodium sulfate, filtered and concentrated. The title compound was purified by preparative thin layer chromatography using 15% acetone/hexane.

Example 138

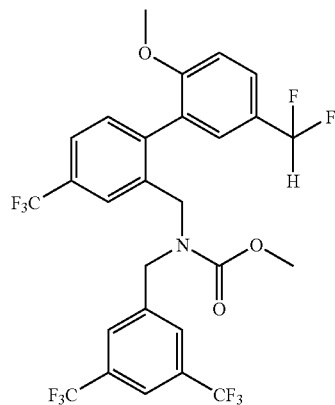

Methyl [3,5-bis(trifluoromethyl)benzyl]{[5'-(difluoromethyl)-2'-methoxy-4-(trifluoromethyl)biphenyl-2-yl]methyl}carbamate Diethylaminosulfur trifluoride (0.024 mL, 0.179 mmol) was added dropwise to a solution of methyl [3,5-bis(trifluoromethyl)benzyl]{[5'-formyl-2'-methoxy-4-(trifluoromethyl)biphenyl-2-yl]methyl}carbamate (Example 73, 53 mg, 0.089 mmol) in anhydrous methylene chloride at 0° C. The reaction was gradually warmed to room temperature until the reaction was complete. At this time, the reaction was re-cooled to 0° C., and water was added. The organic layer was diluted with methylene chloride, washed with brine, dried over anhydrous sodium sulfate, filtered and concentrated. The title compound was purified by column chromatography using 1:3 EtOAc:hexane. $^1$H NMR (CDCl$_3$, 500 MHz) δ 7.77 (s, 1H), 7.63 (d, J=7.5 Hz, 1H), 7.36-7.60 (m, 4H), 7.35 (d, J=8.0 Hz, 1H), 7.26 (s, 1H), 7.04 (d, J=7.5 Hz, 1H), 6.65 (t, J=56.5 Hz, 1H), 4.20-4.60 (m, 4H), 3.75 (m, 6H). LC-MS (M+Na) 638.3 (4.34 min).

92

Example 139

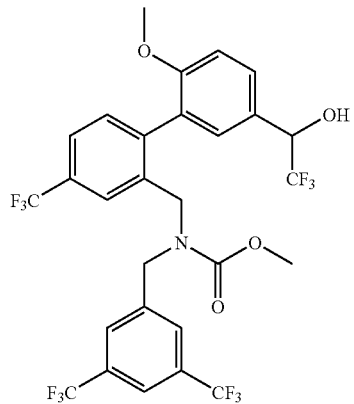

Methyl [3,5-bis(trifluoromethyl)benzyl]{[2'-methoxy-5'-(2,2,2-trifluoro-1-hydroxyethyl)-4-(trifluoromethyl)biphenyl-2-yl]methyl}carbamate To a solution of methyl [3,5-bis(trifluoromethyl)benzyl]{[5'-formyl-2'-methoxy-4-(trifluoromethyl)biphenyl-2-yl]methyl}carbamate (Example 73, 184 mg, 0.31 mmol) in anhydrous tetrahydrofuran at 0° C., 0.5 M trimethyl(trifluoromethyl) silane (2.5 mL, 1.24 mmol) and a catalytic amount of tetrabutylammonium fluoride were added. The reaction was stirred with gradual warming to room temperature. Once the reaction was complete, it was quenched with saturated ammonium chloride solution. The organic was extracted with methylene chloride, washed with brine, dried over anhydrous sodium sulfate, filtered and concentrated. The title compound was obtained by preparative thin layer chromatography using 1:4 acetone:hexane. $^1$H NMR (CDCl$_3$, 600 MHz) δ 7.74 (s, 1H), 7.61 (m, 1H), 7.15-7.56 (m, 6H), 6.99 (m, 1H), 4.97 (m, 1H), 4.19-4.38 (m, 4H), 3.61-3.76 (m, 6H). LC-MS (M+Na) 686.9 (4.28 min).

Example 140

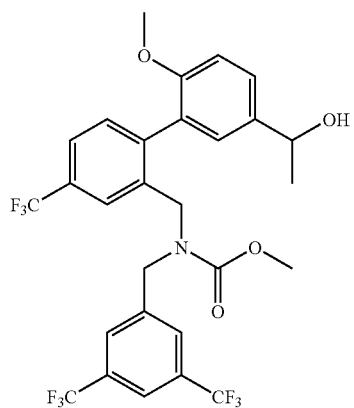

Methyl [3,5-bis(trifluoromethyl)benzyl]{[5'-(1-hydroxyethyl)-2'-methoxy-4-(trifluoromethyl)biphenyl-2-yl]methyl}carbamate Methylmagnesium bromide (0.59 mL, 0.83 mmol) was added dropwise to a solution of methyl [3,5-bis(trifluoromethyl)benzyl]{[5'-formyl-2'-methoxy-4-(trifluoromethyl)biphenyl-2-yl]methyl}carbamate (Example 73, 289 mg, 0.49 mmol) in anhydrous tetrahydrofuran at 0° C. The solution was allowed to warm to room temperature. Once the reaction was complete, saturated ammonium chloride solution was added to quench the reaction. The mixture was extracted with methylene chloride, washed with brine, dried over anhydrous sodium sulfate, filtered and concentrated. The title compound was obtained by flash chromatography using 30% acetone/hexane. $^1$H NMR (CDCl$_3$, 600 MHz) δ 7.73 (s, 1H), 7.58 (m, 1H), 7.32-7.51 (m, 5H), 7.11 (m, 1H), 6.94 (m, 1H), 4.87 (m, 1H), 4.25-4.43 (m, 4H), 3.69 (m, 6H), 1.48 (d, J=4.2 Hz, 3H). LC-MS (M+Na) 632.0 (4.18 min).

Example 141

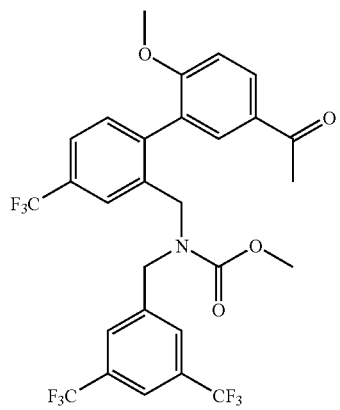

Methyl {[5'-acetyl-2'-methoxy-4-(trifluoromethyl)biphenyl-2-yl]methyl}[3,5-bis(trifluoromethyl)benzyl]carbamate Methyl [3,5-bis(trifluoromethyl)benzyl]{[5'-(1-hydroxyethyl)-2'-methoxy-4-(trifluoromethyl)biphenyl-2-yl]methyl}carbamate (Example 140, 29 mg, 0.048 mmol) was dissolved in methylene chloride, and Dess-Martin periodinane (31 mg, 0.072 mmol) was added. Once the reaction was complete, the solution was diluted in diethyl ether and washed sequentially with saturated sodium thiosulfate, saturated sodium bicarbonate and water. The aqueous extracts were combined and back extracted with diethyl ether then recombined with the previous organic layers. The combined organic layers were dried over anhydrous sodium sulfate, filtered and concentrated. The title compound was obtained by preparative thin layer chromatography using 2:3 EtOAc: hexane. $^1$H NMR (CDCl$_3$, 600 MHz) δ 8.02 (d, J=7.8 Hz, 1H), 7.76 (d, J=2.4 Hz, 1H), 7.73 (s, 1H), 7.61 (d, J=7.8 Hz, 1H), 7.32-7.55 (m, 4H), 6.99 (m, 1H), 4.18-4.58 (m, 4H), 3.79 (s, 3H), 3.69-3.76 (m, 3H), 2.57 (s, 3H). LC-MS (M+1) 608.3 (4.19 min).

Example 142

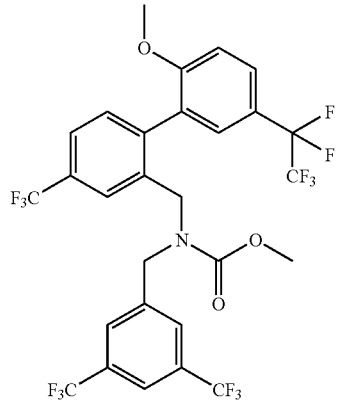

Methyl [3,5-bis(trifluoromethyl)benzyl]{[2'-methoxy-5'-(pentafluoroethyl)-4-(trifluoromethyl)biphenyl-2-yl]methyl}carbamate Step A: Methyl [3,5-bis(trifluoromethyl)benzyl]{[2'-methoxy-5'-(trifluoroacetyl)-4-(trifluoromethyl)biphenyl-2-yl]methyl}carbamate Methyl [3,5-bis(trifluoromethyl)benzyl]{[2'-methoxy-5'-(2,2,2-trifluoro-1-hydroxyethyl)-4-(trifluoromethyl)biphenyl-2-yl]methyl}carbamate (Example 139, 29 mg, 0.048 mmol) was dissolved in methylene chloride, and Dess-Martin periodinane (31 mg, 0.072 mmol) was added. Once the reaction was complete, the solution was diluted in diethyl ether and washed sequentially with saturated sodium thiosulfate, saturated sodium bicarbonate and water. The aqueous extracts were combined and back extracted with diethyl ether, then recombined with the previous organic layers. The combined organic layers were dried over anhydrous sodium sulfate, filtered and concentrated. The title compound was obtained by preparative thin layer chromatography using 1:3 acetone:hexane.

Step B: Methyl [3,5-bis(trifluoromethyl)benzyl]{[2'-methoxy-5'-(pentafluoroethyl)-4-(trifluoromethyl)biphenyl-2-yl]methyl}carbamate Diethylaminosulfur trifluoride (0.008 mL, 0.058 mmol) was added dropwise to a solution of Methyl [3,5-bis(trifluoromethyl)benzyl]{[2'-methoxy-5'-(trifluoroacetyl)-4-(trifluoromethyl)biphenyl-2-yl]methyl}carbamate (Step A) (19 mg, 0.029 mmol) in anhydrous methylene chloride at 0° C. The reaction was gradually warmed to room temperature until the reaction was complete. At this time, the reaction was re-cooled to 0° C., and water was added to quench. The organic layer was diluted with methylene chloride, washed with brine, dried over anhydrous sodium sulfate, filtered and concentrated. The desired product was purified by column chromatography using 30% EtOAc/hexane. $^1$H NMR (CDCl$_3$, 600 MHz) δ 7.74 (s, 1H), 7.60-7.66 (m, 2H), 7.28-7.54 (m, 5H), 7.06 (d, J=9.0 Hz, 1H), 4.16-4.59 (m, 4H), 3.80 (s, 3H), 3.68 (s, 3H).

Example 143

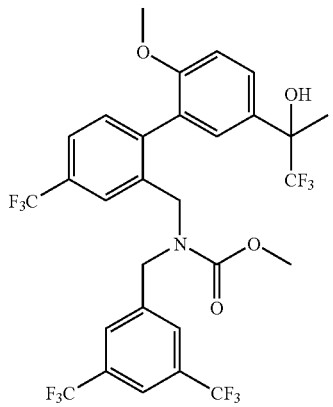

Methyl [3,5-bis(trifluoromethyl)benzyl]{[2'-methoxy-5'-(2,2,2-trifluoro-1-hydroxy-1-methylethyl)-4-(trifluoromethyl)biphenyl-2-yl]methyl}carbamate The title compound from Example 142, Step A (7 mg, 0.027 mmol) was dissolved in anhydrous THF at 0° C. Methylmagnesium bromide (0.023 mL, 0.032 mmol) was added dropwise, and the mixture was slowly warmed to room temperature. Once the reaction was complete, saturated ammonium chloride solution was added to quench the reaction. The mixture was extracted with methylene chloride, washed with brine, dried over anhydrous sodium sulfate, filtered and concentrated. The title compound was obtained by flash chromatography using 30% acetone/hexane. $^1$H NMR (CDCl$_3$, 600 MHz) δ 7.73 (s, 1H), 7.30-7.61 (m, 7H), 6.98 (m, 1H), 4.19-4.62 (m, 4H), 3.75 (s, 3H), 3.64-3.71 (m, 3H), 1.75-1.78 (m, 3H). LC-MS (M+Na) 699.8 (4.35 min).

Example 144

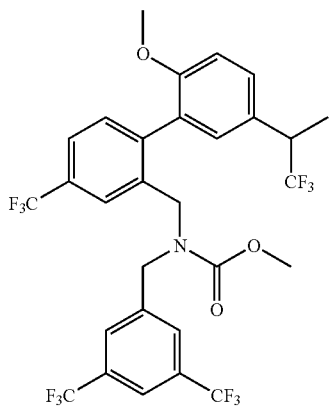

Methyl [3,5-bis(trifluoromethyl)benzyl]{[2'-methoxy-4-(trifluoromethyl)-5'-(2,2,2-trifluoro-1-methylethyl)biphenyl-2-yl]methyl}carbamate Step A: Methyl [3,5-bis(trifluoromethyl)benzyl]({2'-methoxy-4-(trifluoromethyl)-5'-[1-(trifluoromethyl)vinyl]biphenyl-2-yl}methyl)carbamate Methanesulfonyl chloride was added to the title compound from Example 143, Step A (45 mg, 0.068 mmol) in methylene chloride at 0° C. The solution was stirred at the same temperature until starting material was consumed. The solution was washed with water, then brine, dried over anhydrous sodium sulfate, filtered and concentrated. The product was purified by preparative thin layer chromatography using 15% EtOAc/hexane.

Step B:
The title compound from Step A (10 mg, 0.017 mmol) was hydrogenated at 1 atm in methanol using Pd/C as the catalyst. The solution was filtered through Celite then concentrated. The title compound was purified by preparative thin layer chromatography using 1:4 EtOAc:hexane.

Example 145

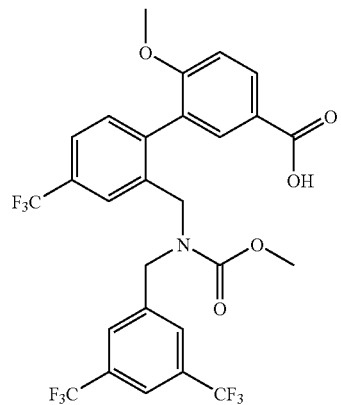

2'-{[[3,5-Bis(trifluoromethyl)benzyl](methoxycarbonyl)amino]methyl}-6-methoxy-4'-(trifluoromethyl)biphenyl-3-carboxylic acid Jones Reagent (0.10 mL, 0.382 mmol) was added to a solution of the title compound from Example 136, Step A (113 mg, 0.191 mmol) in acetone. The solution was stirred at room temperature. Upon completion of the reaction, i-PrOH was added to quench the reaction. The solution was filtered, and the filtrate was taken up in diethyl ether and water. The organic layer was separated, dried over anhydrous sodium sulfate, filtered and concentrated to give the title compound. $^1$H NMR (CDCl$_3$, 500 MHz) δ 8.16 (s, 1H), 7.84 (s, 1H), 7.74 (s, 1H), 7.63 (d, J=8.0 Hz, 1H), 7.45-7.58 (m, 3H), 7.35 (d, J=8.0 Hz, 1H), 7.02 (d, J=8.0 Hz, 1H), 4.20-4.60 (m, 4H), 3.82 (s, 3H), 3.74 (m, 3H). LC-MS (M+1) 609.9 (4.01 min).

Example 146

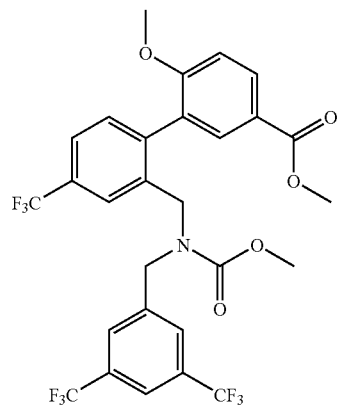

Methyl 2'-{[[3,5-bis(trifluoromethyl)benzyl](methoxycarbonyl)amino]methyl}-6-methoxy-4'-(trifluoromethyl)biphenyl-3-carboxylate (Trimethylsilyl)diazomethane (0.059 mL, 0.117 mmol) was added to a solution of the title compound from Example 135 (32 mg, 0.053 mmol) in diethyl ether at 0° C. The reaction was allowed to stir at room temperature until completion. It was quenched with a few drops of trifluoroacetic acid then concentrated. The title compound was obtained by preparative thin layer chromatography using 30% acetone/hexane. $^{1}$H NMR (CDCl$_{3}$, 600 MHz) δ 8.09 (s, 1H), 7.79 (s, 1H), 7.72 (s, 1H), 7.60 (d, J=8.4 Hz, 1H), 7.43-7.58 (m, 3H), 7.32 (d, J=7.8 Hz, 1H), 6.97 (m, 1H), 4.17-4.60 (m, 4H), 3.90 (s, 3H), 3.78 (s, 3H), 3.74 (m, 3H). LC-MS (M+Na) 645.9 (4.40 min).

Example 147

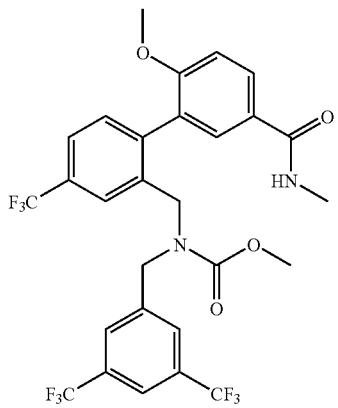

Methyl [3,5-bis(trifluoromethyl)benzyl]{[2'-methoxy-5'-[(methylamino)carbonyl]-4-(trifluoromethyl)biphenyl-2-yl]methyl}carbamate A mixture of the title compound from Example 145 (22 mg, 0.036 mmol), methylamine hydrochloride (3.6 mg, 0.054 mmol), 1-[3-(dimethylamino)propyl]-3-ethylcarbodiimide hydrochloride (10.3 mg, 0.054 mmol), 1-hydroxybenzotriazole hydrate (7.3 mg, 0.054 mmol) and diisopropylethylamine (0.02 mL, 0.108 mmol) were stirred in methylene chloride overnight at room temperature. The solvent was removed in vacuo. The title compound was obtained by preparative thin layer chromatography using 70% EtOAc/hexane. $^{1}$H NMR (CDCl$_{3}$, 600 MHz) δ 7.81 (d, J=7.2 Hz, 1H), 7.73 (s, 1H), 7.59 (d, J=7.8 Hz, 1H), 7.34-7.56 (m, 4H), 7.32 (d, J=7.8 Hz, 1H), 6.97 (d, J=7.8 Hz, 1H), 6.14 (br s, 1H), 4.19-4.42 (m, 4H), 3.76 (s, 3H), 3.65-3.73 (m, 3H), 3.00 (m, 3H). LC-MS (M+1) 622.9 (3.96 min).

Example 148

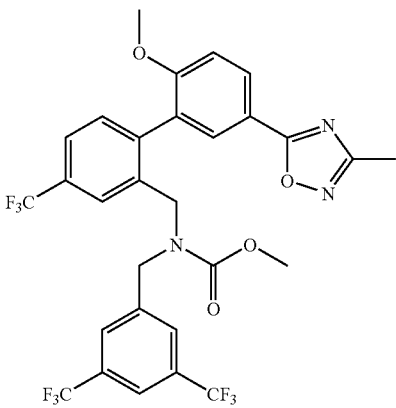

Methyl [3,5-bis(trifluoromethyl)benzyl]{[2'-methoxy-5'-(3-methyl-1,2,4-oxadiazol-5-yl)-4-(trifluoromethyl)biphenyl-2-yl]methyl}carbamate Oxalyl chloride (0.14 mL, 0.28 mmol) and a few drops of dimethylformamide were added to a solution of the title compound from Example 145 (86 mg, 0.14 mmol) in methylene chloride. The reaction mixture was stirred at room temperature for 1 h then concentrated in vacuo. The crude product was re-dissolved in anhydrous dichloroethane, and acetamide oxime (16 mg, 0.21 mmol) was added along with a few drops of dimethylformamide to increase solubility. The reaction was heated to and maintained at reflux overnight. Once the reaction cooled to room temperature, the solvent was removed through evaporation. The oil was taken up in methylene chloride, washed with water, then brine, dried over anhydrous sodium sulfate, filtered and concentrated. The title compound was obtained by preparative thin layer chromatography using 50% EtOAc/hexane. $^{1}$H NMR (CDCl$_{3}$, 600 MHz) δ 8.15 (s, 1H), 7.86 (s, 1H), 7.71 (s, 1H), 7.62 (d, J=8.4 Hz, 1H), 7.43-7.56 (m, 3H), 7.35 (d, J=7.8 Hz, 1H), 7.07 (m, 1H), 4.20-4.60 (m, 4H), 3.81 (s, 3H), 3.70 (m, 3H), 2.46 (s, 3H). LC-MS (M+1) 647.9 (4.40 min).

Example 149

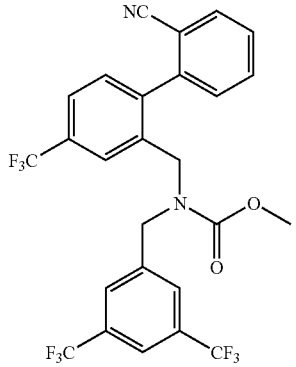

Methyl [3,5-bis(trifluoromethyl)benzyl]{[2'-cyano-4-(trifluoromethyl)biphenyl-2-yl]methyl}carbamate A mixture of methyl [3,5-bis(trifluoromethyl)benzyl](2-iodo-5-trifluoromethyl-benzyl)carbamate (29 mg, 0.050 mmol), 2-cyanophenylboronic acid (10.9 mg, 0.074 mmol), potassium fluoride (8.7 mg, 0.149 mmol), 2-dicyclohexylphosphino(biphenyl) ligand (0.7 mg, 0.002 mmol) and a catalytic amount of palladium acetate was stirred in dioxane overnight at 80° C. The title compound was obtained by preparative thin layer chromatography using 20% EtOAc/hexane. $^{1}$H NMR (CDCl$_{3}$, 600 MHz) δ 7.74 (m, 2H), 7.68 (d, J=7.8 Hz, 1H), 7.64 (t, J=7.8 Hz, 1H), 7.58 (t, J=7.8 Hz, 1H), 7.52 (m, 3H), 7.39 (d, J=7.2 Hz, 1H), 7.24 (m, 1H), 4.30-4.55 (m, 4H), 3.71 (s, 3H). LC-MS (M+1) 561.0 (4.29 min).

Example 150

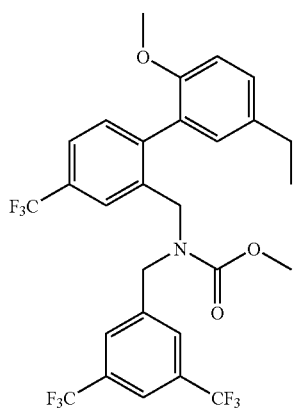

Methyl [3,5-bis(trifluoromethyl)benzyl]{[5'-ethyl-2'-methoxy-4-(trifluoromethyl)biphenyl-2-yl]methyl}carbamate Step A: 2-Iodo-4-ethylanisole A mixture of silver sulfate (1.15 g, 3.68 mmol) and iodine (0.93 g, 3.68 mmol) were stirred in methanol at room temperature. A solution of p-ethylanisole (0.50 g, 3.68 mmol) in methanol was added dropwise to the stirring mixture. The mixture was stirred at room temperature until completion of the reaction. It was filtered and the filtrate was concentrated. The residue was dissolved in methylene chloride, washed with 1 N sodium hydroxide, dried over anhydrous sodium sulfate, filtered and concentrated. The title compound was obtained without further purification. $^1$H NMR (CDCl$_3$, 500 MHz) δ 7.64 (d, J=2.0 Hz, 1H), 7.15 (dd, J=8.5, 2.0 Hz, 1H), 6.77 (d, J=8.0 Hz, 1H), 3.88 (s, 3H), 2.58 (q, J=15.5, 8.0 Hz, 2H), 1.23 (t, J=7.5 Hz, 3H).

Step B: 2-(5-Ethyl-2-methoxyphenyl)-4,4,5,5-tetramethyl-1,3,2-dioxaborolane

To a mixture of bispinacolatodiboron (0.70 g, 2.95 mmol), potassium acetate (0.67 g, 6.81 mmol) and dichlor[1,1'-bis(diphenylphosphino)ferrocene]palladium (II) dichloromethane adduct (55 mg, 0.068 mmol) in dioxane, 4-ethyl-2-iodoanisole (0.595 g, 2.27 mmol) from Step A was added. The reaction was stirred at 80° C. for 4 h then cooled to room temperature. After filtration to remove insoluble material, the solution was diluted in ethyl acetate, washed with water then brine, dried over anhydrous sodium sulfate, filtered and concentrated. The title compound was obtained by flash chromatography using 10% EtOAc/hexane. $^1$H NMR (CDCl$_3$, 600 MHz) δ 7.50 (d, J=2.4 Hz, 1H), 7.22 (dd, J=8.4, 2.4 Hz, 1H), 6.80 (d, J=8.4 Hz, 1H), 3.82 (s, 3H), 2.59 (q, J=15.6, 7.8 Hz, 2H), 1.36 (s, 12H), 1.22 (t, J=7.8 Hz, 3H). LC-MS (M+1) 263.3 (3.90 min).

Step C: Methyl [3,5-bis(trifluoromethyl)benzyl]{[5'-ethyl-2'-methoxy-4-(trifluoromethyl)biphenyl-2-yl]methyl}carbamate A mixture of methyl [3,5-bis(trifluoromethyl)benzyl](2-iodo-5-trifluoromethyl-benzyl)carbamate (105 mg, 0.18 mmol) (Example 5), the title compound from Step B (58 mg, 0.22 mmol), anhydrous potassium carbonate (50 mg, 0.36 mmol), dichloro[1,1'-bis(diphenylphospino)ferrocene]palladium(II) dichloromethane adduct (14.7 mg, 0.018 mmol), and a catalytic amount of palladium acetate in anhydrous dioxane were stirred at 80° C. for approximately 40 hours. The solvent was removed in vacuo, and the title compound was obtained by preparative thin layer chromatography using 60% CH$_2$Cl$_2$/hexane. $^1$H NMR (CDCl$_3$, 600 MHz) δ 7.71 (s, 1H), 7.56 (d, J=7.8 Hz, 1H), 7.45 (m, 2H), 7.32 (d, J=7.8 Hz, 1H), 7.25 (m, 1H), 7.21 (m, 1H), 6.88 (d, J=2.4 Hz, 1H), 6.87 (m, 1H), 4.23-4.56 (m, 4H), 3.74 (m, 3H), 3.68 (s, 3H), 2.60 (m, 2H), 1.24 (m, 3H). LC-MS (M+1) 594.0 (4.76 min).

We claim:

1. A compound having Formula I, or a pharmaceutically acceptable salt thereof, wherein

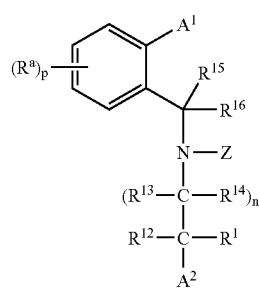

$A^1$ is selected from the group consisting of:
  (a) an aromatic ring selected from phenyl and naphthyl; and
  (b) a phenyl ring fused to a 5-7 membered non-aromatic cycloalkyl ring, which optionally comprises 1-2 double bonds;

$A^2$ is selected from the group consisting of:
  (a) an aromatic ring selected from phenyl and naphthyl;
  (b) a phenyl ring fused to a 5-7 membered non-aromatic cycloalkyl ring, which optionally comprises 1-2 double bonds; and
  (e) a —$C_3$-$C_8$ cycloalkyl ring optionally having 1-3 double bonds;

wherein $A^1$ and $A^2$ are each optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —O$C_1$-$C_6$alkyl, —O$C_2$-$C_6$ alkenyl, —O$C_2$-$C_6$ alkynyl, —O$C_3$-$C_8$ cycloalkyl optionally having 1-3 double bonds, —C(=O)$C_1$-$C_6$alkyl, —C(=O)$C_3$-$C_8$ cycloalkyl, —C(=O)H, —CO$_2$H, —CO$_2$$C_1$-$C_6$alkyl, —C(=O)S$C_1$-$C_6$alkyl, —NR$^{10}$R$^{11}$, —C(=O)NR$^{10}$R$^{11}$, —NR$^{10}$C(=O)O$C_1$-$C_6$ alkyl, —NR$^{10}$C(=O)NR$^{10}$R$^{11}$, —S(O)$_x$$C_1$-$C_6$ alkyl, —S(O)$_y$NR$^{10}$R$^{11}$, —NR$^{10}$S(O)$_y$NR$^{10}$R$^{11}$, halogen, —CN, —NO$_2$, and a 5-6-membered heterocyclic ring having 1-4 heteroatoms independently selected from N, S, and O, said heterocyclic ring optionally also comprising a carbonyl group and optionally also comprising 1-3 double bonds, wherein for compounds in which $R^a$ is selected from the group consisting of a heterocyclic ring, —$C_3$-$C_8$ cycloalkyl, —O$C_3$-$C_8$ cycloalkyl, and —C(=O)$C_3$-$C_8$ cycloalkyl, the heterocyclic ring and —$C_3$-$C_8$ cycloalkyl groups of $R^a$ are optionally substituted with 1-5 substituent groups independently selected from halogen, —$C_1$-$C_3$ alkyl, and —O$C_1$-$C_3$ alkyl, wherein —$C_1$-$C_3$ alkyl, and —O$C_1$-$C_3$ alkyl are optionally substituted with 1-7 halogens, wherein for compounds in which $R^a$ is selected from the group consisting of —$C_1$-$C_6$ alkyl, —$C_2$-$C_6$ alkenyl, —$C_2$-$C_6$ alkynyl, —$OC_1$-$C_6$alkyl, —$OC_2$-$C_6$ alkenyl, —$OC_2$-$C_6$ alkynyl, —C(=O)$C_1$-$C_6$alkyl, —$CO_2C_1$-$C_6$alkyl, —C(=O)S$C_1$-$C_6$alkyl, —$NR^{10}$C(=O)O$C_1$-$C_6$alkyl, and —S(O)$_x C_1$-$C_6$ alkyl, the alkyl, alkenyl, and alkynyl groups of Ra are optionally substituted with 1-15 halogens and are optionally also substituted with 1-3 substituent groups independently selected from (a) —OH, (b) —CN, (c) —$NR^{10}R^{11}$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl, (f) —$OC_3$-$C_8$ cycloalkyl optionally having 1-3 double bonds and optionally substituted with 1-15 halogens, (g) —$CO_2$H, (h) —C(=O)$CH_3$, and (i) —$CO_2C_1$-$C_4$alkyl which is optionally substituted with 1-9 halogens;

n is an integer selected from 0 and 1;
p is an integer from 0-4;
x is an integer selected from 0, 1, and 2;
y is an integer selected from 1 and 2;
Z is selected from the group consisting of —S(O)$_x C_1$-$C_6$ alkyl, —S(O)$_2 NR^{17}R^{18}$, —C(=S)O$C_1$-$C_6$alkyl, and —C(=O)X, wherein X is selected from the group consisting of H, —$C_1$-$C_6$ alkyl, —$OC_1$-$C_6$ alkyl, —S$C_1$-$C_6$ alkyl, and —$NR^{10}R^{11}$; wherein —$C_1$-$C_6$ alkyl in all instances is optionally substituted with 1-13 halogens and 1-2 substituents independently selected from —$OC_1$-$C_3$alkyl, —CN, and —$NO_2$, wherein —$OC_1$-$C_3$alkyl is optionally substituted with 1-7 halogens and is optionally also substituted with 1-2—$OC_1$-$C_2$ alkyl;
$R^1$, $R^{12}$, $R^{13}$, $R^{14}$, $R^{15}$, and $R^{16}$ are each independently selected from the group consisting of H, —OH, halogen, —$C_1$-$C_4$ alkyl, —$C_3$-$C_6$ cycloalkyl, —$OC_1$-$C_4$ alkyl, and —$NR^{10}R^{11}$, wherein —$C_1$-$C_4$ alkyl, —$C_3$-$C_6$ cycloalkyl, and —$OC_1$-$C_4$ alkyl are each optionally substituted with 1-9 halogens and are each optionally also substituted with 1-2 groups independently selected from —OH, —C(=O)$CH_3$, —OC(=O)$CH_3$, —$OC_1$-$C_2$ alkyl, and —$OC_1$-$C_2$ alkylene($OC_1$-$C_2$alkyl);
$R^{10}$ and $R^{11}$ are each independently selected from H, —$C_1$-$C_5$ alkyl, —C(=O)$C_1$-$C_5$ alkyl and —S(O)$_y C_1$-$C_5$ alkyl, wherein —$C_1$-$C_5$ alkyl in all instances is optionally substituted with 1-11 halogens; and
$R^{17}$ and $R^{18}$ are each independently selected from the group consisting of H, —$C_1$-$C_5$ alkyl, and —$C_3$-$C_7$ cycloalkyl, wherein —$C_1$-$C_5$ alkyl, and —$C_3$-$C_7$ cycloalkyl are optionally substituted with 1-13 halogens.

2. A compound of claim 1 having Formula Ia, or a pharmaceutically acceptable salt thereof, wherein

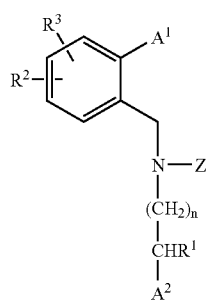

Ia $A^1$ is selected from the group consisting of:
(a) an aromatic ring selected from phenyl and naphthyl;
wherein $A^1$ is optionally substituted with 1-4 substituent groups independently selected from —$C_1$-$C_5$ alkyl, —$OC_1$-$C_3$alkyl, —$CO_2 C_1$-$C_3$alkyl, —$CO_2$H, halogen, —$NR^{10}R^{11}$, —C(=O)$C_1$-$C_3$alkyl, —C(=O)H, —C(=O)$NR^{10}R^{11}$, —S$C_1$-$C_3$ alkyl, —$C_2$-$C_3$ alkenyl, —CN, —$NO_2$, —$C_3$-$C_6$ cycloalkyl, and a 5-6-membered heterocyclic ring having 1-3 heteroatoms independently selected from N, S, and O, and optionally also comprising 1-3 double bonds, wherein —$C_1$-$C_3$ alkyl and —$C_1$-$C_5$ alkyl in all occurrences are optionally substituted with 1-6 substituents independently selected from 1-5 halogens and one —OH group; and —$C_3$-$C_6$ cycloalkyl and the 5-6-membered heterocyclic ring are optionally substituted with 1-3 substituents independently selected from halogen and —$C_1$-$C_3$ alkyl; and —$C_2$-$C_3$ alkenyl is optionally substituted with 1-3 halogens;

$A^2$ is selected from the group consisting of phenyl, naphthyl, and —$C_3$-$C_6$ cycloalkyl, wherein $A^2$ is optionally substituted with 1-2 substituent groups independently selected from —$C_1$-$C_4$ alkyl, —$OC_1$-$C_3$ alkyl, —C(=O)$C_1$-$C_3$alkyl, —C(=O)H, —$NO_2$, —CN, —S(O)$_x C_1$-$C_3$ alkyl, —NHS(O)$_2 C_1$-$C_3$ alkyl, —$NR^{10}R^{11}$, —$NR^{10}$C(=O)$R^{11}$, —$C_2$-$C_3$ alkenyl, —C(=O)$NR^{10}R^{11}$, halogen, —$C_3$-$C_6$ cycloalkyl, and a 5-6-membered heterocyclic ring having 1-3 heteroatoms independently selected from N, S, and O, and optionally also comprising 1-3 double bonds, wherein $C_1$-$C_3$ alkyl, $C_1$-$C_4$ alkyl, and $C_2$-$C_3$alkenyl in all instances are optionally substituted with 1-3 halogens, and —$C_3$-$C_6$ cycloalkyl and the 5-6-membered heterocyclic ring are optionally substituted with 1-3 substituents independently selected from halogen and —$C_1$-$C_3$ alkyl;

x is an integer selected from 0, 1, and 2;
n is an integer selected from 0 and 1;
$R^1$ is selected from the group consisting of H, OH, $C_1$-$C_3$ alkyl, and —$OC_1$-$C_3$ alkyl, wherein $C_1$-$C_3$ alkyl and —$OC_1$-$C_3$ alkyl are each optionally substituted with 1-3 halogens and also are optionally substituted with one —$OC_1$-$C_2$alkyl;
$R^2$ and $R^3$ are each independently selected from the group consisting of H, halogen, —$NR^{10}R^{11}$, —$C_1$-$C_3$ alkyl, —$OC_1$-$C_3$ alkyl, —$C_2$-$C_3$ alkenyl, —$C_3$-$C_6$ cycloalkyl optionally having a double bond, —$OC_3$-$C_6$ cycloalkyl optionally having a double bond, —C(=O)$C_1$-$C_3$alkyl, —C(=O)$C_3$-$C_6$ cycloalkyl, —C(=O)H, —$CO_2$H, —$CO_2 C_1$-$C_3$alkyl, —C(=O)$NR^{10}R^{11}$, —CN, —$NO_2$, and a 5-6-membered heterocyclic ring having 1-4 heteroatoms independently selected from N, S, and O, and optionally 1-3 double bond, wherein $C_1$-$C_3$ alkyl and —$C_2$-$C_3$ alkenyl in all instances are optionally substituted with 1-5 halogens, and —$C_3$-$C_6$ cycloalkyl and the 5-6-membered heterocyclic ring are in all occurrences optionally substituted with 1-3 substituents independently selected from halogen, —$C_1$-$C_3$ alkyl, —$OC_1$-$C_3$ alkyl, —$CF_3$, and —$OCF_3$; and
$R^{10}$ and $R^{11}$ are each independently selected from H and —$C_1$-$C_3$ alkyl.

3. The compound of claim 2, wherein $R^2$ and $R^3$ are each independently selected from the group consisting of H, halogen, —$NR^{10}R^{11}$, —$C_1$-$C_3$ alkyl, —$OC_1$-$C_3$ alkyl, —CN, —$NO_2$, and pyridyl, wherein $C_1$-$C_3$ alkyl in all instances is optionally substituted with 1-3 halogens, or a pharmaceutically acceptable salt thereof.

4. The compound of claim 2 having the formula Ib, or a pharmaceutically acceptable salt thereof:

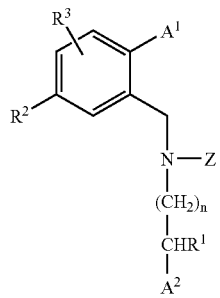

5. The compound of claim 4, wherein $R^2$ is selected from the group consisting of H, halogen, —$NR^{10}R^{11}$, —$C_1$-$C_3$ alkyl, —$OC_1$-$C_3$ alkyl, —CN, —$NO_2$, and pyridyl, wherein $C_1$-$C_3$ alkyl in all instances is optionally substituted with 1-3 halogens; and $R^3$ is selected from the group consisting of H, halogen, —$CH_3$, —$CF_3$, —$OCH_3$, and —$OCF_3$, or a pharmaceutically acceptable salt thereof.

6. The compound of claim 4, wherein $A^1$ is phenyl; and $A^2$ is selected from the group consisting of phenyl, and $C_3$-$C_6$ cycloalkyl;

wherein A1 and A2 are optionally substituted as in claim 4, or a pharmaceutically acceptable salt thereof.

7. The compound of claim 6, wherein $A^2$ is selected from phenyl, and cyclohexyl;

wherein A1 and A2 are optionally substituted as in claim 4, or a pharmaceutically acceptable salt thereof.

8. The compound of claim 1 having formula II, or a pharmaceutically acceptable salt thereof, wherein

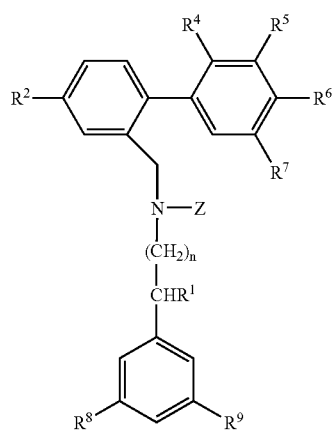

$R^1$ is selected from the group consisting of H, halogen, and $C_1$-$C_3$ alkyl, wherein $C_1$-$C_3$ alkyl is optionally substituted with 1-3 halogens;

$R^2$ is selected from the group consisting of H, halogen, —$NR^{10}R^{11}$, —$OC_1$-$C_3$ alkyl, $C_1$-$C_3$ alkyl, —CN, —$NO_2$, and pyridyl, wherein $C_1$-$C_3$ alkyl in all occurrences is optionally substituted with 1-3 halogens;

$R^4$ is selected from the group consisting of H, halogen, —$C_1$-$C_3$ alkyl, —$OC_1$-$C_2$ alkyl, —$SC_1$-$C_2$ alkyl and —CN, wherein —$C_1$-$C_3$ alkyl, —$SC_1$-$C_3$ alkyl, and —$OC_1$-$C_3$ alkyl are optionally substituted with 1-3 F;

$R^5$ and $R^6$ are independently selected from the group consisting of H, halogen, —$CH_3$ and —$OCH_3$, wherein —$CH_3$ and —$OCH_3$ are optionally substituted with 1-3 F;

$R^7$ is selected from the group consisting of H, —$C_1$-$C_5$alkyl, —$OC_1$-$C_3$ alkyl, —$C_2$-$C_3$ alkenyl, halogen, —CN, —$CO_2H$, —$CO_2C_1$-$C_3$ alkyl, —$SC_1$-$C_3$ alkyl, —$C(=O)NR^{10}R^{11}$, —$C(=O)H$, —$C(=O)C_1$-$C_3$ alkyl, $C_3$-$C_6$ cycloalkyl, and 5-(1,2,4-oxadiazolyl), wherein —$C_1$-$C_3$ alkyl and —$C_1$-$C_5$ alkyl in all occurrences is optionally substituted with 1-6 substituent groups independently selected from 1-5 halogens and one —OH, —$C_2$-$C_3$ alkenyl is optionally substituted with 1-3 halogens, and 1,2,4-oxadiazolyl and $C_3$-$C_6$ cycloalkyl are optionally substituted with 1-2 substituent groups independently selected from halogen and $C_1$-$C_3$ alkyl;

$R^8$ and $R^9$ are each independently selected from the group consisting of H, —$C_1$-$C_3$ alkyl, halogen, —$S(O)_xC_1$-$C_3$ alkyl, —$NR^{10}R^{11}$, —$OC_1$-$C_3$alkyl, $C_2$-$C_3$ alkenyl, —$NO_2$, —CN, —$C(O)NR^{10}R^{11}$, —$C(=O)H$, —NHC$(=O)C_1$-$C_3$ alkyl, —$NHS(O)_2C_1$-$C_3$ alkyl, $CO_2H$, $CO_2C_1$-$C_3$alkyl, $C_3$-$C_6$ cycloalkyl, and pyridyl, wherein $C_1$-$C_3$ alkyl in all occurrences is optionally substituted with 1-3 halogens, $C_2$-$C_3$ alkenyl is optionally substituted with 1-3 halogens, and $C_3$-$C_6$ cycloalkyl and pyridyl are optionally substituted with 1-2 substituent groups independently selected from halogen and $C_1$-$C_3$ alkyl;

$R^{10}$ and $R^{11}$ are each H or $C_1$-$C_3$ alkyl;

Z is selected from the group consisting of —$C(=O)C_1$-$C_3$ alkyl, —$C(=O)OC_1$-$C_3$ alkyl, —$S(O)_yC_1$-$C_3$ alkyl, —$C(=O)H$, —$C(O)NR^{10}R^{11}$, —$C(=O)SC_1$-$C_3$ alkyl, and —$C(=S)OC_1$-$C_3$ alkyl;

n is an integer selected from 0 and 1;

x is an integer selected from 0, 1 and 2; and y is an integer selected from 0 and 1.

9. A compound of claim 8, wherein $R^1$ is H or $CH_3$;

$R^2$ is selected from the group consisting of H, —$CF_3$, —$OCH_3$, —$NO_2$, —CN, halogen, —$NH_2$ and 3-pyridyl;

$R^4$ is selected from the group consisting of H, halogen, —$CH_3$, —$C_2H_5$, —$OCH_3$, —$OC_2H_5$, —$SCH_3$, and —CN;

$R^5$ is selected from the group consisting of H and F;

$R^6$ is selected from the group consisting of H, F, —$CH_3$, and —$OCH_3$;

$R^7$ is selected from the group consisting of H, $C_1$-$C_4$alkyl, —$C(=O)H$, —$C(=O)CH_3$, —$CH=CH_2$, —CN, Cl, F, —$CO_2H$, —$CO_2C_1$-$C_3$alkyl, —$OCH_3$, —$SCH_3$, —$C(=O)NR^{10}R^{11}$, and 3-methyl-5-(1,2,4-oxadiazolyl), wherein $C_1$-$C_4$alkyl is optionally substituted with 1-6 substituents which are independently selected from 1-5 F and one —OH;

$R^8$ and $R^9$ are each independently selected from the group consisting of H, $C_1$-$C_2$alkyl, which is optionally substituted with 1-3 F; halogen; —CN; —$NO_2$; —$S(O)_xCH_3$, which is optionally substituted with 1-3F; —$OCH_3$, which is optionally substituted with 1-3 F; —$CH=CH_2$; —$C(=O)H$; —$C(=O)NR^{10}R^{11}$; —$CO_2H$; —$NR^{10}R^{11}$; —$CO_2C_1$-$C_3$alkyl; —NHC$(=O)CH_3$; —$NHS(O)_2CH_3$; and 4-pyridyl; and $R^{10}$ and $R^{11}$ are each independently selected from H and $CH_3$, or a pharmaceutically acceptable salt thereof.

10. A compound of claim 9, wherein n is 0, or a pharmaceutically acceptable salt thereof.
11. A compound of claim 1, which is selected from the following compounds, or a pharmaceutically acceptable salt thereof:
TABLE 1
| Example | Structure |
|---|---|
| Ex. 6 | 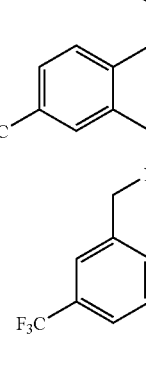 |
| Ex. 7 | 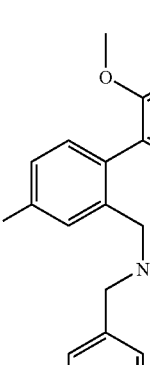 |
| Ex. 8 | 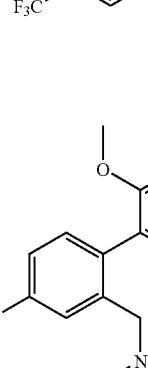 |
TABLE 1-continued
| Example | Structure |
|---|---|
| Ex. 9 | 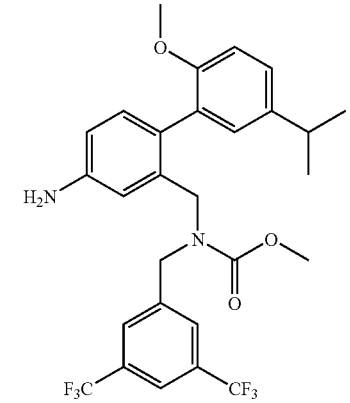 |
| Ex. 10 | 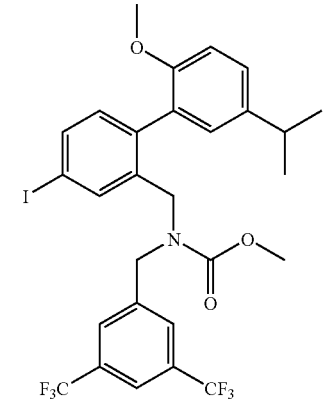 |
| Ex. 11 | 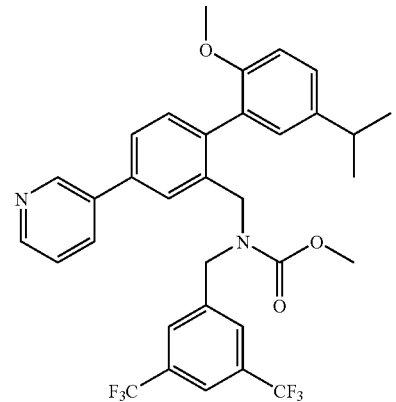 |

TABLE 1-continued

| Example | Structure |
|---|---|
| Ex. 12 | |
| Ex. 13 | |
| Ex. 14 | |
| Ex. 19 | 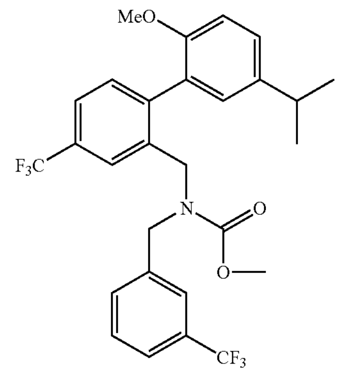 |
| Ex. 22 | 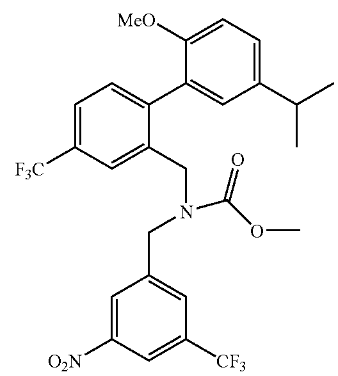 |
| Ex. 28 | 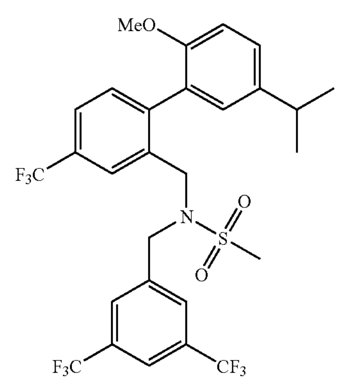 |
| Ex. 29 | 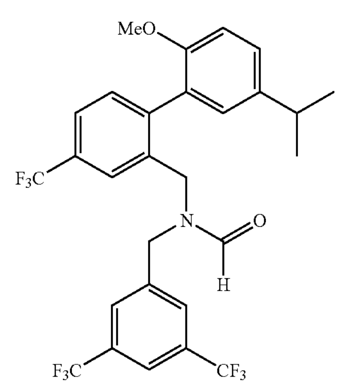 |

TABLE 1-continued

| Example | Structure |
|---------|-----------|
| Ex. 30 | (structure) |
| Ex. 31 | (structure) |
| Ex. 32 | (structure) |
| Ex. 33 | (structure) |
| Ex. 34 | (structure) |
| Ex. 35 | (structure) |
| Ex. 36 | (structure) |

TABLE 1-continued

| Example | Structure |
|---|---|
| Ex. 37 | (structure) |
| Ex. 38 | (structure) |
| Ex. 39 | (structure) |
| Ex. 40 | (structure) |
| Ex. 41 | (structure) |
| Ex. 42 | (structure) |
| Ex. 43 | (structure) |

TABLE 1-continued
| Example | Structure |
|---------|-----------|
| Ex. 44 | 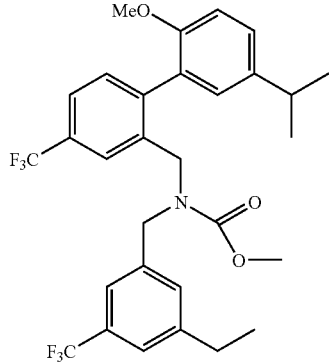 |
| Ex. 45 | 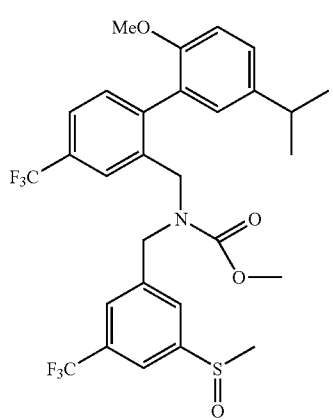 |
| Ex. 46 | 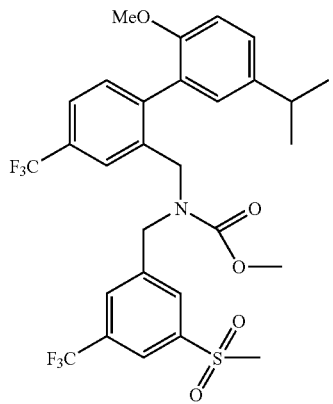 |
TABLE 1-continued
| Example | Structure |
|---------|-----------|
| Ex. 48 | 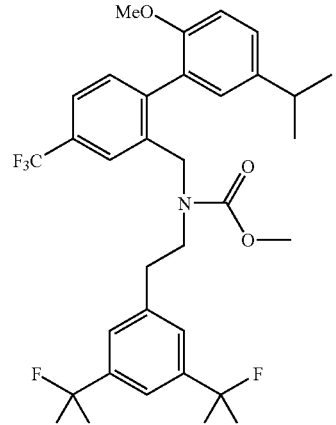 |
| Ex. 135 | 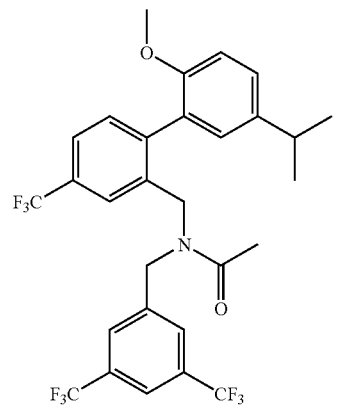 |
| Ex. 136 | 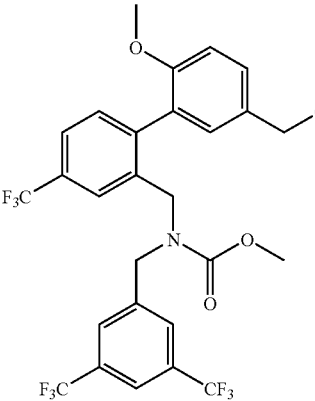 |

TABLE 1-continued

| Example | Structure |
| --- | --- |
| Ex. 137 | (structure) |
| Ex. 138 | (structure) |
| Ex. 139 | (structure) |
| Ex. 140 | (structure) |
| Ex. 141 | (structure) |
| Ex. 142 | (structure) |

TABLE 1-continued

| Example | Structure |
|---------|-----------|
| Ex. 143 | |
| Ex. 144 | |
| Ex. 145 | |
| Ex. 146 | 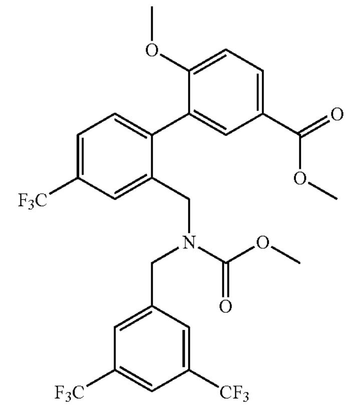 |
| Ex. 147 | 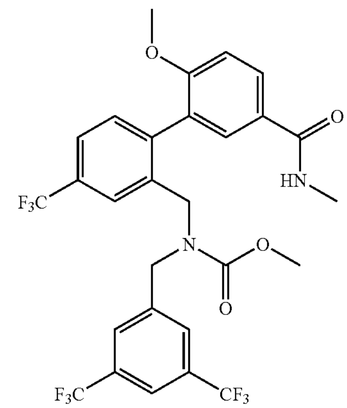 |
| Ex. 148 | 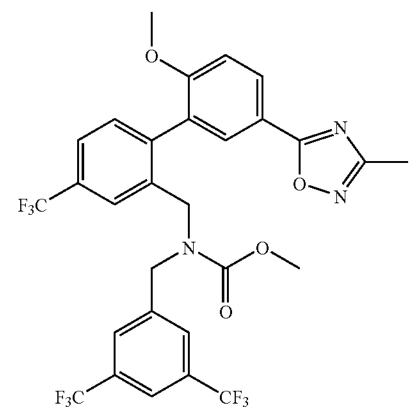 |
| Ex. 149 | 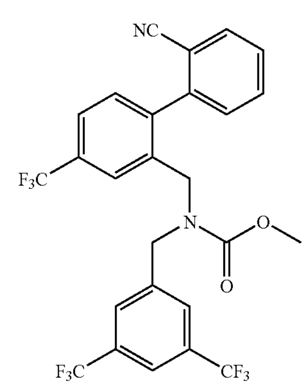 |

TABLE 1-continued
| Example | Structure |
|---|---|
| Ex. 150 | 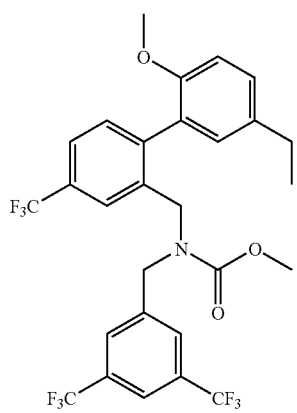 |
TABLE 2
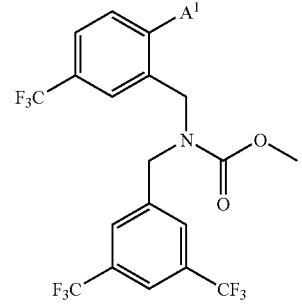
| Example | A' |
|---|---|
| 51 | MeO- (2-position) |
| 52 | MeO, Me substituted phenyl |
| 53 | MeO, Cl substituted phenyl |
| 54 | Me substituted phenyl |
TABLE 2-continued
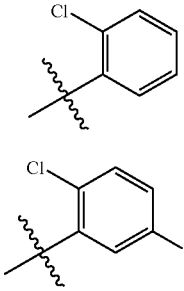
| Example | A' |
|---|---|
| 55 | Cl substituted phenyl |
| 56 | 2,5-diCl phenyl |
| 57 | EtO, Me substituted phenyl |
| 58 | MeO, F substituted phenyl |
| 59 | MeO, 2,5-diF phenyl |
| 60 | MeO, 4,5-diF phenyl |
| 61 | MeO, OMe substituted phenyl |
| 62 | MeO, iPr substituted phenyl |
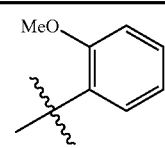

TABLE 2-continued

[Structure: 2-(trifluoromethyl)benzyl and 3,5-bis(trifluoromethyl)benzyl groups connected to N-methylcarbamate, with A¹ substituent]

| Example | A' |
|---------|-----|
| 63 | 3-OMe-phenyl |
| 64 | 2-MeO-4-F-phenyl |
| 65 | 2-Me-5-OMe-phenyl |
| 66 | 2,4-(MeO)₂-phenyl |
| 67 | 2,5-dimethylphenyl |
| 68 | 2-MeO-5-CF₃-phenyl |
| 69 | 2-MeO-5-propyl-phenyl |
| 70 | 2-MeO-5-tert-butyl-phenyl |
| 71 | 2,4,5-trimethylphenyl |
| 72 | 2-MeS-phenyl |
| 73 | 4-MeO-3-CHO-phenyl |
| 74 | 2-MeO-4-F-5-isopropyl-phenyl |
| 75 | 2-MeO-4-F-5-methyl-phenyl |
| 82 | 2-Cl-4-F-5-methyl-phenyl |
| 91 | phenyl |
| 96 | 2-ethylphenyl |

TABLE 2-continued

[Structure: 2-A¹-5-(trifluoromethyl)benzyl N-(3,5-bis(trifluoromethyl)benzyl)-N-methoxycarbonyl]

| Example | A¹ |
|---|---|
| 97 | 4-MeO, 5-vinyl phenyl |

TABLE 3

[Structure: 2-A¹-5-R²-benzyl N-(3,5-bis(trifluoromethyl)benzyl)-N-methoxycarbonyl]

| EXAMPLE | A¹ | R² |
|---|---|---|
| 103 | 4-MeO, 5-methyl phenyl | OMe |
| 104 | 4-MeO, 5-isopropyl phenyl | OMe |
| 105 | 4-MeO, 5-isopropyl phenyl | F |

TABLE 3-continued

| EXAMPLE | A¹ | R² |
|---|---|---|
| 106 | 4-MeO, 5-propyl phenyl | F |
| 107 | 4-MeO, 5-tert-butyl phenyl | F |
| 108 | 4-MeO, 5-methyl phenyl | H |
| 108a | 4-MeO, 5-F, 4-methyl phenyl | Cl |
| 109 | 4-MeO, 5-isopropyl phenyl | H |
| 110 | 4-MeO, 5-F, 4-isopropyl phenyl | Cl |

TABLE 4
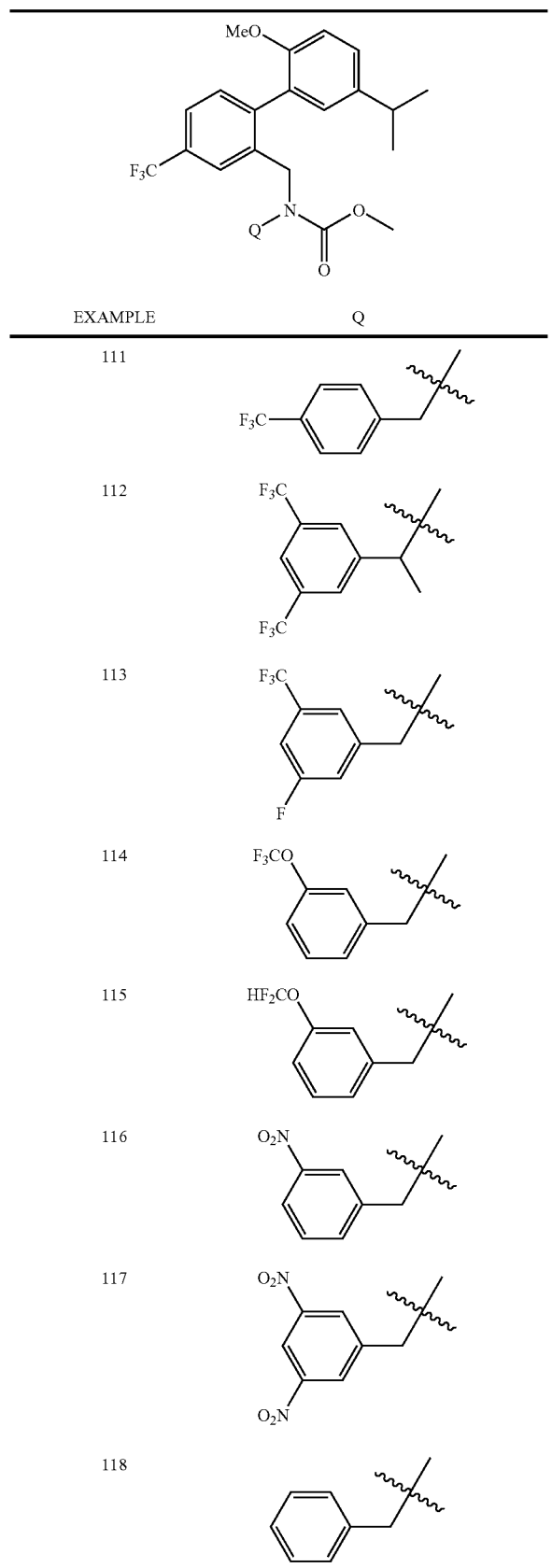
TABLE 4-continued
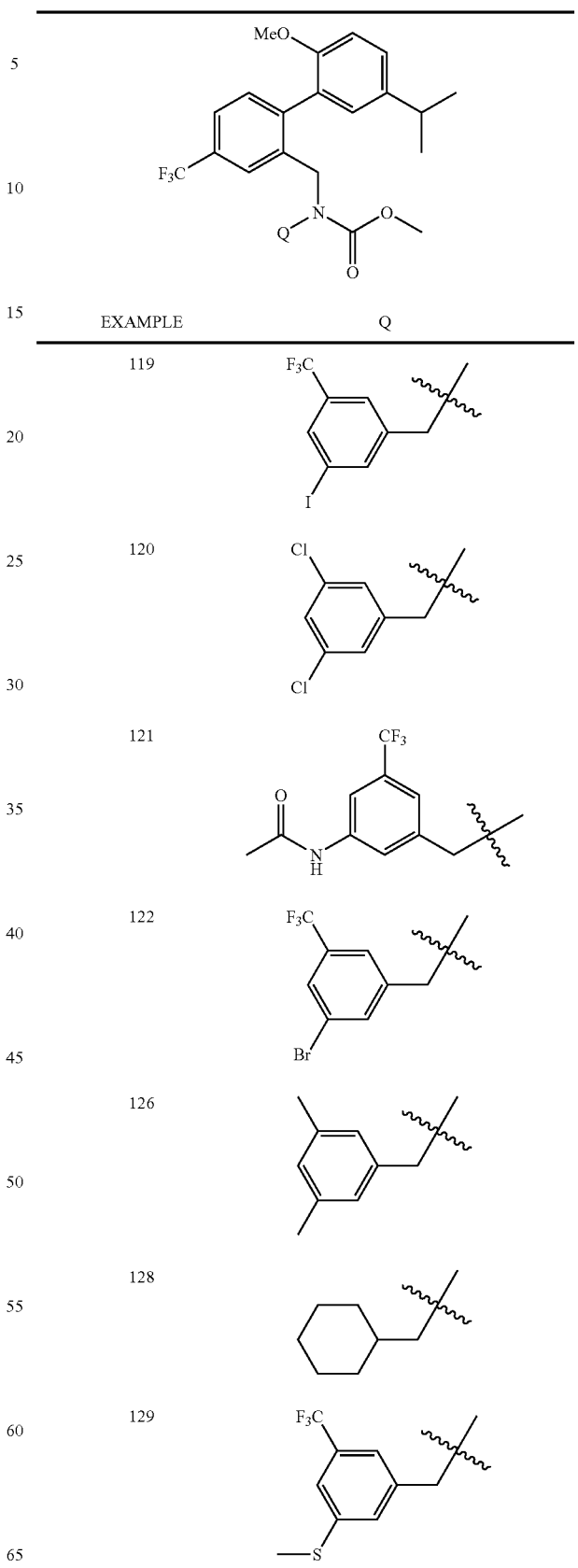

TABLE 4-continued

EXAMPLE Q

130

TABLE 5

EXAMPLE Z

131

132

TABLE 5-continued

EXAMPLE Z

133

12. A method of treating atherosclerosis in a patient in need of treatment comprising the administration of a therapeutically effective amount of the compound of claim 1 to said patient.

13. A method of raising HDL-C in a patient in need of treatment comprising the administration of a therapeutically effective amount of the compound of claim 1 to said patient.

14. A pharmaceutical composition comprising a compound of claim 1, or a pharmaceutically acceptable salt thereof, and a pharmaceutically acceptable carrier.

15. The use of a compound of claim 1 or a pharmaceutically acceptable salt thereof for the manufacture of a medicament for the treatment of atherosclerosis.

16. A pharmaceutical composition comprising a compound of claim 1, or a pharmaceutically acceptable salt thereof, and one or more active ingredients selected from the group consisting of: (a) PPAR gamma agonists and partial agonists;
  (b) biguanides;
  (c) protein tyrosine phosphatase-1B (PTP-1B) inhibitors,
  (d) dipeptidyl peptidase IV (DP-IV) inhibitors;
  (e) insulin or insulin mimetics;
  (f) sulfonylureas;
  (g) α-glucosidase inhibitors;
  (h) one or more compounds selected from the group consisting of (a) HMG-CoA reductase inhibitors; (b) bile acid sequestrants; (c) niacin, nicotinyl alcohol, nicotinamide, and nicotinic acid or a salt thereof; (d) PPARα agonists; (e) cholesterol absorption inhibitors; (f) acyl CoA:cholesterol acyltransferase (ACAT) inhibitors; (g) phenolic anti-oxidants, such as probucol, and (h) a microsomal triglyceride transfer protein (MTP)/ApoB secretion inhibitor;
  (i) PPARα/γ dual agonists;
  (j) PPARδ agonists;
  (k) antiobesity compounds
  (l) ileal bile acid transporter inhibitors;
  (m) anti-inflammatory agents;
  (n) glucagon receptor antagonists;
  (o) GLP-1,
  (p) GIP-1, and
  (q) GLP-1 analogs.

* * * * *